United States Patent
Ivarie et al.

(10) Patent No.: US 7,511,120 B2
(45) Date of Patent: Mar. 31, 2009

(54) GLYCOSYLATED G-CSF OBTAINED FROM A TRANSGENIC CHICKEN

(75) Inventors: Robert D. Ivarie, Watkinsville, GA (US); Alex J. Harvey, Athens, GA (US); Julie A. Morris, Watkinsville, GA (US); Guodong Liu, Mississagua (CA); Jeffrey C. Rapp, Athens, GA (US)

(73) Assignees: Synageva BioPharma Corp., Waltham, MA (US); University of Georgia Research Foundation, Athens, GA (US)

( * ) Notice: Subject to any disclaimer, the term of this patent is extended or adjusted under 35 U.S.C. 154(b) by 0 days.

(21) Appl. No.: 11/708,598

(22) Filed: Feb. 20, 2007

(65) Prior Publication Data
US 2007/0243165 A1   Oct. 18, 2007

Related U.S. Application Data

(63) Continuation-in-part of application No. 11/370,555, filed on Mar. 8, 2006, now Pat. No. 7,338,654, which is a continuation of application No. 10/351,196, filed on Jan. 24, 2003, now Pat. No. 7,129,390, which is a continuation-in-part of application No. 09/173,864, filed on Oct. 16, 1998, now Pat. No. 6,730,822.

(60) Provisional application No. 60/062,172, filed on Oct. 16, 1997, provisional application No. 60/783,648, filed on Mar. 17, 2006, provisional application No. 60/840,291, filed on Aug. 25, 2006.

(51) Int. Cl.
*C07K 38/00* (2006.01)
*A61K 38/00* (2006.01)

(52) U.S. Cl. ........................................ 530/350; 514/12
(58) Field of Classification Search ........................ None
See application file for complete search history.

(56) References Cited

U.S. PATENT DOCUMENTS

| | | | |
|---|---|---|---|
| 4,496,537 A | 1/1985 | Kwan | |
| 4,959,317 A | 9/1990 | Sauer | |
| 4,997,763 A | 3/1991 | Hughes et al. | |
| 5,162,215 A | 11/1992 | Bosselman et al. | |
| 5,304,489 A | 4/1994 | Rosen | |
| 5,364,783 A | 11/1994 | Ruley et al. | |
| 5,367,054 A | 11/1994 | Lee | |
| 5,378,618 A | 1/1995 | Sternberg et al. | |
| 5,464,764 A | 11/1995 | Capecchi et al. | |
| 5,487,992 A | 1/1996 | Capecchi et al. | |
| 5,677,177 A | 10/1997 | Wahl et al. | |
| 5,714,353 A | 2/1998 | Pathak et al. | |
| 5,741,957 A | 4/1998 | Deboer et al. | |
| 5,784,992 A | 7/1998 | Petitte et al. | |
| 6,069,133 A | 5/2000 | Chiou et al. | |
| 6,825,396 B2 | 11/2004 | MacArthur | |

FOREIGN PATENT DOCUMENTS

| | | |
|---|---|---|
| EP | 0 424 027 A1 | 4/1991 |
| EP | 0 424 044 A1 | 4/1991 |
| WO | WO 90/11355 | 10/1990 |
| WO | WO 94/20608 | 9/1994 |
| WO | WO 95/11302 | 4/1995 |
| WO | WO 97/33998 | 9/1997 |
| WO | WO 97/47739 | 12/1997 |
| WO | WO 98/01027 | 1/1998 |
| WO | WO 03/022040 | 3/2003 |
| WO | WO 03/022228 | 3/2003 |
| WO | WO 2004/047531 | 6/2004 |

OTHER PUBLICATIONS

Huising et al., J. Endocr. 189: 1-25, 2006.*
Adolf et al., "Natural human interferon-α2 is O-glycosylated," *Biochem J.*, 276:511-518, (1991).
Allioli et al., "Use of retroviral vectors to introduce and express the β-galactosidase marker gene in cultured chicken primordial germ cells," *Developmental Biology*, 165:30-37 (1994).
Archer et al., "Human growth hormone (hgh) secretion in milk of goats after direct transfer of the hgh gene into the mammary gland by using replication-defective retrovirus vectors," *Proc. Natl. Acad. Sci. USA*, 91:6840-6844 (1994).
Bayley et al., "Exchange of Gene Activity in Transgenic plants catalyzed by the Cre-lox site-specific recombination system," *Plant Molecular Biology*, 18:353-361 (1992).
Beato, M. "Gene regulation by steroid hormones," *Cell*, 56:335-344 (1989).
Bonifer et al., "Tissue specific and position independent expression of the complete gene domain for chicken lysozyme in transgenic mice," *The EMBO Journal*, 9:2843-2848 (1990).
Bosselman et al., "Germline transmission of exogenous genes in the chicken," *Science*, 243:533-535 (1989).
Brazolot et al., "Efficient transfection of chicken cells by lipofection, and introduction of transfected blastodermal cells into the embryo," *Molecular Reproduction and Development*, 30:304-312 (1991).
Briskin et al., "Heritable retroviral transgenes are highly expressed in chickens," *Proc. Natl. Acad. Sci. USA*, 88:1736-1740 (1991).
Brown et al., "Conformational alterations in the proximal portion of the yeast invertase signal peptide do not block secretion," *Mol. Gen. Genet.*, 197:351-357 (1984).
Burns et al., "Vesicular stomatitis virus G glycoprotein pseudotyped retroviral vectors: concentration to very high titer and efficient gene transfer into mammalian and nonmammalian cells," *Proc. Natl. Acad. Sci. USA*, 90:8033-8037 (1993).
Chung et al., "A 5' element of the chicken β-globin domain serves as an insulator in human erythroid cells and protects against position effect in drosophila," *Cell*, 74:505-514 (1993).
Cosset et al., "Improvement of avian leucosis virus (ALV)-based retrovirus vectors by using different cisacting sequences from ALVs," *Journal of Virology*, 65:3388-3394 (1991).

(Continued)

*Primary Examiner*—Robert Landsman
*Assistant Examiner*—Gyan Chandra
(74) *Attorney, Agent, or Firm*—Kyle D. Yesland

(57) ABSTRACT

Granulocyte colony stimulating factor obtained from eggs laid by transgenic avians having newly described G-CSF glycosylation patterns.

10 Claims, 21 Drawing Sheets

OTHER PUBLICATIONS

Cosset et al., "Use of helper cells with two host ranges to generate high-titer retroviral vectors," *Virology* 193:385-395 (1993).

Dean et al., "Regulation of the chicken ovalbumin gene by estrogen and corticosterone requires a novel DNA element that binds a labile protein, chirp-1," *Molecular and Cellular Biology*, 16:2015-2024 (1996).

Deeley et al., "Synthesis and Deposition of Egg Proteins," eds Robert J. Etches, Ph.D, D.Sc.and Ann M. Verrinder Gibbins, Ph.D., Manipulation of the Avian Genome, Boca Raton, CRC Press (1993), p. 205.

Dierich et al., "Cell-specificity of the chicken ovalbumin and conalbumin promoters," *The EMBO Journal*, 6:2305-2312 (1987).

Dugaiczyk et al., "The ovalbumin gene: cloning and molecular organization of the entire natural gene," *Proc. Natl. Acad. Sci. USA*, 76:2253-2257 (1979).

Etches et al., "Contributions to somatic and germline lineages of chicken blastodermal cells maintained in culture," *Molecular Reproduction and Development*, 45:291-298 (1996).

Fiering S. et al., "An "in-out" strategy using gene targeting and FLP recombinase for the functional dissection of complex DNA regulatory elements: Analysis of the β-globin locus control region," *Proc. Natl. Acad. Sci USA*, vol. 90, 18, Sep. 15, 1993, pp. 8469-8473.

Fisher et al., "Expression of exogenous protein and analysis of morphogenesis in the developing chicken heart using an adenoviral vector," *Cardiovascular Research*, 31:E86-E95 (1996).

Galton et al., "Antibodies to Lymphoblastoid Interferon," *Lancet*, 2:572-573, (1989).

Gannon et al., "Organization and sequences at the 5' end of a cloned complete ovalbumin gene," *Nature*, 276:428-434 (1979).

Gilbert, Egg albumin and its formation in Physiology and Biochemistry of the Domestic Fowl, Bell and Freeman, eds., Academic Press, London, NY, pp. 1291-1329.

Gu et al., "Deletion of a DNA polymerase β gene segment in T cells using cell type-specific gene targeting," *Science*, 265:103-106 (1994).

Haecker et al., "Repression of the ovalbumin gene involves multiple negative elements including an ubiquitous transcriptional silencer," *Molecular Endocrinology*, 9:1113-1126 (1995).

Hale, K.L., "Oncolog, Interferon: The Evolution of a Biological Therapy, Taking a New Look at Cytokine Biology," *M.D. Anderson Oncolog*, 39(4):1-4 (1994).

Hogan et al., "Manipulating the Mouse Embryo," Cold Spring Harbor Laboratory, NY, (1988).

Johnson et al., "pXeX, a vector for efficient expression of cloned sequences in *Zenopus* embryos," *Gene*, 147:223-226 (1994).

Kato et al., "A far upstream estrogen response element of the ovalbumin gene contains several half-palindromic 5'-TGACC-3' motifs acting synergistically," *Cell*, 68:731-742 (1992).

Kaye et al., "A close association between sites of Dnase I hypersensitivity and sites of enhanced cleavage by micrococcal nuclease in the 5'-flanking region of the actively transcribed ovalbumin gene," *The EMBO Journal*, 3:1127-1144 (1984).

Kotani et al., "Improved methods of retroviral vector transduction and production for gene therapy," *Hum. Gene Ther.* 5:19-28 (1994).

Lai et al., "The ovalbumin gene: structural sequences in native chicken DNA are not contiguous," *Proc. Natl. Acad. Sci. USA*, 75:2205-2209 (1978).

Lin et al., "Integration and germ-line transmission of a pseudotyped retroviral vector in zebrafish," *Science*, 265:666-669 (1994).

Lobe et al., "Conditional genome alteration in mice," *BioEssays*, 20:200-208 (1998).

Logie et al., "Ligand-regulated site-specific recombination," *Proc. Natl. Acad. Sci. USA*, 92:5940-5944 (1995).

Lou et al., "Adenovirus-mediated gene transfer into tendon and tendon sheath," *Journal of Orthopaedic Research*, 14:513-517 (1996).

Lobe et al., "Transgenic birds by DNA microinjection," *Bio/Technology*, 12:60-63 (1994).

Moore et al., "The development of β-lactamase as a highly versatile genetic reporter for eukaryotic cells," *Analytical Biochemistry*, 247:203-209 (1997).

Mountford et al., "Dicistronic targeting constructs: reporters and modifiers of mammalian gene expression," *Proc. Natl. Acad. Sci. USA*, 91:4303-4307 (1994).

Muramatsu, T. et al., "Gene gun-mediated in vivo analysis of tissue-specific repression of gene transcription driven by the chicken ovalbumin promoter in the liver and oviduct of laying hens." *Molecular and Cellular Biochemistry*, vol. 185, No. 1-2, Aug. 1998, pp. 27-32.

Myllya et al., *Biochem J.*, 196:683-692 (1981).

Nordstrom et al., "A complex array of double-stranded and single-stranded DNA-binding proteins mediates induction of the ovalbumin gene by steroid hormones," *The Journal of Biological Chemistry*, 268:13193-13202 (1993).

Nyman et al., Structural characterisation of N-linked and O-lined oligosaccharides derived from interferon-α2b and interferon -α14c produced by Sendai-virus-induced human peripheral blood leukocutes, *Eur. J. Biochem.*, 253:485-493 (1998).

Ochiai et al., Synthesis of human erythropoietin in vivo in the oviduct of laying hens by localized in vivo gene transfer using electroporation, *Poultry Science*, 77:299-302 (1998).

Odell et al., "Seed-specific gene activation mediated by the cre/lox site-specific recombination system," *Plant Physiol.*, 106:447-458 (1994).

Otten et al., "The MMTV LTR promoter is induced by progesterone and dihydrostestosterone but not by estrogen," *Molecular Endocrinology*, 2:143-147 (1988).

Palmiter, R.D., "Quantitation of parameters that determine the rate of ovalbumin synthesis," *Cell*, 4:189-197 (1975).

Palmiter, R.D., "Rate of ovalbumin messenger ribonucleic acid synthesis in the oviduct of estrogen-primed chicks," *The Journal of Biological Chemistry*, 248:8260-8270 (1973).

Park et al., "Modulation of transcriptional activity of the chicken ovalbumin gene promoter in primary cultures of chicken oviduct cells: effects of putative regulatory elements in the 5'-flanking region," *Biochemistry and Molecular Biology International*, 36:811-816 (1995).

Roop et al., "Definition of the 5' and 3' ends of transcripts of the ovalbumin gene," *Cell*, 19:63-68 (1980).

Royal et al., "The ovalbumin gene region: common features in the organization of three genes expressed in chicken oviduct under hormonal control," *Nature*, 279:324-331 (1997).

Rucker et al., "Cre-mediated recombination at the murine whey acidic protein (mWAP) locus," *Molecular Reproduction and Development*, 48:324-331 (1997).

Sanders et al., "Positive and negative regulatory elements control the steroid-responsive ovalbumin promoter," *Biochemistry*, 27:6550-6557 (1988).

Sang TIBTECH 12:415-420 (1994).

Sauer, B., "Manipulation of transgenes by site-specific recombination: use of cre recombinase," *Methods in Enzymology*, 225:890-900 (1993).

Schweers et al., "A protein with a binding specificity similar to $NF-_\kappa B$ binds to a steroid-dependent regulatory element in the ovalbumin gene," *The Journal of Biological Chemistry*, 266:10490-10497 (1991).

Simkiss, "Transgenic birds, animals with novel genes," McLean ed., Cambridge Univ. Press NY pp. 106-135 (1994).

Thoraval et al., "Germline transmission of exogenous genes in chickens using helper-free ecotropic avian leucosis virus-based vectors," *Transgenic Research*, 4:369-376 (1995).

Uyeda et al., "Cloning and sequencing of hen magnum cDNAs encoding viteline membrane outer layer protein I (VMO-1)," *Gene*, 144:311-312 (1994).

Vick et al., "Transgenic birds from transformed primordial germ cells," *Proc. R. Soc. Lond. B.*, 179-183 (1993).

Wentworth et al., "Manipulation of Avian Primordial Germ Cells and Gonadal Differentiation," *Poultry Science*, 68(7):999-1010 (1988).

Yee et al., "Generation of high-titer pseudotyped retroviral vectors with very broad host range," *Methods in Cell Biology*, 43:99-112 (1994).

Zhang et al., "Inducible site-directed recombination in mouse embryonic stem cells," *Nucleic Acids Research*, 24:543-548 (1996).

Zolotukhin et al., "A "humanized" green fluorescent protein cDNA adapted for high-level expression in mammalian cells," *Journal of Virology*, 70:4646-4654 (1996).

Rendell, et al., Bichem. And Mol. Biol. 81:819-822, (1985).

Rohrer, J.S. and White, H.B., Biochem J. 285:275-280, 1992.

Anderson et al., Monosaccharide and oligosaccharide analysis of isoelectric focusing-separated and blotted granulocyte colony-stimulating factor glycoforms using high-pH anion-exchange chromatography with pulsed amperometric detection, Glycobiology, 4:(4)459-467 (1994).

Carter et al., The significance of carbohydrates on G-CSF: differential sensitivity of G-CSFs to human neutrophil elastase degradation, Journal of Leukocyte Biology, 75:515-522 (2004).

Dipaola et al., Interferon-A2 Produced by Normal Human Leukocytes Is Predominantly Interferon-A2b, Journal of Interferon Research, 14:325-332 (1994).

Gewert et al., Analysis of Interferon-A2 Sequences in Human Genomic DNA, Journal of Interferon Research, 13:227-231 (1993).

Holloway, Applications of Recombinant DNA Technology in the Production of Glycosylated Recombinant Human Granulocyte Colony Stimulating Factor, European Journal of Cancer, 30A:(Suppl 3)S2-S6 (1994).

Nomura et al., Purification and characterization of human granulocyte colony-stimulating factor (G-CSF), The EMBO Journal, 5:(5) 871-876 (1986).

Oheda et al., Structures of Sugar Chains of Recombinant Human Granulocyte-Colony-Stimulating Factor Produced by Chinese Hamster Ovary Cells, Journal of Biochemistry, 103:544-546 (1998).

\* cited by examiner

Figure 2
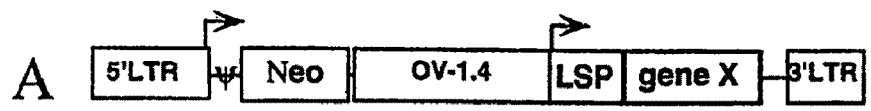
→ transcription start site
5' & 3' LTR: ALV long terminal repeats
Ψ virus packaging signal
Neo: neomycin-reistance gene
OV-1.4: ovalbumin -1.4 kb promoter
LSP: lysozyme signal peptide
gene X: gene or cDNA encoding an exogenous protein
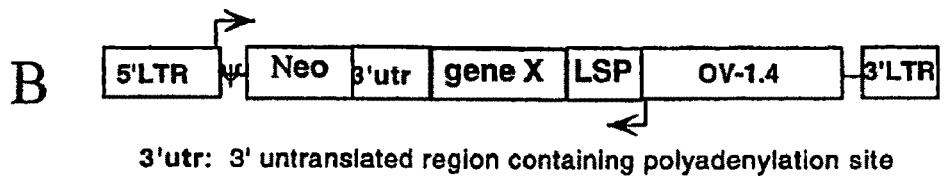
3'utr: 3' untranslated region containing polyadenylation site
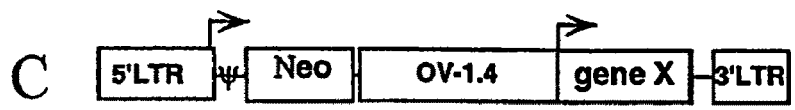
Same vector as A lacking LSP element
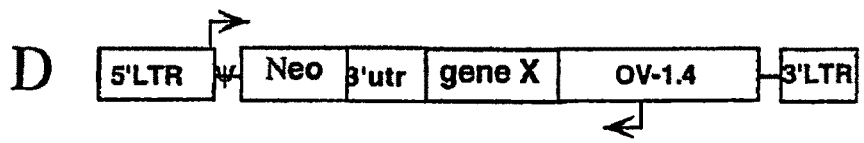
Same vector as B lacking LSP element

Figure 2E
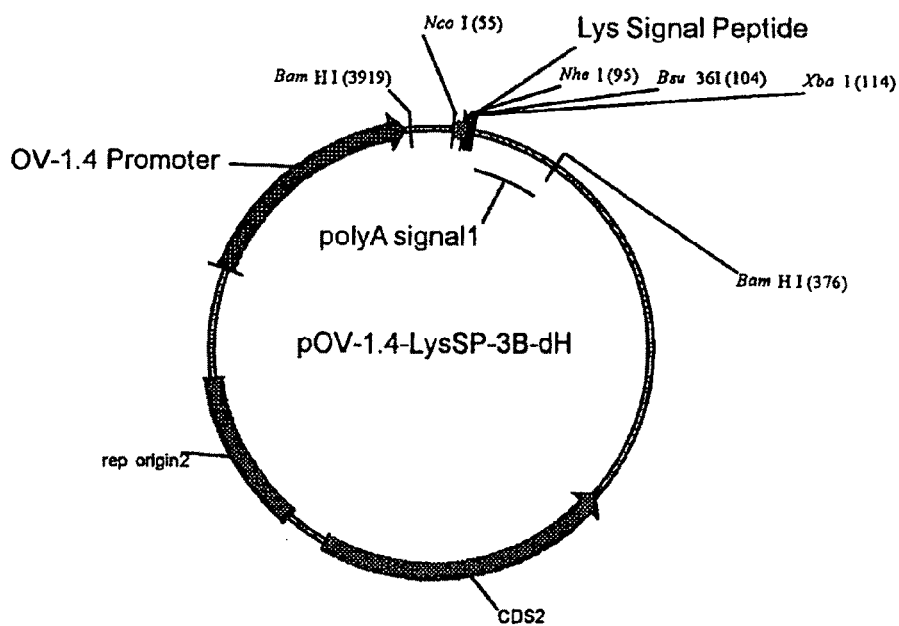
Lysozyme Signal Peptide
```
         M   G   S   L   L   I   L   V   L   C   F   L   P   L   A
        NcoI                                                    NheI
  51  CCACCATGGG GTCTTTGCTA ATCTTGGTGC TTTGCTTCCT GCCGCTAGCT
      GGTGGTACCC CAGAAACGAT TAGAACCACG AAACGAAGGA CGGCGATCGA
        A   L   G▼
       Bsu36I        XbaI                ▼ : Signal peptide cleavage site.
 101  GCCTTAGGGC CCTCTAGAG
      CGGAATCCCG GGAGATCTC
```
PCR Cloning of cDNA
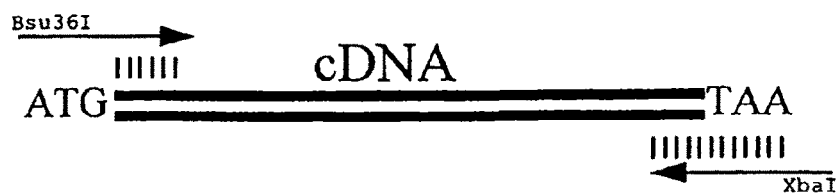

↱ transcription start site
5' & 3' LTR: ALV long terminal repeats
Ψ virus packaging signal
Neo: neomycin-reistance gene
OV - 1.4: ovalbumin -1.4 kb promoter
LSP: lysozyme signal peptide
gene X: gene or cDNA encoding an exogenous protein
gene Y: gene or cDNA encoding an exogenous protein
IRES: internal ribosome entry site

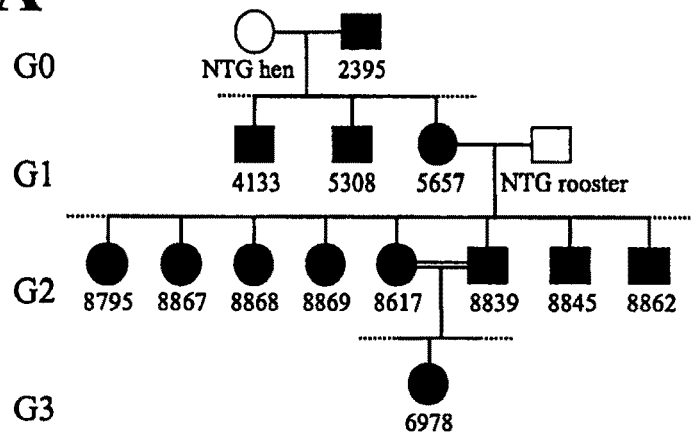
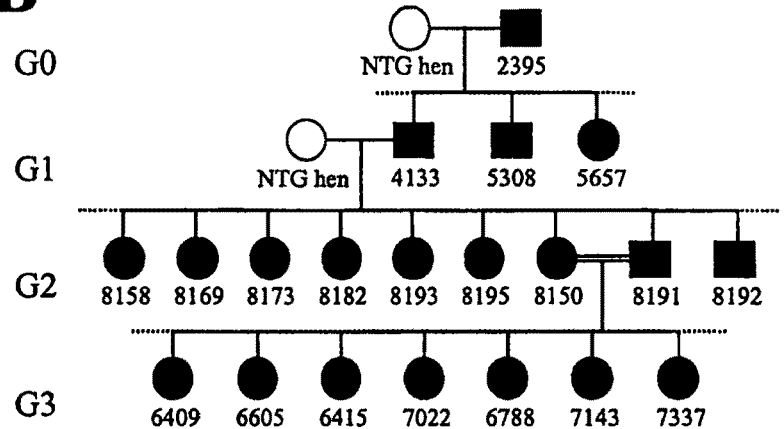
Figure 5

Figure 7
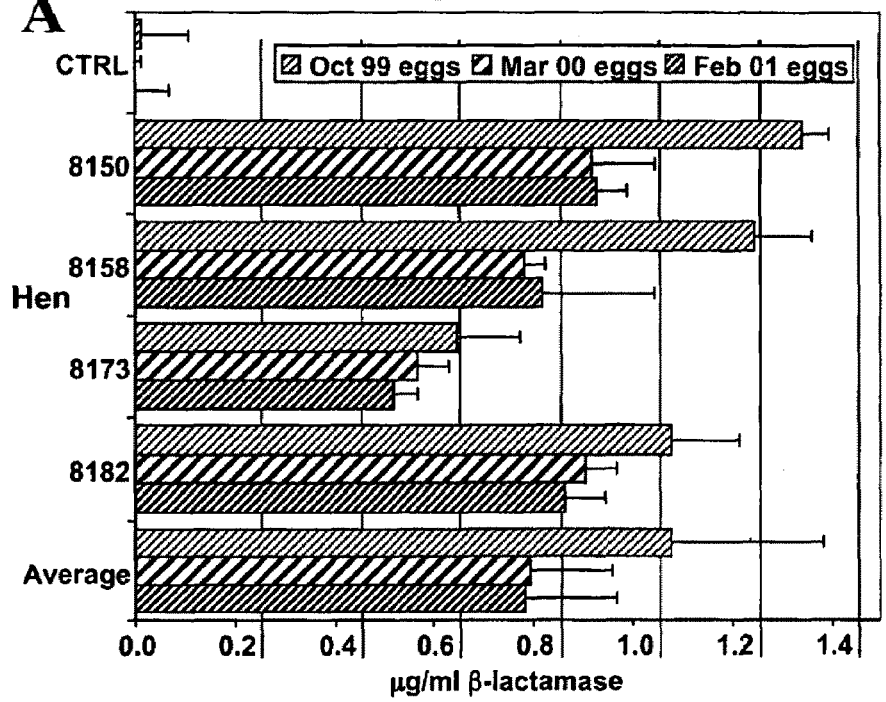
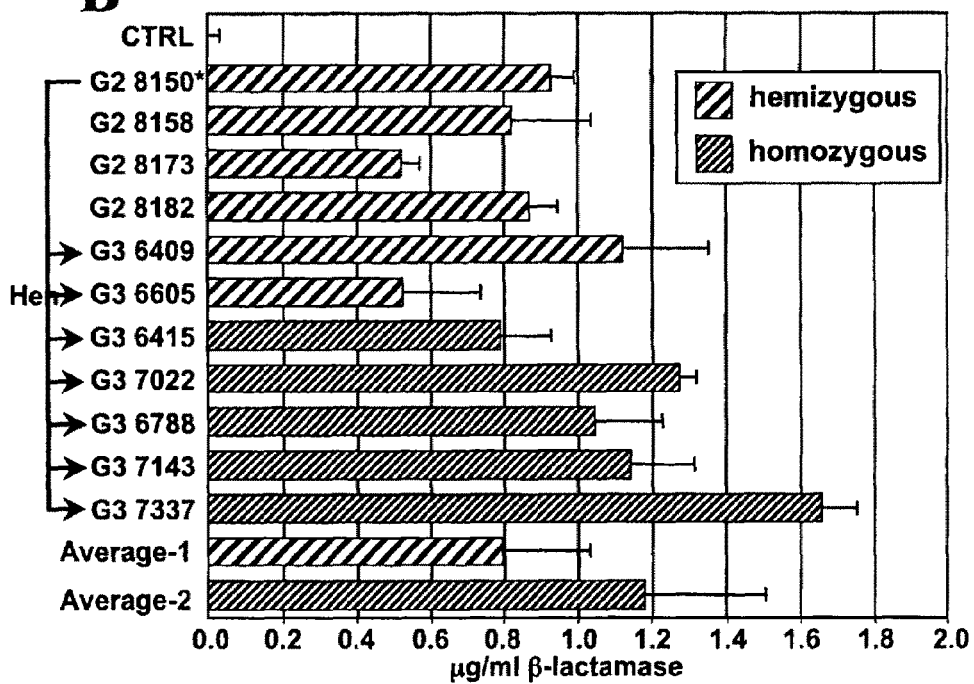

TGCGATCTGCCTCAGACCCACAGCCTGGGCAGCAGGAGGACCCTGATGCTGCTG
GCTCAGATGAGGAGAATCAGCCTGTTTAGCTGCCTGAAGGATAGGCACGATTTT
GGCTTTCCTCAAGAGGAGTTTGGCAACCAGTTTCAGAAGGCTGAGACCATCCCTG
TGCTGCACGAGATGATCCAGCAGATCTTTAACCTGTTTAGCACCAAGGATAGCAG
CGCTGCTTGGGATGAGACCCTGCTGGATAAGTTTTACACCGAGCTGTACCAGCAG
CTGAACGATCTGGAGGCTTGCGTGATCCAGGGCGTGGGCGTGACCGAGACCCCT
CTGATGAAGGAGGATAGCATCCTGGCTGTGAGGAAGTACTTTCAGAGGATCACC
CTGTACCTGAAGGAGAAGAAGTACAGCCCCTGCGCTTGGGAAGTCGTGAGGGCT
GAGATCATGAGGAGCTTTAGCCTGAGCACCAACCTGCAAGAGAGCTTGAGGTCT
AAGGAGTAA

B

CDLPQTHSLGSRRTLMLLAQMRRISLFSCLKDRHDFGFPQEEFGNQFQKAETIPVLHE
MIQQIFNLFSTKDSSAAWDETLLDKFYTELYQQLNDLEACVIQGVGVTETPLMKEDS
ILAVRKYFQRITLYLKEKKYSPCAWEVVRAEIMRSFSLSTNLQESLRSKE

ATGGGCGTGCACGAGTGCCCTGCTTGGCTGTGGCTGCTCTTGAGCCTGCTCAGCC
TGCCTCTGGGCCTGCCTGTGCTGGGCGCTCCTCCAAGGCTGATCTGCGATAGCAG
GGTGCTGGAGAGGTACCTGCTGGAGGCTAAGGAGGCTGAGAACATCACCACCGG
CTGCGCTGAGCACTGCAGCCTGAACGAGAACATCACCGTGCCTGATACCAAGGT
GAACTTTTACGCTTGGAAGAGGATGGAGGTGGGCCAGCAGGCTGTGGAGGTGTG
GCAGGGCCTGGCTCTGCTGAGCGAGGCTGTGCTGAGGGGCCAGGCTCTGCTGGT
GAACAGCTCTCAGCCTTGGGAGCCTCTGCAGCTGCACGTGGATAAGGCTGTGAG
CGGCCTGAGAAGCCTGACCACCCTGCTGAGGGCTCTGGGCGCTCAGAAGGAGGC
TATCAGCCCTCCAGATGCTGCAAGCGCTGCCCCTCTGAGGACCATCACCGCTGAT
ACCTTTAGGAAGCTGTTTAGGGTGTACAGCAACTTTCTGAGGGGCAAGCTGAAG
CTGTACACCGGCGAGGCTTGCAGGACCGGCGATAGG

B

MGVHECPAWLWLLLSLLSLPLGLPVLGAPPRLICDSRVLERYLLEAKEAENITTGCA
EHCSLNENITVPDTKVNFYAWKRMEVGQQAVEVWQGLALLSEAVLRGQALLVNSS
QPWEPLQLHVDKAVSGLRSLTTLLRALRAQKEAISPPDAASAAPLRTITADTFRKLFR
VYSNFLRGKLKLYTGEACRTGDR

Figure 13
MDOT Promoter

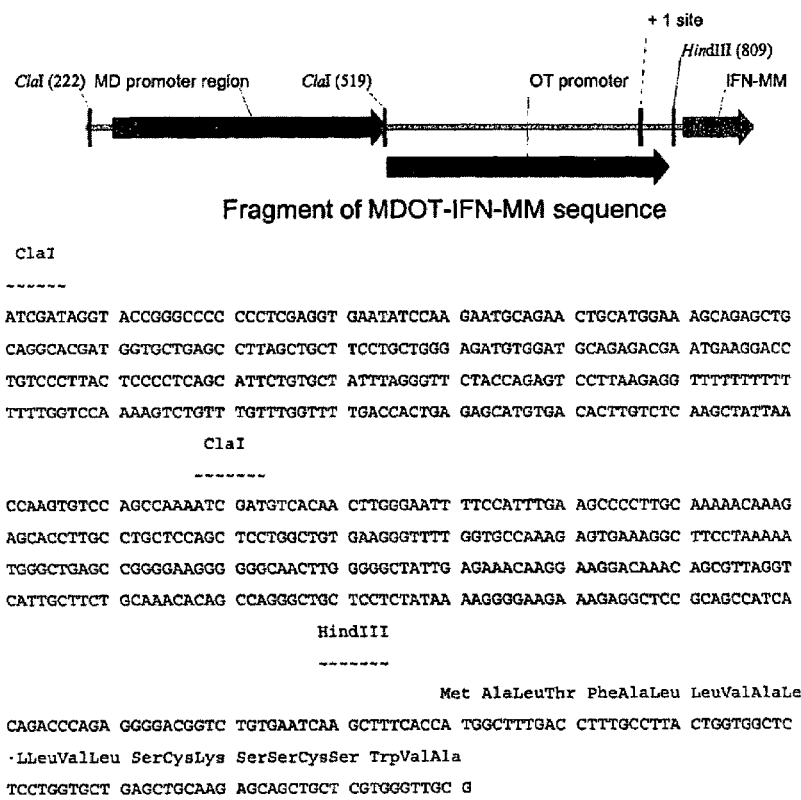

Fragment of MDOT-IFN-MM sequence

```
    ClaI
    ------
220 ATCGATAGGT ACCGGGCCCC CCCTCGAGGT GAATATCCAA GAATGCAGAA CTGCATGGAA AGCAGAGCTG
290 CAGGCACGAT GGTGCTGAGC CTTAGCTGCT TCCTGCTGGG AGATGTGGAT GCAGAGACGA ATGAAGGACC
360 TGTCCCTTAC TCCCCTCAGC ATTCTGTGCT ATTTAGGGTT CTACCAGAGT CCTTAAGAGG TTTTTTTTTT
430 TTTTGGTCCA AAAGTCTGTT TGTTTGGTTT TGACCACTGA GAGCATGTGA CACTTGTCTC AAGCTATTAA
                 ClaI
                 --------
500 CCAAGTGTCC AGCCAAAATC GATGTCACAA CTTGGGAATT TTCCATTTGA AGCCCCTTGC AAAAACAAAG
570 AGCACCTTGC CTGCTCCAGC TCCTGGCTGT GAAGGGTTTT GGTGCCAAAG AGTGAAAGGC TTCCTAAAAA
640 TGGGCTGAGC CGGGGAAGGG GGGCAACTTG GGGGCTATTG AGAAACAAGG AAGGACAAAC AGCGTTAGGT
710 CATTGCTTCT GCAAACACAG CCAGGGCTGC TCCTCTATAA AAGGGGAAGA AAGAGGCTCC GCAGCCATCA
                               HindIII
                               --------

Met AlaLeuThr PheAlaLeu LeuValAlaLeu·
780 CAGACCCAGA GGGGACGGTC TGTGAATCAA GCTTTCACCA TGGCTTTGAC CTTTGCCTTA CTGGTGGCTC
     ·LLeuValLeu SerCysLys SerSerCysSer TrpValAla
850 TCCTGGTGCT GAGCTGCAAG AGCAGCTGCT CGTGGGTTGC G
```

Figure 14
Summary of Major Egg White Proteins

| Gene | Expression | Amount in Albumin (%) | mg of Protein per Egg | MW kDa | Molar Concentr (mM) | Promoter Cloned: |
|---|---|---|---|---|---|---|
| ovalbumin | magnum | 63 | 2520 | 43 | 1.628 | yes |
| ovomucoid | magnum | 11 | 440 | 28 | 0.437 | 0.438 kb available |
| ovotransferrin | magnum liver | 12 | 480 | 80 | 0.167 | 1.1 kb available |
| lysozyme | magnum macrophages | 3.4 | 136 | 14 | 0.270 | yes |
| ovomucin | magnum | 3.5 / 2 | 140 / 80 | 700 / 700 | 0.006 / 0.003 | no |
| ovoinhibitor | magnum liver | 1.4 1 mg/ml in | 56 | 46.5 | 0.033 | gene sequence is known |

A.
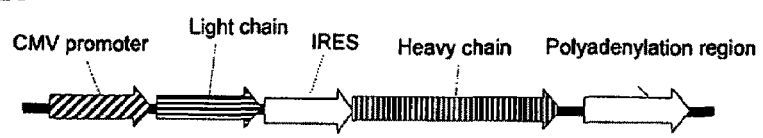
B.
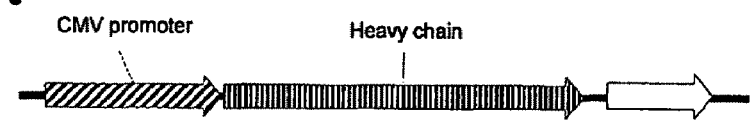
C.
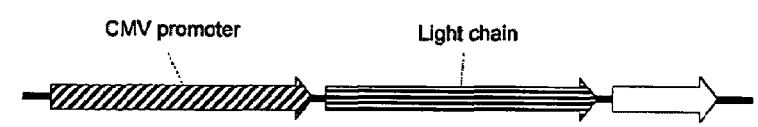
D.
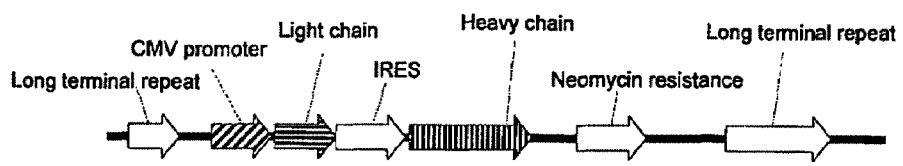
Figure 15

ATGGCTGGACCTGCCACCCAGAGCCCCATGAAGCTGATGGCCCTGCAGCTGC
TGCTGTGGCACAGTGCACTCTGGACAGTGCAGGAAGCCACCCCCCTGGGCCC
TGCCAGCTCCCTGCCCCAGAGCTTCCTGCTCAAGTGCTTAGAGCAAGTGAGG
AAGATCCAGGGCGATGGCGCAGCGCTCCAGGAGAAGCTGTGTGCCACCTACA
AGCTGTGCCACCCCGAGGAGCTGGTGCTGCTCGGACACTCTCTGGGCATCCC
CTGGGCTCCCCTGAGCAGCTGCCCCAGCCAGGCCCTGCAGCTGGCAGGCTGC
TTGAGCCAACTCCATAGCGGCCTTTTCCTCTACCAGGGGCTCCTGCAGGCCCT
GGAAGGGATCTCCCCCGAGTTGGGTCCCACCTTGGACACACTGCAGCTGGAC
GTCGCCGACTTTGCCACCACCATCTGGCAGCAGATGGAAGAACTGGGAATGG
CCCCTGCCCTGCAGCCCACCCAGGGTGCCATGCCGGCCTTCGCCTCTGCTTTC
CAGCGCCGGGCAGGAGGGGTCCTAGTTGCCTCCCATCTGCAGAGCTTCCTGG
AGGTGTCGTACCGCGTTCTACGCCACCTTGCCCAGCCC

FIG. 18 A

MAGPATQSPMKLMALQLLLWHSALWTVQEATPLGPASSLPQSFLLKCLEQVRKI
QGDGAALQEKLCATYKLCHPEELVLLGHSLGIPWAPLSSCPSQALQLAGCLSQL
HSGLFLYQGLLQALEGISPELGPTLDTLQLDVADFATTIWQQMEELGMAPALQPT
QGAMPAFASAFQRRAGGVLVASHLQSFLEVSYRVLRHLAQP

FIG. 18 B

TPLGPASSLPQSFLLKCLEQVRKIQGDGAALQEKLCATYKLCHPEELVLLGHSLGI
PWAPLSSCPSQALQLAGCLSQLHSGLFLYQGLLQALEGISPELGPTLDTLQLDVA
DFATTIWQQMEELGMAPALQPTQGAMPAFASAFQRRAGGVLVASHLQSFLEVS
YRVLRHLAQP

FIG. 18 C

GLYCOSYLATED G-CSF OBTAINED FROM A TRANSGENIC CHICKEN

RELATED APPLICATION INFORMATION

This application claims the benefit of U.S. provisional patent application Nos. 60/783,648, filed Mar. 17, 2006; and 60/840,291, filed Aug. 25, 2006, the disclosures of which are incorporated in their entirety herein by reference and is a continuation-in-part of U.S. patent application Ser. No. 11/370,555, filed Mar. 8, 2006, now U.S. Pat. No. 7,338,654, issued Mar. 4, 2008, the disclosure of which is incorporated in its entirety herein by reference, which is a continuation of U.S. patent application Ser. No. 10/351,196, filed Jan. 24, 2003, now U.S. Pat. No. 7,129,390, issued Oct. 31, 2006, the disclosure of which is incorporated in its entirety herein by reference, which is a continuation-in-part of U.S. application Ser. No. 09/173,864, filed Oct. 16, 1998, now U.S. Pat. No. 6,730,822, issued May 4, 2004, the disclosure of which is incorporated in its entirety herein by reference, which claims the benefit of U.S. provisional application No. 60/062,172, filed Oct. 16, 1997.

FIELD OF THE INVENTION

The present invention relates to the introduction of exogenous genetic material into avian cells and the expression of the exogenous genetic material in the avian cells. The invention particularly relates to transgenic avian species, including chicken, quail and turkey, and to avians which lay eggs containing exogenous proteins, for example pharmaceutical proteins.

BACKGROUND

Numerous natural and synthetic proteins are used in diagnostic and therapeutic applications; many others are in development or in clinical trials. Current methods of protein production include isolation from natural sources and recombinant production in bacterial and mammalian cells. Because of the complexity and high cost of these methods of protein production, however, efforts are underway to develop alternatives. For example, methods for producing exogenous proteins in the milk of pigs, sheep, goats, and cows have been reported. These approaches have certain limitations, including long generation times between founder and production transgenic herds, extensive husbandry and veterinary costs, and variable levels of expression because of position effects at the site of the transgene insertion in the genome. Proteins are also being produced using milling and malting processes from barley and rye. However, plant post-translational modifications differ from vertebrate post-translational modifications, which often has a critical effect on the function of the exogenous proteins such as pharmaceutical proteins.

Like tissue culture and mammary gland bioreactors, the avian oviduct can also potentially serve as a bioreactor. Successful methods of modifying avian genetic material such that high levels of exogenous proteins are secreted in the oviduct and packaged into eggs would allow inexpensive production of large amounts of protein. Several advantages of such an approach would be: a) short generation times (24 weeks) and rapid establishment of transgenic flocks via artificial insemination; b) readily scaled production by increasing flock sizes to meet production needs; c) post-translational modification of expressed proteins; 4) automated feeding and egg collection; d) naturally sterile egg-whites; and e) reduced processing costs due to the high concentration of protein in the egg white.

The avian reproductive system, including that of the chicken, is well described. The egg of the hen consists of several layers which are secreted upon the yolk during its passage through the oviduct. The production of an egg begins with formation of the large yolk in the ovary of the hen. The unfertilized oocyte is then positioned on top of the yolk sac. Upon ovulation or release of the yolk from the ovary, the oocyte passes into the infundibulum of the oviduct where it is fertilized if sperm are present. It then moves into the magnum of the oviduct which is lined with tubular gland cells. These cells secrete the egg-white proteins, including ovalbumin, lysozyme, ovomucoid, conalbumin, and ovomucin, into the lumen of the magnum where they are deposited onto the avian embryo and yolk.

The ovalbumin gene encodes a 45 kD protein that is specifically expressed in the tubular gland cells of the magnum of the oviduct (Beato Cell 56:335-344 (1989)). Ovalbumin is the most abundant egg white protein, comprising over 50 percent of the total protein produced by the tubular gland cells, or about 4 grams of protein per large Grade A egg (Gilbert, "Egg albumen and its formation" in Physiology and Biochemistry of the Domestic Fowl, Bell and Freeman, eds., Academic Press, London, N.Y., pp. 1291-1329). The ovalbumin gene and over 20 kb of each flanking region have been cloned and analyzed (Lai et al., Proc. Natl. Acad. Sci. USA 75:2205-2209 (1978); Gannon et al., Nature 278:428-424 (1979); Roop et al., Cell 19:63-68 (1980); and Royal et al., Nature 279:125-132 (1975)).

Much attention has been paid to the regulation of the ovalbumin gene. The gene responds to steroid hormones such as estrogen, glucocorticoids, and progesterone, which induce the accumulation of about 70,000 ovalbumin mRNA transcripts per tubular gland cell in immature chicks and 100,000 ovalbumin mRNA transcripts per tubular gland cell in the mature laying hen (Palmiter, J. Biol. Chem. 248:8260-8270 (1973); Palmiter, Cell 4:189-197 (1975)). DNAse hypersensitivity analysis and promoter-reporter gene assays in transfected tubular gland cells defined a 7.4 kb region as containing sequences required for ovalbumin gene expression. This 5' flanking region contains four DNAse I-hypersensitive sites centered at −0.25, −0.8, −3.2, and −6.0 kb from the transcription start site. These sites are called HS-I, -II, -III, and -IV, respectively. These regions reflect alterations in the chromatin structure and are specifically correlated with ovalbumin gene expression in oviduct cells (Kaye et al., EMBO 3:1137-1144 (1984)). Hypersensitivity of HS-II and -III are estrogen-induced, supporting a role for these regions in hormone-induction of ovalbumin gene expression.

HS-I and HS-II are both required for steroid induction of ovalbumin gene transcription, and a 1.4 kb portion of the 5' region that includes these elements is sufficient to drive steroid-dependent ovalbumin expression in explanted tubular gland cells (Sanders and McKnight, Biochemistry 27: 6550-6557 (1988)). HS-I is termed the negative-response element ("NRE") because it contains several negative regulatory elements which repress ovalbumin expression in the absence of hormones (Haekers et al., Mol. Endo. 9:1113-1126 (1995)). Protein factors bind these elements, including some factors only found in oviduct nuclei suggesting a role in tissue-specific expression. HS-II is termed the steroid-dependent response element ("SDRE") because it is required to promote steroid induction of transcription. It binds a protein or protein complex known as Chirp-I. Chirp-I is induced by estrogen and turns over rapidly in the presence of cyclohexamide (Dean et al., Mol. Cell. Biol. 16:2015-2024 (1996)). Experiments using an explanted tubular gland cell culture system defined an additional set of factors that bind SDRE in a steroid-dependent manner, including an NFκB-like factor (Nordstrom et al., J. Biol. Chem. 268:13193-13202 (1993); Schweers and Sanders, J. Biol. Chem. 266: 10490-10497 (1991)).

Less is known about the function of HS-III and -IV. HS-III contains a functional estrogen response element, and confers estrogen inducibility to either the ovalbumin proximal promoter or a heterologous promoter when co-transfected into HeLa cells with an estrogen receptor cDNA. These data imply that HS-III may play a functional role in the overall regulation of the ovalbumin gene. Little is known about the function of HS-IV, except that it does not contain a functional estrogen-response element (Kato et al., Cell 68: 731-742 (1992)).

There has been much interest in modifying eukaryotic genomes by introducing foreign genetic material and/or by disrupting specific genes. Certain eukaryotic cells may prove to be superior hosts for the production of exogenous eukaryotic proteins. The introduction of genes encoding certain proteins also allows for the creation of new phenotypes which could have increased economic value. In addition, some genetically-caused disease states may be cured by the introduction of a foreign gene that allows the genetically defective cells to express the protein that they can otherwise not produce. Finally, modification of animal genomes by insertion or removal of genetic material permits basic studies of gene function, and ultimately may permit the introduction of genes that could be used to cure disease states, or result in improved animal phenotypes.

Transgenesis has been accomplished in mammals by several different methods. First, in mammals including the mouse, pig, goat, sheep and cow, a transgene is microinjected into the pronucleus of a fertilized egg, which is then placed in the uterus of a foster mother where it gives rise to a founder animal carrying the transgene in its germline. The transgene is engineered to carry a promoter with specific regulatory sequences directing the expression of the foreign protein to a particular cell type. Since the transgene inserts randomly into the genome, position effects at the site of the transgene's insertion into the genome may variably cause decreased levels of transgene expression. This approach also requires characterization of the promoter such that sequences necessary to direct expression of the transgene in the desired cell type are defined and included in the transgene vector (Hogan et al. Manipulating the Mouse Embryo, Cold Spring Harbor Laboratory, NY (1988)).

A second method for effecting animal transgenesis is targeted gene disruption, in which a targeting vector containing sequences of the target gene flanking a selectable marker gene is introduced into embryonic stem ("ES") cells. By homologous recombination, the targeting vector replaces the target gene sequences at the chromosomal locus or inserts into interior sequences preventing expression of the target gene product. Clones of ES cells having the appropriately disrupted gene are selected and then injected into early stage blastocysts generating chimeric founder animals, some of which have the transgene in the germ line. In the case where the transgene deletes the target locus, it replaces the target locus with foreign DNA borne in the transgene vector, which consists of DNA encoding a selectable marker useful for detecting transfected ES cells in culture and may additionally contain DNA sequences encoding a foreign protein which is then inserted in place of the deleted gene such that the target gene promoter drives expression of the foreign gene (U.S. Pat. Nos. 5,464,764 and 5,487,992 (M. P. Capecchi and K. R. Thomas)). This approach suffers from the limitation that ES cells are unavailable in many mammals, including goats, cows, sheep and pigs. Furthermore, this method is not useful when the deleted gene is required for survival or proper development of the organism or cell type.

Recent developments in avian transgenesis have allowed the modification of avian genomes. Germ-line transgenic chickens may be produced by injecting replication-defective retrovirus into the subgerminal cavity of chick blastoderms in freshly laid eggs (U.S. Pat. No. 5,162,215; Bosselman et al., Science 243:533-534 (1989); Thoraval et al., Transgenic Research 4:369-36 (1995)). The retroviral nucleic acid carrying a foreign gene randomly inserts into a chromosome of the embryonic cells, generating transgenic animals, some of which have the transgene in their germ line. Use of insulator elements inserted at the 5' or 3' region of the fused gene construct to overcome position effects at the site of insertion has been described (Chim et al., Cell 74:504-514 (1993)).

In another approach, a transgene has been microinjected into the germinal disc of a fertilized egg to produce a stable transgenic founder avian that may pass the gene to the F1 generation (Love et al., Bio/Technology 12:60-63 (1994)). However, this method has several disadvantages. Hens must be sacrificed in order to collect the fertilized egg, the fraction of transgenic founders is low, and injected eggs require labor intensive in vitro culture in surrogate shells.

In another approach, blastodermal cells containing presumptive primordial germ cells ("PGCs") are excised from donor eggs, transfected with a transgene and introduced into the subgerminal cavity of recipient embryos. The transfected donor cells are incorporated into the recipient embryos generating transgenic embryos, some of which are expected to have the transgene in the germ line. The transgene inserts in random chromosomal sites by nonhomologous recombination. However, no transgenic founder avians have yet been generated by this method.

Lui, Poult. Sci. 68:999-1010 (1995), used a targeting vector containing flanking DNA sequences of the vitellogenin gene to delete part of the resident gene in chicken blastodermal cells in culture. However, it has not been demonstrated that these cells can contribute to the germ line and thus produce a transgenic embryo. In addition, this method is not useful when the deleted gene is required for survival or proper development of the organism or cell type.

Thus, it can be seen that there is a need for a method of introducing foreign DNA, operably linked to a suitable promoter, into the avian genome such that efficient expression of an exogenous gene can be achieved. Furthermore, there exists a need to create germ-line modified transgenic avians which express exogenous genes in their oviducts and secrete the expressed exogenous proteins into their eggs.

When interferon was discovered in 1957, it was hailed as a significant antiviral agent. In the late 1970s, interferon became associated with recombinant gene technology. Today, interferon is a symbol of the complexity of the biological processes of cancer and the value of endurance and persistence in tackling this complexity.

The abnormal genes that cause cancer comprise at least three types: firstly, there are the oncogenes, which, when altered, encourage the abnormal growth and division that characterize cancer. Secondly, there are the tumor suppressor genes, which, when altered, fail to control this abnormal growth and division. Thirdly, there are the DNA repair genes, which, when altered, fail to repair mutations that can lead to cancer. Researchers speculate that there are about 30 to 40 tumor suppressor genes in the body, each of which produces a protein. These proteins may be controlled by "master" tumor suppressor proteins such as Rb (for retinoblastoma, with which it was first associated) and p53 (associated with many different tumors). Evidence from the laboratory suggests that returning just one of these tumor suppressor genes to its normal function can appreciably reduce the aggressiveness of the malignancy.

Scientists became intrigued by interferon when it was discovered that interferon can inhibit cell growth. Further, interferon was found to have certain positive effects on the immune system. It is now considered analogous to a tumor suppressor protein: it inhibits the growth of cells, particularly malignant cells; it blocks the effects of many oncogenes and growth factors; and unlike other biological agents, it inhibits cell motility which is critical to the process of metastasis.

Intercellular communication is dependent on the proper functioning of all the structural components of the tissue through which the messages are conveyed: the matrix, the cell membrane, the cytoskeleton, and the cell itself. In cancer, the communication network between cells is disrupted. If the cytoskeleton is disrupted, the messages don't get through to the nucleus and the nucleus begins to function abnormally. Since the nucleus is the site where the oncogenes or tumor suppressor genes get switched on or off, this abnormal functioning can lead to malignancy. When this happens, the cells start growing irregularly and do not differentiate. They may also start to move and disrupt other cells. It is believed that interferon, probably in concert with other extracellular and cellular substances, restores the balance and homeostasis, making sure the messages get through properly. Interferon stops growth, stops motility, and enhances the ability of the cell, through adhesion molecules, to respond to its environment. It also corrects defects and injuries in the cytoskeleton. Interferon has been found to block angiogenesis, the initial step in the formation of new blood vessels that is essential to the growth of malignancies. Moreover, it blocks fibrosis, a response to injury that stimulates many different kinds of cells and promotes cell growth (Kathryn L. Hale, Oncolog, Interferon: The Evolution of a Biological Therapy, Taking a New Look at Cytokine Biology).

Interferon is produced by animal cells when they are invaded by viruses and is released into the bloodstream or intercellular fluid to induce healthy cells to manufacture an enzyme that counters the infection. For many years the supply of human interferon for research was limited by costly extraction techniques. In 1980, however, the protein became available in greater quantities through genetic engineering (i.e., recombinant forms of the protein). Scientists also determined that the body makes three distinct types of interferon, referred to as α-(alpha), β-(beta), and γ-(gamma) interferon. Interferons were first thought to be highly species-specific, but it is now known that individual interferons may have different ranges of activity in other species. Alpha interferon (α-IFN) has been approved for therapeutic use against hairy-cell leukemia and hepatitis C. α-IFN has also been found effective against chronic hepatitis B, a major cause of liver cancer and cirrhosis, as well as for treatment of genital warts and some rarer cancers of blood and bone marrow. Nasal sprays containing α-IFN provide some protection against colds caused by rhinoviruses. Human α-IFN belongs to a family of extracellular signaling proteins with antiviral, antiproliferating and immunomodulatory activities. IFN-α proteins are encoded by a multigene family which includes 13 genes clustered on the human chromosome 9. Most of the IFN-α genes are expressed at the mRNA level in leukocytes induced by Sendai virus. Further, it has been shown that at least nine different sub-types are also produced at the protein level. The biological significance of the expression of several similar IFN-α proteins is not known, however, it is believed that they have quantitatively distinct patterns of antiviral, growth inhibitory and killer-cell-stimulatory activities. Currently, two IFN-α variants, IFN-α 2a and IFN-α 2b, are mass produced in *Escherichia coli* by recombinant technology and marketed as drugs.

Unlike natural IFN-α, these recombinant IFN-α products have been shown to be immunogenic in some patients, which could be due to unnatural forms of IFN-α proteins. Thus, for the development of IFN-α drugs it is necessary to not only identify the IFN-α subtypes and variants expressed in normal human leukocytes, but also to characterize their possible post-translational modifications (Nyman et al. (1998) Eur. J. Biochem. 253:485-493).

Nyman et al. (supra) studied the glycosylation of natural human IFN-α. They found that two out of nine of the subtypes produced by leukocytes after a Sendai-virus induction were found to be glycosylated, namely IFN-α 14c and IFN-α 2b, which is consistent with earlier studies. IFN-α 14 is the only IFN-α subtype with potential N-glycosylation sites, Asn2 and Asn72, but only Asn72 is actually glycosylated. IFN-α 2 is O-glycosylated at Threonine 106 (Thr106). Interestingly, no other IFN-α subtype contains Thr at this position. In this study, Nyman et al. liberated and isolated the oligosaccharide chains and analyzed their structures by mass spectrometry and specific glycosidase digestions. Both IFN-α 2b and IFN-α 14c resolved into three peaks in reversed-phase high performance liquid chromatography (RP-HPLC). Electrospray ionization mass spectrometry (ESI-MS) analysis of IFN-α 2b fractions from RP-HPLC revealed differences in their molecular masses, suggesting that these represent different glycoforms. This was confirmed by masspectrometric analysis of the liberated O-glycans of each fraction. IFN-α 2b was estimated to contain about 20% of the core type-2 pentasaccharide, and about 50% of disialylated and 30% of monosialylated core type-1 glycans. Nyman et al.'s data agrees with previous partial characterization of IFN-α 2b glycosylation (Adolf et al. (1991) Biochem. J. 276:511-518). The role of glycosylation in IFN-α 14c and IFN-α 2b is not clearly established. According to Nyman et al. (supra), the carbohydrate chains are not essential for the biological activity, but glycosylation may have an effect on the pharmacokinetics and stability of the proteins.

There are at least 15 functional genes in the human genome that code for proteins of the IFN-α family. The amino acid sequence similarities are generally in the region of about 90%, thus, these molecules are closely related in structure. IFN-α proteins contain 166 amino acids (with the exception of IFN-α 2, which has 165 amino acids) and characteristically contain four conserved cysteine residues which form two disulfide bridges. IFN-α species are slightly acidic in character and lack a recognition site for asparagine-linked glycosylation. (with the exception of IFN-α 14 which does contain a recognition site for asparagine-linked glycosylation). Three variants of IFN-α 2, differing in their amino acids at positions 23 and 34, are known: IFN-α 2a (Lys-23, His-34); IFN-α 2b (Arg-23, His-34); and IFN-α 2c (Arg-23, Arg-34). It is believed that IFN-α 2a and IFN-α 2c are allelic variants of IFN-α 2b. See, Gewert et al (1993) J. Interferon Res. vol 13, p 227-231. The minor differences in amino acid content of the IFN-α 2 species is not expected to effect glycosylation of the interferons. That is glycosylation patterns are expected to be essentially the same for each of IFN-α 2a, 2b and 2c. Two other human IFN species, namely IFN-ω 1 and IFN-β are N-glycosylated and are more distantly related to IFN-α. IFN-α, -β and -ω, collectively referred to as class I IFNs, bind to the same high affinity cell membrane receptor (Adolf et al. (1991) Biochem. J. 276:511-518).

Adolf et al. (supra) used the specificity of a monoclonal antibody for the isolation of natural IFN-α 2 from human leukocyte IFN. They obtained a 95% pure protein through immunoaffinity chromatography which confirmed the expected antiviral activity of IFN-α 2. Analysis of natural IFN-α 2 by reverse-phase HPLC, showed that the natural protein can be resolved into two components, both more hydrophilic than *E. coli*-derived IFN-α 2. SDS/PAGE revealed that the protein is also heterogeneous in molecular mass, resulting in three bands, all of them with lower electrophoretic mobility than the equivalent *E. coli*-derived protein.

Adolf et al. (supra) also speculated that natural IFN-α 2 carries O-linked carbohydrate residues. Their hypothesis was confirmed by cleavage of the putative peptide-carbohydrate bond with alkali; the resulting protein was homogeneous and showed the same molecular mass as the recombinant protein. Further comparison of natural and recombinant proteins after proteolytic cleavage, followed by separation and analysis of the resulting fragments, allowed them to define a candidate glycopeptide. Sequence analysis of this peptide identified Thr-106 as the O-glycosylation site. A comparison of the amino acid sequences of all published IFN-α 2 species revealed that this threonine residue is unique to IFN-α 2. Glycine, isoleucine or glutamic acid are present at the corresponding position (107) in all other proteins.

Preparations of IFN-α 2 produced in *E. coli* are devoid of O-glycosylation and have been registered as drugs in many countries. However, the immunogenicity of therapeutically applied *E. coli*-derived IFN-α 2 might be affected by the lack of glycosylation. Studies have shown that four out of sixteen patients receiving recombinant human granulocyte-macrophage colony-stimulating factor produced in yeast developed antibodies to this protein. Interestingly, these antibodies were found to react with epitopes that in the endogenous granulocyte-macrophage colony-stimulating factor are protected by O-linked glycosylation, but which are exposed in the recombinant factor (Adolf et al., supra).

Similarly, induction of antibodies to recombinant *E. coli*-derived IFN-α 2 after prolonged treatment of patients has been described and it has been speculated that natural IFN-α 2 may be less immunogenic than the recombinant IFN-α 2 proteins (Galton et al. (1989) Lancet 2:572-573).

What is needed are improved methods of producing therapeutic or pharmaceutical proteins such as antibodies and cytokines including interferon, G-CSF and erythropoietin.

SUMMARY OF THE INVENTION

This invention provides vectors and methods for the stable introduction of exogenous nucleic acid sequences into the genome of avians in order to express the exogenous sequences to alter the phenotype of the avians or to produce desired proteins. In particular, transgenic avians are produced which express exogenous sequences in their oviducts and which deposit exogenous proteins, such as pharmaceutical proteins, into their eggs. Avian eggs that contain such exogenous proteins are encompassed by this invention. The present invention further provides novel forms of therapeutic proteins (e.g., human cytokines) including interferons, G-CSF, G-MCSF and erythropoietin which are efficiently expressed in the oviduct of transgenic avians and deposited into avian eggs.

One aspect of the present invention provides methods for producing exogenous proteins in specific tissues of avians. Exogenous proteins may be expressed in the oviduct, blood and/or other cells and tissues of the avian. In one embodiment, transgenes are introduced into embryonic blastodermal cells, for example, near stage X, to produce a transgenic avian, such that the protein of interest is expressed in the tubular gland cells of the magnum of the oviduct, secreted into the lumen, and deposited into the egg white of a hard shell egg. A transgenic avian so produced can carry the transgene in its germ line. The exogenous genes can therefore be transmitted to avians by both artificial introduction of the exogenous gene into avian embryonic cells, and by the transmission of the exogenous gene to the avian's offspring stably in a Mendelian fashion.

The present invention encompasses methods of producing exogenous protein in an avian oviduct. The methods may include as a first step of providing a vector that contains a coding sequence and a promoter operably linked to the coding sequence, so that the promoter can effect expression of the nucleic acid in the avian oviduct. Next, transgenic cells and/or tissues can be produced, wherein the vector is introduced into avian embryonic blastodermal cells, either freshly isolated, in culture, or in an embryo, so that the vector sequence is inserted, for example, randomly inserted into the avian genome. Finally, a mature transgenic avian which expresses the exogenous protein in its oviduct can be derived from the transgenic cells and/or tissue. This method can also be used to produce an avian egg which contains exogenous protein such as a pharmaceutical protein (e.g., a cytokine) when the exogenous protein that is expressed in the oviduct is also secreted into the oviduct lumen and deposited into the egg, for example, in the egg white of a hard shell egg.

In one aspect, the production of a transgenic bird by chromosomal insertion of a vector into its avian genome may optionally involve DNA transfection of embryonic blastodermal cells which are then injected into the subgerminal cavity beneath a recipient blastoderm. The vector used in such a method may have a promoter which is fused to an exogenous coding sequence and directs expression of the coding sequence in the tubular gland cells of the oviduct.

In another aspect of the invention, a random chromosomal insertion and the production of a transgenic avian is accomplished by transduction of embryonic blastodermal cells with replication-defective or replication-competent retroviral particles carrying the transgene genetic code between the 5' and 3' LTRs of the retroviral rector. For instance, an avian leukosis virus (ALV) retroviral vector or a murine leukemia virus (MLV) retroviral vector may be used which comprises a modified pNLB plasmid containing an exogenous gene that is inserted downstream of a segment of a promoter region. An RNA copy of the modified retroviral vector, packaged into viral particles, can be used to infect embryonic blastoderms which develop into transgenic avians. Alternatively, helper cells which produce the retroviral transducing particles are delivered to the embryonic blastoderm.

Another aspect of the invention provides a vector which includes a coding sequence and a promoter in operational and positional relationship such that the coding sequence is expressed in an avian oviduct. Such vectors include, but are not limited to, an avian leukosis virus (ALV) retroviral vector, a murine leukemia virus (MLV) retroviral vector, and a lentivirus vector. In addition, the vector may be a nucleic acid sequence which includes an LTR of an avian leukosis virus (ALV) retroviral vector, a murine leukemia virus (MLV) retroviral vector, or a lentivirus vector. The promoter is sufficient for effecting expression of the coding sequence in the avian oviduct. The coding sequence codes for an exogenous protein which is deposited into the egg white of a hard shell egg. As such, the coding sequence codes for exogenous proteins such as transgenic poultry derived proteins such as interferon-α 2b (TPD IFN-α 2b) and transgenic poultry derived erythropoietin (TPD EPO) and transgenic poultry derived granulocyte colony stimulating factor (TPD G-CSF). In one embodiment, vectors used in the methods of the invention contain a promoter which is particularly suited for expression of exogenous proteins in avians and their eggs. As such, expression of the exogenous coding sequence may occur in the oviduct and blood of the transgenic avian and in the egg white of its avian egg. The promoters include, but are not limited to, a cytomegalovirus (CMV) promoter, a MDOT promoter, a rous-sarcoma virus (RSV) promoter, a β-actin promoter (e.g., a chicken β-actin promoter) a murine leukemia virus (MLV) promoter, a mouse mammary tumor virus (MMTV) promoter, an ovalbumin promoter, a lysozyme promoter, a conalbumin promoter, an ovomucoid promoter, an ovomucin promoter, and an ovotransferrin promoter. Optionally, the promoter may be a segment of at least one promoter region, such as a segment of the ovalbumin-, lysozyme-, conalbumin-, ovomucoid-, ovomucin-, and ovotransferrin promoter region. In one embodiment, the promoter is a combination or a fusion of one or more promoters or a fusion of a portion of one or more promoters such as ovalbumin-, lysozyme-, conalbumin-, ovomucoid-, ovomucin-, and ovotransferrin promoters.

One aspect of the invention involves truncating the ovalbumin promoter and/or condensing the critical regulatory elements of the ovalbumin promoter so that it retains sequences required for expression in the tubular gland cells of the magnum of the oviduct, while being small enough that it can be readily incorporated into vectors. For instance, a segment of the ovalbumin promoter region may be used. This segment comprises the 5'-flanking region of the ovalbumin gene. The total length of the ovalbumin promoter segment may be from about 0.88 kb to about 7.4 kb in length, and is preferably from about 0.88 kb to about 1.4 kb in length. The segment preferably includes both the steroid-dependent regulatory element and the negative regulatory element of the ovalbumin gene. The segment optionally also includes residues from the 5'untranslated region (5'UTR) of the ovalbumin gene. Alternatively, the promoter may be a segment of the promoter region of the lysozyme-, conalbumin-, ovomucin-, ovomucoid- and ovotransferrin genes. An example of such a promoter is the synthetic MDOT promoter which is comprised of elements from the ovomucoid (MD) and ovotransferrin (OT) promoter.

In another aspect of the invention, the vectors integrated into the avian genome contain constitutive promoters which are operably linked to the exogenous coding sequence (e.g., cytomegalovirus (CMV) promoter, rous-sarcoma virus (RSV) promoter, and a murine leukemia virus (MLV) promoter. Alternatively, a non-constitutive promoter such as a mouse mammary tumor virus (MMTV) promoter may be used.

Other aspects of the invention provide for transgenic avians which carry a transgene in the genetic material of their germline tissue. More specifically, the transgene includes an exogenous gene and a promoter in operational and positional relationship to express the exogenous gene. The exogenous gene may be expressed in the avian oviduct and in the blood of the transgenic avian. The exogenous gene codes for exogenous proteins such as pharmaceutical proteins including cytokines such as TPD IFN-α (e.g., IFN-α 2) and TPD EPO and TPD G-CSF. The exogenous protein is deposited into the egg white of a hard shell egg.

Another aspect of the invention provides for an avian egg which contains protein exogenous to the avian species. Use of the invention allows for expression of exogenous proteins in oviduct cells with secretion of the proteins into the lumen of the oviduct magnum and deposition into the egg white of the avian egg. Proteins packaged into eggs may be present in quantities of up to one gram or more per egg. The exogenous protein includes, but is not limited to, TPD IFN-α 2 and TPD EPO and TPD G-CSF.

Still another aspect of the invention provides an isolated polynucleotide sequence comprising the optimized coding sequence of human interferon-α 2b (IFN-α 2b), i.e., recombinant transgenic poultry derived interferon-α 2b coding sequence which codes for transgenic poultry derived interferon-α 2b (TPD IFN-α 2b). The invention also encompasses an isolated protein comprising the polypeptide sequence of TPD IFN-α 2b, wherein the protein is O-glycosylated at Thr-106 with N-Acetyl-Galactosamine, Galactose, N-Acetyl-Glucosamine, Sialic acid, and combinations thereof.

The invention further contemplates a pharmaceutical composition comprising the polypeptide sequence of TPD IFN-α 2b, wherein the protein is O-glycosylated at Thr-106 with N-Acetyl-Galactosamine, Galactose, N-Acetyl-Glucosamine, Sialic acid, and combinations thereof.

One aspect of the invention provides for coding sequences for exogenous proteins produced as disclosed herein wherein the coding sequence is codon optimized for expression in an avian, for example, in a chicken. Codon optimization may be determined from the codon usage of at least one, and preferably more than one, protein expressed in an avian cell (e.g., a chicken cell). For example, the codon usage may be determined from the nucleic acid sequences encoding the proteins ovalbumin, lysozyme, ovomucin and ovotransferrin of chicken. For example, the DNA coding sequence for the exogenous protein may be codon optimized using the BACK-TRANSLATE® program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins.

One aspect of the invention provides an isolated polynucleotide sequence comprising the optimized coding sequence of human erythropoietin (EPO), i.e., recombinant transgenic poultry derived erythropoietin coding sequence which codes for transgenic poultry derived erythropoietin (TPD EPO).

Another aspect of the invention provides for a vector comprising a first and second coding sequence and a promoter in operational and positional relationship to the first and second coding sequence to express the first and second coding sequence in an avian oviduct. In this aspect, the vector may include an internal ribosome entry site (IRES) element positioned between the first and second coding sequence, wherein the first coding sequence codes for protein X and the second coding sequence codes for protein Y, and wherein one or both of protein X and protein Y are deposited into the egg (e.g., egg white) of a hard shell egg.

For example, protein X may be a light chain (LC) of a monoclonal antibody and protein Y may be a heavy chain (HC) of a monoclonal antibody. Alternatively, the protein encoded by the second coding sequence (e.g., enzyme) may be capable of providing post-translational modification of the protein encoded by the first coding sequence. The vector optionally includes additional coding sequences and additional IRES elements, such that each coding sequence in the vector is separated from another coding sequence by an IRES element. Other examples of employing an IRES which are contemplated for use in the present invention are disclosed in, for example, U.S. patent application Ser. No. 11/047,184, filed Jan. 31, 2005, the disclosure of which is incorporated in its entirety herein by reference.

The invention also contemplates methods of producing an avian egg which contains proteins such as pharmaceutical proteins including monoclonal antibodies, enzymes and other proteins. Such methods may include providing a vector with a promoter, coding sequences, and at least one IRES element; creating transgenic cells or tissue by introducing the vector into avian embryonic blastodermal cells, wherein the vector sequence is randomly inserted into the avian genome; and deriving a mature transgenic avian from the transgenic cells or tissue. The transgenic avian so derived may express the coding sequences in its oviduct, and the resulting protein secreted into the oviduct lumen, so that the protein is deposited into the egg white of a hard shell egg. In addition, the invention includes progeny of the transgenic avians which produce eggs containing the recombinant protein. Typically, the progeny will either contain the transgene in essentially all the cells of the bird or none of the cells of the progeny bird will contain the transgene.

One important aspect of the present invention relates to avian hard shell eggs (e.g., chicken hard shell eggs) which contain an exogenous peptide or protein including, but not limited to, a pharmaceutical protein. The exogenous peptide or protein may be encoded by a transgene of a transgenic avian. In one embodiment, the exogenous peptide or protein (e.g., pharmaceutical protein) is glycosylated. The protein may be present in any useful amount. In one embodiment, the protein is present in an amount in a range of between about 0.01 µg per hard-shell egg and about 1 gram per hard-shell egg. In another embodiment, the protein is present in an amount in a range of between about 1 µg per hard-shell egg and about 1 gram per hard-shell egg. For example, the protein may be present in an amount in a range of between about 10 µg per hard-shell egg and about 1 gram per hard-shell egg (e.g., a range of between about 10 µg per hard-shell egg and about 400 milligrams per hard-shell egg).

In one embodiment, the exogenous protein, for example, the exogenous pharmaceutical protein, is present in the egg white of the egg. In one embodiment, the protein is present in an amount in a range of between about 1 ng per milliliter of egg white and about 0.2 gram per milliliter of egg white. For example, the protein may be present in an amount in a range of between about 0.1 µg per milliliter of egg white and about 0.2 gram per milliliter of egg white (e.g., the protein may be present in an amount in a range of between about 1 µg per milliliter of egg white and about 100 milligrams per milliliter of egg white. In one embodiment, the protein is present in an amount in a range of between about 1 µg per milliliter of egg white and about 50 milligrams per milliliter of egg white. For example, the protein may be present in an amount in a range of about 1 µg per milliliter of egg white and about 10 milligrams per milliliter of egg white (e.g., the protein may be present in an amount in a range of between about 1 µg per milliliter of egg white and about 1 milligrams per milliliter of egg white).

The invention contemplates the production of hard shell eggs containing any useful protein including one or more pharmaceutical proteins. Such proteins include, but are not limited to, hormones, immunoglobulins or portions of immunoglobulins, cytokines (e.g., GM-CSF, G-CSF, erythropoietin and interferon) and CTLA4. The invention also includes the production of hard shell eggs containing fusion proteins including, but not limited to, immunoglobulins or portions of immunoglobulins fused to certain useful peptide sequences. In one embodiment, the invention provides for the production of hard shell eggs containing an antibody Fc fragment. For example, the eggs may contain an Fc-CTLA4 fusion protein in accordance with the invention.

The avians developed from the blastodermal cells into which the vector has been introduced are the G0 generation and are referred to as "founders". Founder birds are typically chimeric for each inserted transgene. That is, only some of the cells of the G0 transgenic bird contain the transgene(s). The G0 generation typically is also hemizygous for the transgene(s). The G0 generation may be bred to non-transgenic animals to give rise to G1 transgenic offspring which are also hemizygous for the transgene and contain the transgene(s) in essentially all of the bird's cells. The G1 hemizygous offspring may be bred to non-transgenic animals giving rise to G2 hemizygous offspring or may be bred together to give rise to G2 offspring homozygous for the transgene. Substantially all of the cells of birds which are positive for the transgene that are derived from G1 offspring will contain the transgene(s). In one embodiment, hemizygotic G2 offspring from the same line can be bred to produce G3 offspring homozygous for the transgene. In one embodiment, hemizygous G0 animals are bred together to give rise to homozygous G1 offspring containing two copies of the transgene(s) in each cell of the animal. These are merely examples of certain useful breeding schemes and the present invention contemplates the employment of any useful breeding scheme such as those known to individuals of ordinary skill in the art.

One aspect of the invention is directed to compositions which contain proteins produced in accordance with the invention that have a poultry derived glycosylation pattern, such as a chicken derived glycosylation pattern. For example, the invention includes pharmaceutical proteins having a poultry derived glycosylation pattern such as one or more of the glycosylation patterns disclosed herein. The invention also includes human proteins having a poultry derived glycosylation pattern such as one or more of the glycosylation patterns disclosed herein.

In one aspect, the invention includes G-CSF wherein the G-CSF has a poultry derived glycosylation pattern, i.e., a transgenic poultry derived G-CSF or TPD G-CSF. In one embodiment, the glycosylation pattern is other than that of G-CSF produced in a human cell and/or in a CHO cell. That is, the compositions have a G-CSF molecule with a poultry derived carbohydrate chain (i.e., glycosylation structure) and that carbohydrate chain or glycosylation structure is not found on G-CSF obtained from human cells and/or CHO cells. However, the composition may also include G-CSF molecules that have glycosylation structures that are the same as that found on G-CSF obtained from CHO cells and/or human cells. Glycosylation of human G-CSF produced in CHO cells is disclosed in Holloway, C. J., European J. of Cancer (1994) vol 30A, pS2-S6, the disclosure of which is incorporated in its entirety herein by reference; in Oheda et al (1988) J. Biochem., v 103, p 544-546, the disclosure of which is incorporated in its entirety herein by reference and in Andersen et al (1994) Glycobiology, vol 4, p 459-467, the disclosure of which is incorporated in its entirety herein by reference. It appears that structures such as A and G shown in Example 20 may be the same or similar to glycosylation structures reported for G-CSF produced in CHO cells. In one embodiment, the glycosylation pattern of the TPD G-CSF is other than that of G-CSF produced in mammalian cell.

In one embodiment, the invention provides for the G-CSF to be isolated. That is, the G-CSF contained in the composition may be an isolated G-CSF. For example, the G-CSF may be isolated from egg white. The isolated G-CSF may be G-CSF molecules having differing glycosylation structures among the G-CSF molecules or the isolated G-CSF may be an isolated individual species of G-CSF molecules having only one particular glycosylation structure among the species of G-CSF molecules.

In one embodiment, the G-CSF of a composition of the invention is present in a hard shell egg. For example, the G-CSF may be present in the egg white of a hard shell egg laid by a transgenic avian of the invention. That is, in one embodiment, the invention is directed to avian (e.g., chicken) egg white containing G-CSF of the invention. In one embodiment, the G-CSF is present in the egg white in an amount in excess of about 1 microgram per ml of egg white. For example, the G-CSF can be present in an amount greater that about 2 micrograms per ml of egg white (e.g., present in an amount of about 2 micrograms to about 200 micrograms per ml of egg white).

In one particular aspect of the invention, the G-CSF is glycosylated in an oviduct cell of the avian, e.g., glycosylated in an oviduct cell of a chicken. For example, the G-CSF can be produced and glycosylated in an oviduct cell. In one embodiment, the G-CSF is glycosylated in a tubular gland cell (e.g., the G-CSF is produced and glycosylated in a tubular gland cell).

The G-CSF is believed to be glycosylated at threonine 133. However, the invention is not limited to glycosylation at any particular site on a G-CSF molecule.

Typically, the G-CSF of the invention is human G-CSF. In one embodiment, the mature G-CSF has the amino acid sequence of FIG. 18 C.

In one embodiment, compositions of the invention include G-CSF molecules glycosylated with:

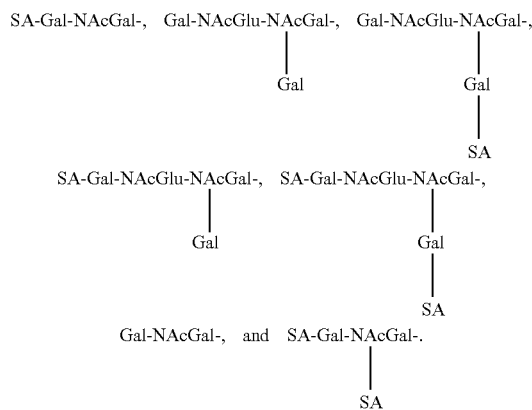

The invention is also specifically directed to compositions containing G-CSF molecules that have one of these particular glycosylation structures. Such compositions may also include one or more G-CSF molecules having one or more other glycosylation structures.

That is, in one embodiment, the invention is specifically directed to compositions containing G-CSF molecules that have:

and to compositions containing G-CSF molecules that have:

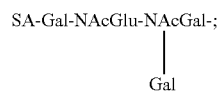

and to compositions containing G-CSF molecules that have:

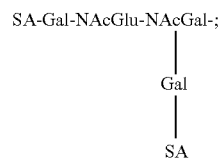

and to compositions containing G-CSF molecules that have:
SA-Gal-NAcGal-;

and to compositions containing G-CSF molecules that have:

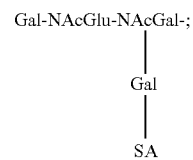

and to compositions containing G-CSF molecules that have:

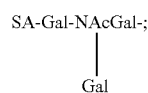

and to compositions containing G-CSF molecules that have:
Gal-NAcGal-, wherein Gal=Galactose,
NAcGal=N-Acetyl-Galactosamine,
NAcGlu=N-Acetyl-Glucosamine, and
SA=Sialic Acid.

The invention is also directed to methods of increasing white blood cell count in a patient which include administering to a patient a therapeutically effective amount of TPD G-CSF. Typically, the therapeutically effective amount is an amount of TPD G-CSF that increases the white blood cell count in a patient by a desired amount.

Any useful combination of features described herein is included within the scope of the present invention provided that the features included in any such combination are not mutually inconsistent as will be apparent from the context, this specification, and the knowledge of one of ordinary skill in the art.

Additional objects and aspects of the present invention will become more apparent upon review of the detailed description set forth below when taken in conjunction with the accompanying figures, which are briefly described as follows.

BRIEF DESCRIPTION OF THE DRAWINGS

FIGS. 2A, 2B, 2C and 2D illustrate retroviral vectors of the invention comprising an ovalbumin promoter and a coding sequence, gene X, encoding an exogenous protein X. X represents any exogenous gene or exogenous protein of interest.

FIG. 2E illustrates a method of amplifying an exogenous gene for insertion into the vectors of 2A and 2B.

In FIG. 4A the concentration of bioactive lactamase in the serum of G0 chickens transduced with the NLB-CMV-BL transgene was measured at 8 month post-hatch. The generation, sex and wing band numbers are indicated. Lactamase serum concentrations were measured for G1 transgenic chickens at 6 to 7 months post-hatch. Arrows indicate G1 chickens bred from rooster 2395. In FIG. 4B the lactamase serum concentration was measured for G1 and G2 transgenic chickens. Arrows indicate G2s bred from hen 5657 or rooster 4133. Samples from chickens 4133, 5308, and 5657 are the same as those in FIG. 4A. Samples from G2 birds bred from 5657 were collected at 3 to 60 days post-hatch. Samples from G2 birds bred from 4133 were collected at 3 month post-hatch.

FIG. 5 shows the pedigree of chickens containing the transgenic loci harbored by hen 5657 (FIG. 5A) or rooster 4133 (FIG. 5B). 2395 was a rooster that carried multiple transgenic loci. 2395 was bred to a non-transgenic hen, yielding 3 offspring each carrying the transgene in a unique position of the chicken genome. For simplicity, transgenic progeny for which expression data were not shown as well as non-transgenic progeny were omitted from the pedigree. Band numbers are indicated by the following symbols: ○ hen; □ rooster; ● hen carrying the NLB-CMV-BL transgene; ■ rooster carrying the NLB-CMV-BL transgene.

In FIG. 6A egg white from hen 5657 and her transgenic offspring were assayed for active lactamase. The control is from untreated hens and clutchmate is a non-transgenic G2 bred from hen 5657. Eggs were collected in March 2000. Arrows indicate G2s bred from hen 5657. In FIG. 6B egg white samples from G2 transgenic hens carrying one copy of the transgene (hemizygous) were compared with that of G3 hen 6978 which harbored two copies (homozygous). Eggs were collected in February 2001. The generation and wing band numbers are indicated to the left.

FIG. 7 shows β-lactamase (lactamase) in the eggs of G2 and G3 hens bred from rooster 4133. In FIG. 7A egg whites from four representative hemizygous transgenic hens bred from rooster 4133 were assayed for active lactamase. Eggs were collected in October 1999, March 2000 and February 2001 and a minimum of 4 eggs per hen were assayed one month after each set was collected. The control represents egg white from untreated hens. Band numbers are indicated to the left. The average of the 4 hens for each period is calculated. In FIG. 7B egg white from hemizygous G2 transgenic hens were compared with that of hemizygous and homozygous transgenic G3 hens. The eggs were collected in February 2001. The generation and transgene copy number are displayed in the data bar for each hen. The average concentration for hens carrying one or two copies is at the bottom of the chart.

FIG. 11A depicts the synthetic nucleic acid sequence (cDNA, residues 1-498) of optimized human interferon-α 2b (IFN-α 2b), i.e., recombinant TPD IFN-α 2b (SEQ ID NO: 1). FIG. 11B depicts the synthetic amino acid sequence (residues 1-165) of transgenic poultry derived interferon-α 2b (TPD IFN-α 2b) (SEQ ID NO: 2).

FIG. 12A depicts the synthetic nucleic acid sequence (cDNA, residues 1-579) of optimized human erythropoietin (EPO) i.e., recombinant TPD EPO (SEQ ID NO: 3). FIG. 12B depicts the synthetic amino acid sequence (residues 1-193) of transgenic poultry derived erythropoietin (TPD EPO) (SEQ ID NO: 4). (For natural human EPO see also NCBI Accession Number NP 000790).

FIG. 13 shows the synthetic MDOT promoter linked to the IFN-MM CDS. The MDOT promoter contains elements from the chicken ovomucoid gene (ovomucoid promoter) ranging from −435 to −166 bp (see NCBI Accession Number J00894) and the chicken conalbumin gene (ovotransferrin promoter) ranging from −251 to +29 bp (see NCBI Accession Numbers Y00497, M11862 and X01205).

FIG. 14 provides a summary of the major egg white proteins.

FIGS. 15A and 15D show the pCMV-LC-emcvIRES-HC vector, wherein the light chain (LC) and heavy chain (HC) of a human monoclonal antibody were expressed from this single vector by placement of an IRES from the encephalomyocarditis virus (EMCV) in order to test for expression of monoclonal antibodies. In comparison, FIGS. 15B and 15C show the separate vectors pCMV-HC and pCMV-LC, respectively, wherein these vectors were also used to test for expression of monoclonal antibodies.

FIG. 18A (SEQ ID NO: 39) shows the nucleotide sequence encoding the amino acid sequence of FIG. 18B. FIG. 18 B (SEQ ID NO: 40), which corresponds to NCBI Accession NP 7577373, shows the amino acid sequence of G-CSF including the natural signal sequence which is cleaved away to form the mature G-CSF during cellular secretion. FIG. 18C (SEQ ID NO: 41) shows the amino acid sequence of the mature G-CSF protein produced in accordance with the present invention.

DETAILED DESCRIPTION

Figure 1:
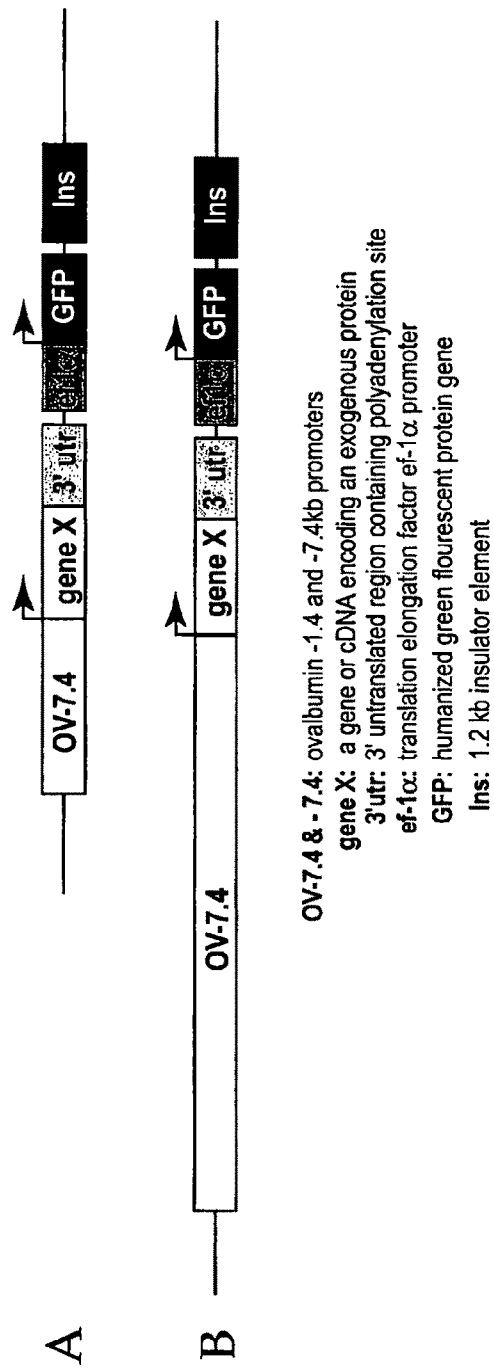
FIGS. 1A and 1B illustrate ovalbumin promoter expression vectors comprising ovalbumin promoter segments and a coding sequence, gene X, which encodes an exogenous protein X. X represents any exogenous gene or exogenous protein of interest.

Certain definitions are set forth herein to illustrate and define the meaning and scope of the various terms used to describe the invention herein.

A "nucleic acid or polynucleotide sequence" includes, but is not limited to, eukaryotic mRNA, cDNA, genomic DNA, and synthetic DNA and RNA sequences, comprising the natural nucleoside bases adenine, guanine, cytosine, thymidine, and uracil. The term also encompasses sequences having one or more modified bases.

"Therapeutic proteins" or "pharmaceutical proteins" include an amino acid sequence which in whole or in part makes up a drug.

A "coding sequence" or "open reading frame" refers to a polynucleotide or nucleic acid sequence which can be transcribed and translated (in the case of DNA) or translated (in the case of mRNA) into a polypeptide in vitro or in vivo when placed under the control of appropriate regulatory sequences. The boundaries of the coding sequence are determined by a translation start codon at the 5' (amino) terminus and a translation stop codon at the 3' (carboxy) terminus. A transcription termination sequence will usually be located 3' to the coding sequence. A coding sequence may be flanked on the 5' and/or 3' ends by untranslated regions.

"Exon" refers to that part of a gene which, when transcribed into a nuclear transcript, is "expressed" in the cytoplasmic mRNA after removal of the introns or intervening sequences by nuclear splicing.

Nucleic acid "control sequences" or "regulatory sequences" refer to promoter sequences, translational start and stop codons, ribosome binding sites, polyadenylation signals, transcription termination sequences, upstream regulatory domains, enhancers, and the like, as necessary and sufficient for the transcription and translation of a given coding sequence in a defined host cell. Examples of control sequences suitable for eukaryotic cells are promoters, polyadenylation signals, and enhancers. All of these control sequences need not be present in a recombinant vector so long as those necessary and sufficient for the transcription and translation of the desired gene are present.

"Operably or operatively linked" refers to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences, denote sequences that are not normally associated with a region of a recombinant construct or with a particular chromosomal locus, and/or are not normally associated with a particular cell. Thus, an "exogenous" region of a nucleic acid construct is an identifiable segment of nucleic acid within or attached to another nucleic acid molecule that is not found in association with the other molecule in nature. For example, an exogenous region of a construct could include a coding sequence flanked by sequences not found in association with the coding sequence in nature. Another example of an exogenous coding sequence is a construct where the coding sequence itself is not found in nature (e.g., synthetic sequences having codons different from the native gene). Similarly, a host cell transformed with a construct or nucleic acid which is not normally present in the host cell would be considered exogenous for purposes of this invention.

"Exogenous protein" as used herein refers to a protein not naturally present in a particular tissue or cell, a protein that is the expression product of an exogenous expression construct or transgene, or a protein not naturally present in a given quantity in a particular tissue or cell. A protein that is exogenous to an egg is a protein that is not normally found in the egg. For example, a protein exogenous to an egg may be a protein that is present in the egg as a result of the expression of a coding sequence present in a transgene of the animal laying the egg.

"Endogenous gene" refers to a naturally occurring gene or fragment thereof normally associated with a particular cell.

The expression products described herein may consist of proteinaceous material having a defined chemical structure. However, the precise structure depends on a number of factors, particularly chemical modifications common to proteins. For example, since all proteins contain ionizable amino and carboxyl groups, the protein may be obtained in acidic or basic salt form, or in neutral form. The primary amino acid sequence may be derivatized using sugar molecules (glycosylation) or by other chemical derivatizations involving covalent or ionic attachment with, for example, lipids, phosphate, acetyl groups and the like, often occurring through association with saccharides. These modifications may occur in vitro or in vivo, the latter being performed by a host cell through post-translational processing systems. Such modifications may increase or decrease the biological activity of the molecule, and such chemically modified molecules are also intended to come within the scope of the invention.

Alternative methods of cloning, amplification, expression, and purification will be apparent to the skilled artisan. Representative methods are disclosed in Sambrook, Fritsch, and Maniatis, Molecular Cloning, a Laboratory Manual, 2nd Ed., Cold Spring Harbor Laboratory (1989).

"Vector" means a polynucleotide comprised of single strand, double strand, circular, or supercoiled DNA or RNA. A typical vector may be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements may be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An intron optionally may be included in the construct, for example, 5' to the coding sequence. A vector is constructed so that the particular coding sequence is located in the vector with the appropriate regulatory sequences, the positioning and orientation of the coding sequence with respect to the control sequences being such that the coding sequence is transcribed under the "control" of the control or regulatory sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

A "promoter" is a site on the DNA to which RNA polymerase binds to initiate transcription of a gene. In some embodiments the promoter will be modified by the addition or deletion of sequences, or replaced with alternative sequences, including natural and synthetic sequences as well as sequences which may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box. Enhancer elements can also stimulate transcription from linked promoters, but many function exclusively in a particular cell type. Many enhancer/promoter elements derived from viruses, e.g., the SV40 promoter, the cytomegalovirus (CMV) promoter, the rous-sarcoma virus (RSV) promoter, and the murine leukemia virus (MLV) promoter are all active in a wide array of cell types, and are termed "ubiquitous". Alternatively, non-constitutive promoters such as the mouse mammary tumor virus (MMTV) promoter may also be used in the present invention. The nucleic acid sequence inserted in the cloning site may have any open reading frame encoding a polypeptide of interest, with the proviso that where the coding sequence encodes a polypeptide of interest, it should lack cryptic splice sites which can block production of appropriate mRNA molecules and/or produce aberrantly spliced or abnormal mRNA molecules.

The term "poultry derived" refers to a composition or substance produced by or obtained from poultry. "Poultry" refers to birds that can be kept as livestock, including but not limited to, chickens, duck, turkey, quail and ratites. For example, "poultry derived" may refer to chicken derived, turkey derived and/or quail derived.

A "marker gene" is a gene which encodes a protein that allows for identification and isolation of correctly transfected cells. Suitable marker sequences include, but are not limited to green, yellow, and blue fluorescent protein genes (GFP, YFP, and BFP, respectively). Other suitable markers include thymidine kinase (tk), dihydrofolate reductase (DHFR), and aminoglycoside phosphotransferase (APH) genes. The latter imparts resistance to the aminoglycoside antibiotics, such as kanamycin, neomycin, and geneticin. These, and other marker genes such as those encoding chloramphenicol acetyltransferase (CAT), β-lactamase, β-galactosidase (β-gal), may be incorporated into the primary nucleic acid cassette along with the gene expressing the desired protein, or the selection markers may be contained on separate vectors and cotransfected.

A "reporter gene" is a marker gene that "reports" its activity in a cell by the presence of the protein that it encodes.

A "retroviral particle", "transducing particle", or "transduction particle" refers to a replication-defective or replication-competent virus capable of transducing non-viral DNA or RNA into a cell.

The terms "transformation", "transduction" and "transfection" all denote the introduction of a polynucleotide into an avian blastodermal cell. "Magnum" is that part of the oviduct between the infundibulum and the isthmus containing tubular gland cells that synthesize and secrete the egg white proteins of the egg.

A "MDOT promoter", as used herein, is a synthetic promoter which is active in the tubular gland cells of the magnum of the oviduct amongst other tissues. MDOT is comprised of elements from the ovomucoid (MD) and ovotransferrin (TO) promoters (FIG. 13).

The term "optimized" is used in the context of "optimized coding sequence", wherein the most frequently used codons for each particular amino acid found in the egg white proteins ovalbumin, lysozyme, ovomucoid, and ovotransferrin are used in the design of the optimized human interferon-α 2b (IFN-α 2b) polynucleotide sequence that is inserted into vectors of the present invention. More specifically, the DNA sequence for optimized human IFN-α 2b is based on the hen oviduct optimized codon usage and is created using the BACKTRANSLATE program of the Wisconsin Package, Version 9.1 (Genetics Computer Group Inc., Madison, Wis.) with a codon usage table compiled from the chicken (*Gallus gallus*) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU is used as the codon for the majority of alanines in the optimized human IFN-α 2b coding sequence. The vectors containing the gene for optimized human IFN-α 2b are used to produce transgenic avians that express transgenic poultry derived IFN-α 2b (TPD IFN-α 2b) in their tissues and eggs. Similarly, the above method is employed for the design of other coding sequences proteins such as human erythropoietin (EPO) or other proteins which may be produced in accordance with the invention.

By the methods of the present invention, transgenes can be introduced into avian embryonic blastodermal cells to produce a transgenic avian, transgenic chicken, transgenic turkey, transgenic quail and other avian species, that carry the transgene in the genetic material of its germ-line tissue. The blastodermal cells are typically stage VII-XII cells, or the equivalent thereof, and in one embodiment are near stage X. The cells useful in the present invention include embryonic germ (EG) cells, embryonic stem (ES) cells & primordial germ cells (PGCs). The embryonic blastodermal cells may be isolated freshly, maintained in culture, or reside within an embryo.

The vectors useful in carrying out the methods of the present invention are described herein. These vectors may be used for stable introduction of an exogenous coding sequence into the genome of an avian. Alternatively, the vectors may be used to produce exogenous proteins in specific tissues of an avian, for example, in the oviduct tissue of an avian. The vectors may also be used in methods to produce avian eggs which contain exogenous protein. In one embodiment, the coding sequence and the promoter are both positioned between 5' and 3' LTRs before introduction into blastodermal cells. In one embodiment, the vector is retroviral and the coding sequence and the promoter are both positioned between the 5' and 3' LTRs of the retroviral vector. In one useful embodiment, the LTRs or retroviral vector is derived from the avian leukosis virus (ALV), murine leukemia virus (MLV), or lentivirus.

In one embodiment, the vector includes a signal peptide coding sequence which is operably linked to the coding sequence, so that upon translation in a cell, the signal peptide will direct secretion of the exogenous protein expressed by the vector into the egg white of a hard shell egg. The vector may include a marker gene, wherein the marker gene is operably linked to a promoter.

In some cases, introduction of a vector of the present invention into the embryonic blastodermal cells is performed with embryonic blastodermal cells that are either freshly isolated or in culture. The transgenic cells are then typically injected into the subgerminal cavity beneath a recipient blastoderm in an egg. In some cases, however, the vector is delivered directly to the cells of a blastodermal embryo.

In one embodiment of the invention, vectors used for transfecting blastodermal cells and generating stable integration into the avian genome contain a coding sequence and a promoter in operational and positional relationship to express the coding sequence in the tubular gland cell of the magnum of the avian oviduct, wherein the coding sequence codes for an exogenous protein which is deposited in the egg white of a hard shell egg. The promoter may optionally be a segment of the ovalbumin promoter region which is sufficiently large to direct expression of the coding sequence in the tubular gland cells. The invention involves truncating the ovalbumin promoter and/or condensing the critical regulatory elements of the ovalbumin promoter so that it retains sequences required for expression in the tubular gland cells of the magnum of the oviduct, while being small enough that it can be readily incorporated into vectors.

In one embodiment, a segment of the ovalbumin promoter region may be used. This segment comprises the 5'-flanking region of the ovalbumin gene. The total length of the ovalbumin promoter segment may be from about 0.88 kb to about 7.4 kb in length, and is preferably from about 0.88 kb to about 1.4 kb in length. The segment preferably includes both the steroid-dependent regulatory element and the negative regulatory element of the ovalbumin gene. The segment optionally also includes residues from the 5' untranslated region (5' UTR) of the ovalbumin gene. Hence, the promoter may be derived from the promoter regions of the ovalbumin-, lysozyme-, conalbumin-, ovomucoid-, ovotransferrin- or ovomucin genes (FIG. 14). An example of such a promoter is the synthetic MDOT promoter which is comprised of elements from the ovomucoid and ovotransferrin promoter (FIG. 13). The promoter may also be a promoter that is largely, but not entirely, specific to the magnum, such as the lysozyme promoter. The promoter may also be a mouse mammary tumor virus (MMTV) promoter. Alternatively, the promoter may be a constitutive promoter (e.g., a cytomegalovirus (CMV) promoter, a rous-sarcoma virus (RSV) promoter, a murine leukemia virus (MLV) promoter, etc.). In a preferred embodiment of the invention, the promoter is a cytomegalovirus (CMV) promoter, a MDOT promoter, a rous-sarcoma virus (RSV) promoter, a murine leukemia virus (MLV) promoter, a mouse mammary tumor virus (MMTV) promoter, an ovalbumin promoter, a lysozyme promoter, a conalbumin promoter, an ovomucoid promoter, an ovomucin promoter, and an ovotransferrin promoter. Optionally, the promoter may be at least one segment of a promoter region, such as a segment of the ovalbumin-, lysozyme-, conalbumin-, ovomucoid-, ovomucin-, and ovotransferrin promoter region. In one embodiment, the promoter is a CMV promoter.

FIGS. 1A and 1B illustrate examples of ovalbumin promoter expression vectors. Gene X is a coding sequence which encodes an exogenous protein. Bent arrows indicate the transcriptional start sites. In one example, the vector contains 1.4 kb of the 5' flanking region of the ovalbumin gene (FIG. 1A). The sequence of the "−1.4 kb promoter" of FIG. 1A corresponds to the sequence starting from approximately 1.4 kb upstream (1.4 kb) of the ovalbumin transcription start site and extending approximately 9 residues into the 5' untranslated region of the ovalbumin gene. The approximately 1.4 kb-long segment harbors two critical regulatory elements, the steroid-dependent regulatory element (SDRE) and the negative regulatory element (NRE). The NRE is so named because it contains several negative regulatory elements which block the gene's expression in the absence of hormones (e.g., estrogen). A shorter 0.88 kb segment also contains both elements. In another example, the vector contains approximately 7.4 kb of the 5' flanking region of the ovalbumin gene and harbors two additional elements (HS-III and HS-IV), one of which is known to contain a functional region enabling induction of the gene by estrogen (FIG. 1B). A shorter 6 kb segment also contains all four elements and could optionally be used in the present invention.

Each vector used for random integration according to the present invention preferably comprises at least one 1.2 kb element from the chicken β-globin locus which insulates the gene within from both activation and inactivation at the site of insertion into the genome. In one embodiment, two insulator elements are added to one end of the ovalbumin gene construct. In the β-globin locus, the insulator elements serve to prevent the distal locus control region (LCR) from activating genes upstream from the globin gene domain, and have been shown to overcome position effects in transgenic flies, indicating that they can protect against both positive and negative effects at the insertion site. The insulator element(s) are only needed at either the 5' or 3' end of the gene because the transgenes are integrated in multiple, tandem copies effectively creating a series of genes flanked by the insulator of the neighboring transgene. In another embodiment, the insulator element is not linked to the vector but is cotransfected with the vector. In this case, the vector and the element are joined in tandem in the cell by the process of random integration into the genome.

Each vector may optionally also comprise a marker gene to allow identification and enrichment of cell clones which have stably integrated the expression vector. The expression of the marker gene is driven by a ubiquitous promoter that drives high levels of expression in a variety of cell types. In one embodiment of the invention, the marker gene is human interferon driven by a lysozyme promoter. In another embodiment the green fluorescent protein (GFP) reporter gene (Zolotukhin et al., J. Virol 70:4646-4654 (1995)) is driven by the *Xenopus* elongation factor 1-α (ef-1-α) promoter (Johnson and Krieg, Gene 147:223-26 (1994)). The *Xenopus* ef-1-α promoter is a strong promoter expressed in a variety of cell types. The GFP contains mutations that enhance its fluorescence and is humanized, or modified such that the codons match the codon usage profile of human genes. Since avian codon usage is virtually the same as human codon usage, the humanized form of the gene is also highly expressed in avian blastodermal cells. In alternative embodiments, the marker gene is operably linked to one of the ubiquitous promoters of HSV tk, CMV, β-actin, or RSV.

While human and avian codon usage is well matched, where a nonvertebrate gene is used as the coding sequence in the transgene, the nonvertebrate gene sequence may be modified to change the appropriate codons such that codon usage is similar to that of humans and avians.

Transfection of the blastodermal cells may be mediated by any number of methods known to those of ordinary skill in the art. The introduction of the vector to the cell may be aided by first mixing the nucleic acid with polylysine or cationic lipids which help facilitate passage across the cell membrane. However, introduction of the vector into a cell is preferably achieved through the use of a delivery vehicle such as a liposome or a virus. Viruses which may be used to introduce the vectors of the present invention into a blastodermal cell include, but are not limited to, retroviruses, adenoviruses, adeno-associated viruses, herpes simplex viruses, and vaccinia viruses.

In one method of transfecting blastodermal cells, a packaged retroviral-based vector is used to deliver the vector into embryonic blastodermal cells so that the vector is integrated into the avian genome.

As an alternative to delivering retroviral transduction particles to the embryonic blastodermal cells in an embryo, helper cells which produce the retrovirus can be delivered to the blastoderm.

Useful retrovirus for randomly introducing a transgene into the avian genome is the replication-deficient avian leucosis virus (ALV), the replication-deficient murine leukemia virus (MLV), or the lentivirus. In order to produce an appropriate retroviral vector, a pNLB vector is modified by inserting a region of the ovalbumin promoter and one or more exogenous genes between the 5' and 3' long terminal repeats (LTRs) of the retrovirus genome. The invention contemplates that any coding sequence placed downstream of a promoter that is active in tubular gland cells will be expressed in the tubular gland cells. For example, the ovalbumin promoter will be expressed in the tubular gland cells of the oviduct magnum because the ovalbumin promoter drives the expression of the ovalbumin protein and is active in the oviduct tubular gland cells. While a 7.4 kb ovalbumin promoter has been found to produce the most active construct when assayed in cultured oviduct tubular gland cells, the ovalbumin promoter is preferably shortened for use in the retroviral vector. In one embodiment, the retroviral vector comprises a 1.4 kb segment of the ovalbumin promoter; a 0.88 kb segment would also suffice.

Any of the vectors of the present invention may also optionally include a coding sequence encoding a signal peptide that will direct secretion of the protein expressed by the vector's coding sequence from the tubular gland cells of the oviduct. This aspect of the invention effectively broadens the spectrum of exogenous proteins that may be deposited in avian eggs using the methods of the invention. Where an exogenous protein would not otherwise be secreted, the vector containing the coding sequence is modified to comprise a DNA sequence comprising about 60 bp encoding a signal peptide from the lysozyme gene. The DNA sequence encoding the signal peptide is inserted in the vector such that it is located at the N-terminus of the protein encoded by the DNA.

FIGS. 2A-2D illustrate examples of suitable retroviral vector constructs. The vector construct is inserted into the avian genome with 5' and 3' flanking LTRs. Neo is the neomycin phosphotransferase gene. Bent arrows indicate transcription start sites. FIGS. 2A and 2B illustrate LTR and oviduct transcripts with a sequence encoding the lysozyme signal peptide (LSP), whereas FIGS. 2C and 2D illustrate transcripts without such a sequence. There are two parts to the retroviral vector strategy. Any protein that contains a eukaryotic signal peptide may be cloned into the vectors depicted in FIGS. 2B and 2D. Any protein that is not ordinarily secreted may be cloned into the vectors illustrated in FIGS. 2A and 2B to allow for its secretion from the tubular gland cells.

FIG. 2E illustrates the strategy for cloning an exogenous gene into a lysozyme signal peptide vector. The polymerase chain reaction is used to amplify a copy of a coding sequence, gene X, using a pair of oligonucleotide primers containing restriction enzyme sites that enable the insertion of the amplified gene into the plasmid after digestion with the two enzymes. The 5' and 3' oligonucleotides contain the Bsu36I and XbaI restriction sites, respectively.

Figure 2F:
FIG. 2F illustrates a retroviral vector comprising an ovalbumin promoter controlling expression of a coding sequence, gene X, and an internal ribosome entry site (IRES) element enabling expression of a second coding sequence, gene Y. X and Y represent any gene of interest.

Another aspect of the invention involves the use of internal ribosome entry site (IRES) elements in any of the vectors of the present invention to allow the translation of two or more proteins from a dicistronic or polycistronic mRNA (Example 15). The IRES units are fused to 5' ends of one or more additional coding sequences which are then inserted into the vectors at the end of the original coding sequence, so that the coding sequences are separated from one another by an IRES (FIGS. 2F, 15A and 15D). Pursuant to this aspect of the invention, post-translational modification of the product is facilitated because one coding sequence may encode an enzyme capable of modifying the other coding sequence product. For example, the first coding sequence may encode collagen which would be hydroxylated and made active by the enzyme encoded by the second coding sequence. In the retroviral vector example of FIG. 2F, an internal ribosome entry site (IRES) element is positioned between two exogenous coding sequences (gene X and gene Y). The IRES allows both protein X and protein Y to be translated from the same transcript the transcription of which is directed by a promoter such as the ovalbumin promoter. Bent arrows indicate transcription start sites. The expression of the protein encoded by gene X is expected to be highest in tubular gland cells, where it is specifically expressed but not secreted. The protein encoded by gene Y is also expressed specifically in tubular gland cells but because it is efficiently secreted, protein Y is packaged into the eggs. In the retroviral vector example of FIGS. 15A and 15D, the light chain (LC) and heavy chain (HC) of a human monoclonal antibody are expressed from a single vector, pCMV-LC-emcvIRES-HC, by placement of an IRES from the encephalomyocarditis virus (EMCV). Transcription is driven by a CMV promoter. (See also Murakami et al. (1997) "High-level expression of exogenous genes by replication-competent retrovirus vectors with an internal ribosomal entry site" Gene 202:23-29; Chen et al. (1999) "Production and design of more effective avian replication-incompetent retroviral vectors" Dev. Biol. 214: 370-384; Noel et al. (2000) "Sustained systemic delivery of monoclonal antibodies by genetically modified skin fibroblasts" J. Invest. Dermatol. 115:740-745).

In another aspect of the invention, the coding sequences of vectors used in any of the methods of the present invention are provided with a 3' untranslated region (3' UTR) to confer stability to the RNA produced. When a 3' UTR is added to a retroviral vector, the orientation of the promoter, gene X and the 3' UTR must be reversed in the construct, so that the addition of the 3' UTR will not interfere with transcription of the full-length genomic RNA. In one embodiment, the 3' UTR may be that of the ovalbumin or lysozyme genes, or any 3' UTR that is functional in a magnum cell, i.e., the SV40 late region.

In an alternative embodiment of the invention, a constitutive promoter (e.g., CMV) is used to express the coding sequence of a transgene in the magnum of an avian. In this case, expression is not limited to the magnum; expression also occurs in other tissues within the avian (e.g., blood). The use of such a transgene, which includes a constitutive promoter and a coding sequence, is particularly suitable for effecting or driving the expression of a protein in the oviduct and the subsequent secretion of the protein into the egg white (see FIG. 8A for an example of a CMV driven construct, such as the pNLB-CMV-IFN vector for expressing IFN-α 2b in chickens).

Figure 3:
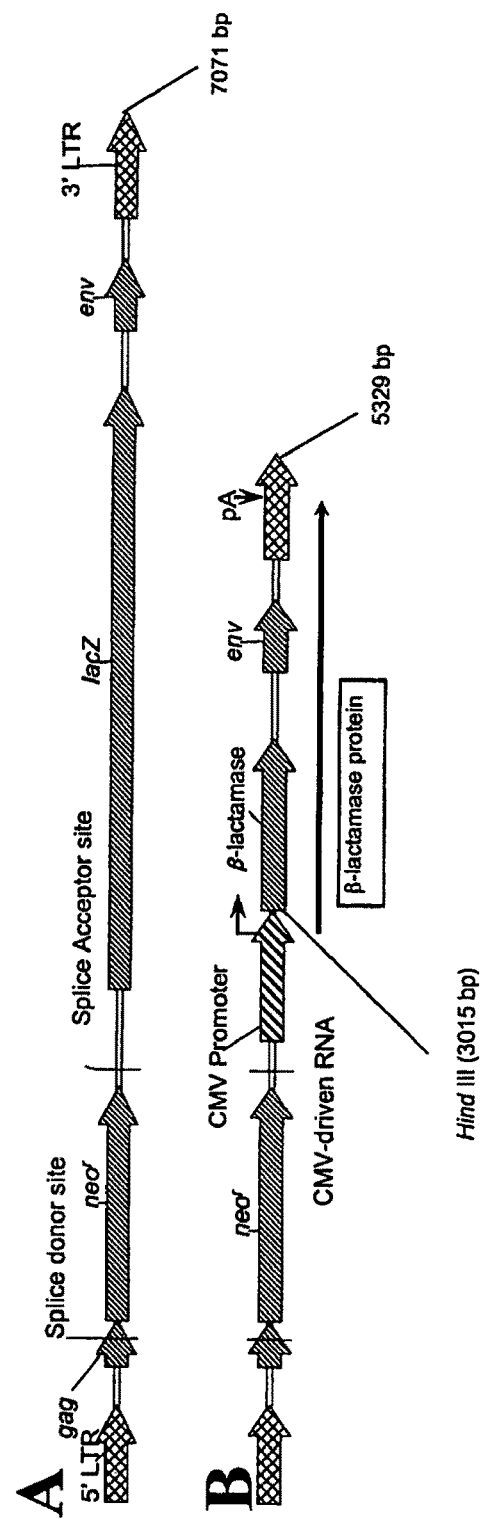
FIGS. 3A and 3B show schematic representations of the ALV-derived vectors pNLB and pNLB-CMV-BL, respectively. Because NLB has not been sequenced in its entirety, measurements in bp (base pair) are estimated from published data (Cosset et al., 1991; Thoraval et al., 1995) and data discussed herein. The vectors are both shown as they would appear while integrated into the chicken genome.

FIG. 3A shows a schematic of the replication-deficient avian leukosis virus (ALV)-based vector pNLB, a vector which is suitable for use in the invention. In the pNLB vector, most of the ALV genome is replaced by the neomycin resistance gene (Neo) and the lacZ gene, which encodes b-galactosidase. FIG. 3B shows the vector pNLB-CMV-BL, in which lacZ has been replaced by the CMV promoter and the β-lactamase coding sequence (β-La or BL). Construction of the vector is reported in the specific examples (Example 1, vide infra). β-lactamase is expressed from the CMV promoter and utilizes a polyadenylation signal (pA) in the 3' long terminal repeat (LTR). The β-Lactamase protein has a natural signal peptide; thus, it is found in blood and in egg white.

Avian embryos are transduced with the pNLB-CMV-BL vector (Example 2, vide infra). The egg whites of eggs from the resulting stably transduced hens contain up to 60 micrograms (μg) of secreted, active β-lactamase per egg (Examples 2 and 3, vide infra).

Figure 8:
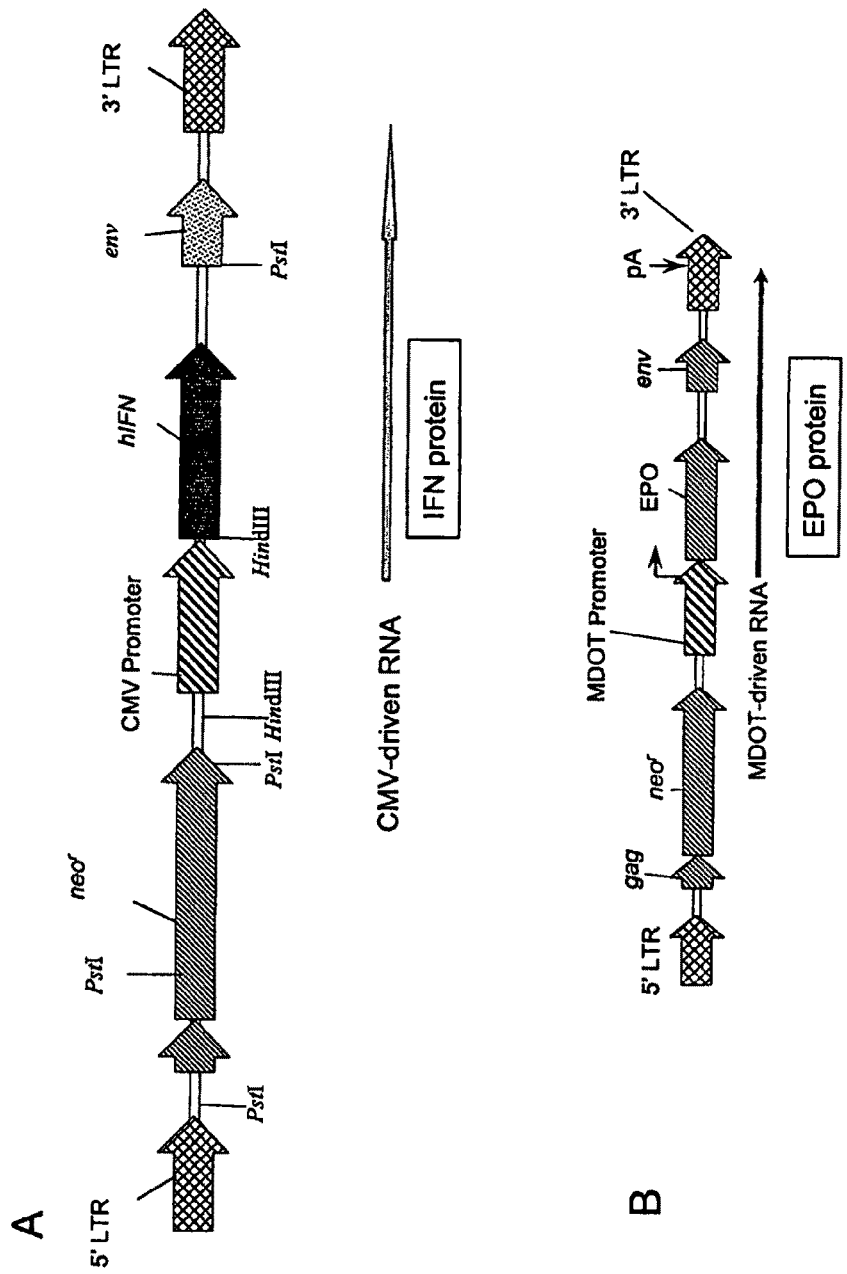
FIGS. 8A and 8B show the pNLB-CMV-IFN vector for expressing IFN-α 2b in chickens; and the pNLB-MDOT-EPO vector used for expressing erythropoietin (EPO) in chickens, respectively.

FIGS. 8A and 8B illustrates the pNLB-CMV-IFN vector used for expressing interferon-α 2b (IFN-α 2b) and the pNLB-MDOT-EPO vector used for expressing erythropoietin (EPO), respectively. Both exogenous proteins (EPO, IFN) are expressed in avians, preferably chicken and turkey.

The pNLB-MDOT-EPO vector is created by substituting an EPO encoding sequence for the BL encoding sequence (Example 10, vide infra). In one embodiment, a synthetic promoter called MDOT is employed to drive expression of EPO. MDOT contains elements from both the ovomucoid and ovotransferrin promoter. The DNA sequence for human EPO is based on hen oviduct optimized codon usage as created using the BACKTRANSLATE program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins. The EPO DNA sequence is synthesized and cloned into the vector and the resulting plasmid is pNLB-MDOT-EPO (a.k.a. pAVIJCR-A145.27.2.2). In one embodiment, transducing particles (i.e., transduction particles) are produced for the vector, and these transducing particles are titered to determine the appropriate concentration that can be used to inject embryos. Eggs are then injected with transducing particles after which they hatch about 21 days later.

The exogenous protein levels such as the EPO levels can then be measured by an ELISA assay from serum samples collected from chicks one week after hatch. Male birds are selected for breeding, wherein birds are screened for G0 roosters which contain the EPO transgene in their sperm. Preferably, roosters with the highest levels of the transgene in their sperm samples are bred to nontransgenic hens by artificial insemination. Blood DNA samples are screened for the presence of the transgene. A number of chicks are usually found to be transgenic (G1 avians). Chick serum is tested for the presence of human EPO (e.g., ELISA assay). The egg white in eggs from G1 hens is also tested for the presence of human EPO. The EPO (i.e., derived from the optimized coding sequence of human EPO) present in eggs of the present invention is biologically active (Example 11).

Similarly, the pNLB-CMV-IFN vector (FIG. 8A) is created by substituting an IFN encoding sequence for the BL encoding sequence (Example 12, vide infra). In one embodiment, a constitutive cytomegalovirus (CMV) promoter is employed to drive expression of IFN. More specifically, the IFN coding sequence is controlled by the cytomegalovirus (CMV) immediate early promoter/enhancer and SV40 polyA site. FIG. 8A illustrates pNLB-CMV-IFN used for expressing IFN in avians, for example, chicken and turkey. An optimized coding sequence is created for human IFN-α 2b, wherein the most frequently used codons for each particular amino acid found in the egg white proteins ovalbumin, lysozyme, ovomucoid, and ovotransferrin are used in the design of the human IFN-α 2b sequence that is inserted into vectors of the present invention. More specifically, the DNA sequence for the optimized human IFN-α 2b (FIG. 11A) is based on the hen oviduct optimized codon usage and is created using the BACK-TRANSLATE program (supra) with a codon usage table compiled from the chicken (*Gallus gallus*) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU is used as the codon for the majority of alanines in the optimized human IFN-α 2b sequence. The vectors containing the gene for the optimized human IFN-α 2b sequence are used to create transgenic avians that express TPD IFN-α2b in their tissues and eggs.

Transducing particles (i.e., transduction particles) are produced for the vector and titered to determine the appropriate concentration that can be used to inject embryos (Example 2, vide infra). Thus, chimeric avians are produced (see also Example 13, vide infra). Avian eggs are windowed according to the Speksnijder procedure (U.S. Pat. No. 5,897,998), and eggs are injected with transducing particles Eggs hatch about 21 days after injection. hIFN levels are measured (e.g., ELISA assay) from serum samples collected from chicks one week after hatch. As with EPO (supra), male birds are selected for breeding. In order to screen for G0 roosters which contain the IFN transgene in their sperm, DNA is extracted from rooster sperm samples. The G0 roosters with the highest levels of the transgene in their sperm samples are bred to nontransgenic hens by artificial insemination. Blood DNA samples are screened for the presence of the transgene. The serum of transgenic roosters is tested for the presence of hIFN (e.g., ELISA assay). If the exogenous protein is confirmed the sperm of the transgenic roosters is used for artificial insemination of nontransgenic hens. A certain percent of the offspring will then contain the transgene (e.g., more than 50%). When IFN (i.e., derived from the optimized coding sequence of human IFN) is present in eggs of the present invention, the IFN may be tested for biological activity. As with EPO, such eggs usually contain biologically active IFN, such as TPD IFN-α 2b (FIG. 11B).

The methods of the invention which provide for the production of exogenous protein in the avian oviduct and the production of eggs which contain exogenous protein involve an additional step subsequent to providing a suitable vector and introducing the vector into embryonic blastodermal cells so that the vector is integrated into the avian genome. The subsequent step involves deriving a mature transgenic avian from the transgenic blastodermal cells produced in the previous steps. Deriving a mature transgenic avian from the blastodermal cells optionally involves transferring the transgenic blastodermal cells to an embryo and allowing that embryo to develop fully, so that the cells become incorporated into the avian as the embryo is allowed to develop. The resulting chick is then grown to maturity. In one embodiment, the cells of a blastodermal embryo are transfected or transduced with the vector directly within the embryo (Example 2). The resulting embryo is allowed to develop and the chick allowed to mature.

In either case, the transgenic avian so produced from the transgenic blastodermal cells is known as a founder. Some founders will carry the transgene in the tubular gland cells in the magnum of their oviducts. These avians will express the exogenous protein encoded by the transgene in their oviducts. The exogenous protein may also be expressed in other tissues (e.g., blood) in addition to the oviduct. If the exogenous protein contains the appropriate signal sequence(s), it will be secreted into the lumen of the oviduct and into the egg white of the egg. Some founders are germ-line founders (Examples 8 and 9). A germ-line founder is a founder that carries the transgene in genetic material of its germ-line tissue, and may also carry the transgene in oviduct magnum tubular gland cells that express the exogenous protein. Therefore, in accordance with the invention, the transgenic avian will have tubular gland cells expressing the exogenous protein, and the offspring of the transgenic avian will also have oviduct magnum tubular gland cells that express the exogenous protein. Alternatively, the offspring express a phenotype determined by expression of the exogenous gene in specific tissue(s) of the avian (Example 6, Table 2). In one embodiment of the invention, the transgenic avian is a chicken or a turkey.

The invention can be used to express, in large yields and at low cost, desired proteins including those used as human and animal pharmaceuticals, diagnostics, and livestock feed additives. For example, the invention includes transgenic avians that produce such proteins and eggs laid by the transgenic avians which contain the protein, for example, in the egg white. The present invention is contemplated for use in the production of any desired protein including pharmaceutical proteins with the requisite that the coding sequence of the protein can be introduced into an oviduct cell in accordance with the present invention. In fact, all proteins tested thus far for heterologous production in accordance with the present invention, including interferon α 2b, GM-CSF, interferon β, erythropoietin, G-CSF, CTLA4-Fc fusion protein and β-lactamase, have been produced successfully employing the methods disclosed herein.

The production of human proteins as disclosed herein is of particular interest. The human form of each of the proteins disclosed herein for which there is a human form, is contemplated for production in accordance with the invention.

Proteins contemplated for production as disclosed herein include, but are not limited to, fusion proteins, growth hormones, cytokines, structural proteins and enzymes including human growth hormone, interferon, lysozyme, and β-casein, albumin, α-1 antitrypsin, antithrombin III, collagen, factors VIII, IX, X (and the like), fibrinogen, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), somatotropin, and chymotrypsin. Modified immunoglobulins and antibodies, including immunotoxins which bind to surface antigens on human tumor cells and destroy them, can also be produced as disclosed herein.

Other specific examples of therapeutic proteins which may be produced as disclosed herein include, without limitation, factor VIII, b-domain deleted factor VIII, factor VIIa, factor IX, anticoagulants; hirudin, alteplase, tpa, reteplase, tpa, tpa-3 of 5 domains deleted, insulin, insulin lispro, insulin aspart, insulin glargine, long-acting insulin analogs, hgh, glucagons, tsh, follitropin-beta, fsh, gm-csf, pdgh, ifn alpha2, ifn alpha2a, ifn alpha2b, inf-apha, inf-beta 1b, ifn-beta 1a, ifn-gamma1b, il-2, il-11, hbsag, ospa, murine mab directed against t-lymphocyte antigen, murine mab directed against tag-72, tumor-associated glycoprotein, fab fragments derived from chimeric mab directed against platelet surface receptor gpII(b)/III(a), murine mab fragment directed against tumor-associated antigen ca125, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes domase-alpha dnase, beta glucocerebrosidase, tnf-alpha, il-2-diptheria toxin fusion protein, tnfr-lgg fragment fusion protein laronidase, dnaases, alefacept, darbepoetin alfa (colony stimulating factor), tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone.

The invention includes methods for producing multimeric proteins including immunoglobulins, such as antibodies, and antigen binding fragments thereof. Thus, in one embodiment of the present invention, the multimeric protein is an immunoglobulin, wherein the first and second heterologous polypeptides are immunoglobulin heavy and light chains respectively.

In certain embodiments, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide encoded by an expression vector may also be an immunoglobulin light chain polypeptide comprising a variable region or a variant thereof, and may further comprise a J region and a C region. The present invention also contemplates multiple immunoglobulin regions that are derived from the same animal species, or a mixture of species including, but not only, human, mouse, rat, rabbit and chicken. In certain embodiments, the antibodies are human or humanized.

In other embodiments, the immunoglobulin polypeptide encoded by at least one expression vector comprises an immunoglobulin heavy chain variable region, an immunoglobulin light chain variable region, and a linker peptide thereby forming a single-chain antibody capable of selectively binding an antigen.

Examples of therapeutic antibodies that may be produced in methods of the invention include, but are not limited to, HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath; Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); CAT-152, a human anti-TGF-β$_2$ antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; and Ranibizumab (Genentech) is a chimeric (mouse and human) monoclonal antibody used to treat macular degeneration.

In one aspect, the invention is drawn to G-CSF produced in poultry. In one aspect, the invention is drawn to G-CSF with a poultry derived glycosylation pattern (TPD G-CSF) wherein the G-CSF is obtained from avian cells, for example, avian cells of a chicken, quail or turkey. Also included in the invention are the human proteins including cytokines such as G-CSF produced in poultry in isolated or purified form and human proteins including cytokines such as G-CSF produced in poultry present in pharmaceutical compositions. The isolation of the proteins including G-CSF can be accomplished by methodologies readily apparent to a practitioner skilled in the art of protein purification. The make-up of formulations useful for producing pharmaceutical compositions are also well known in the art.

Figure 9:
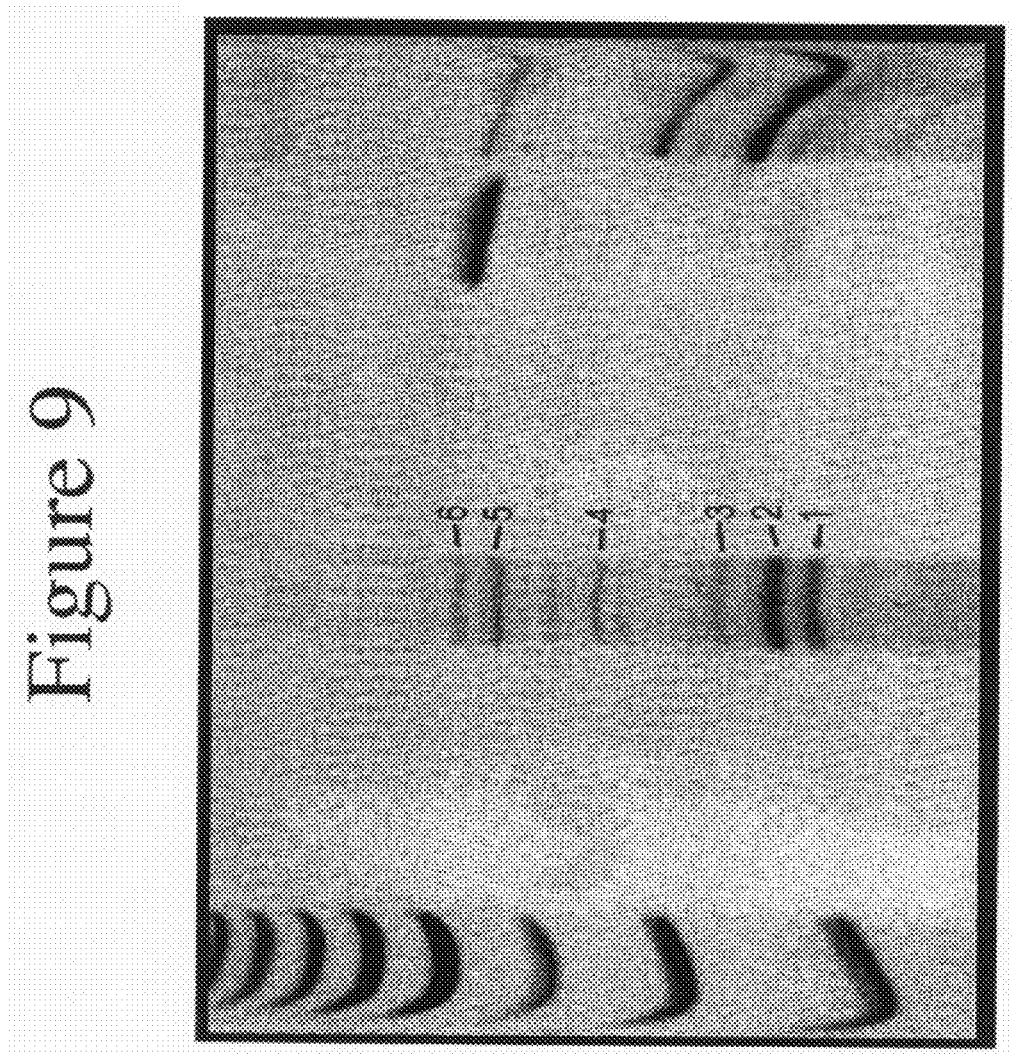
FIG. 9 depicts the novel glycosylation pattern of transgenic poultry derived interferon-α 2b (TPD IFN-α 2b), including all 6 bands.

The present invention encompasses transgenic poultry derived therapeutic or pharmaceutical proteins having a poultry derived glycosylation pattern which are derived from avians. For example, the invention includes interferon-α 2 (TPD IFN-α 2) derived from avians. TPD IFN-α 2 (e.g., species type b) exhibits a new glycosylation pattern and contains new glyco forms (bands 4 and 5 are α-Gal extended disaccharides; see FIG. 9) not normally seen in human peripheral blood leukocyte derived interferon-α 2 (PBL IFN-α 2b). TPD IFN-α 2b also contains O-linked carbohydrate structures that are similar to human PBL IFN-α 2b and is more efficiently produced in chickens than the human form.

The present invention contemplates an isolated polynucleotide comprising the optimized polynucleotide sequence of proteins produced as disclosed herein. For example, the invention includes avian optimized coding sequence for human IFN-α 2b, i.e., recombinant transgenic poultry derived interferon-α 2b (TPD IFN-α 2b) (SEQ ID NO: 1). The coding sequence for optimized human IFN-α 2b includes 498 nucleic acids and 165 amino acids (see SEQ ID NO: 1 and FIG. 11A). Similarly, the coding sequence for natural human IFN-α 2b includes 498 nucleotides (NCBI Accession Number AF405539 and GI:15487989) and 165 amino acids (NCBI Accession Number AAL01040 and GI:15487990). The most frequently used codons for each particular amino acid found in the egg white proteins ovalbumin, lysozyme, ovomucoid, and ovotransferrin are used in the design of the optimized human IFN-α 2b coding sequence which is inserted into vectors of the present invention. More specifically, the DNA sequence for the optimized human IFN-α 2b is based on the hen oviduct optimized codon usage and is created using the BACKTRANSLATE program of the Wisconsin Package, Version 9.1 (Genetics Computer Group Inc., Madison, Wis.) with a codon usage table compiled from the chicken (*Gallus gallus*) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU is used as the codon for the majority of alanines in the optimized human IFN-α 2b coding sequence. The vectors containing the gene for optimized human IFN-α2b are used to create transgenic avians that express TPD IFN-α 2b in their tissues and eggs.

Figure 10:
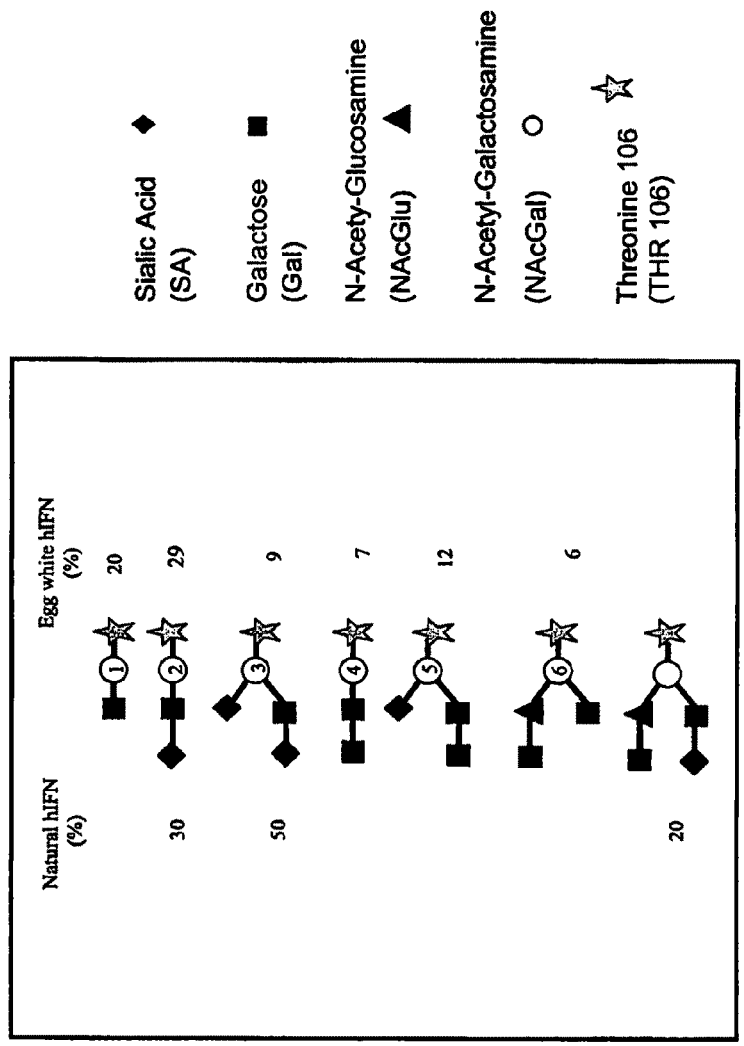
FIG. 10 shows the comparison of human peripheral blood leukocyte derived interferon-α 2b (PBL IFN-α 2b or natural hIFN) and transgenic poultry derived interferon-α 2b (TPD IFN-α 2b or egg white hIFN).
Figure 16:
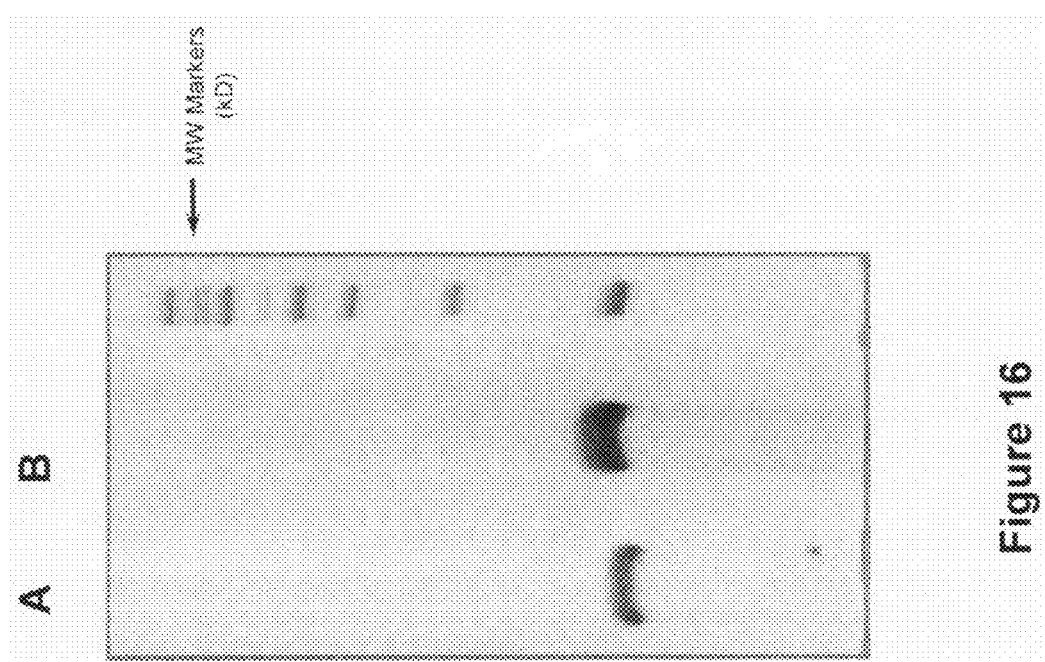
FIG. 16 shows a silver stained SDS PAGE of Neupogen® (lane A) and TPD G-CSF (lane B).

As discussed in Example 13 (vide infra), TPD IFN-α 2b is produced in chicken. However, TPD IFN-α 2b may also be produced in turkey and other avian species such as quail. In a preferred embodiment of the invention, TPD IFN-α 2b is expressed in chicken and turkey and their hard shell eggs. A carbohydrate analysis (Example 14, vide infra), including a monosaccharide analysis and FACE analysis, reveals the sugar make-up or novel glycosylation pattern of the protein. As such, TPD IFN-α 2b shows the following monosaccharide residues: N-Acetyl-Galactosamine (NAcGal), Galactose (Gal), N-Acetyl-Glucosamine (NAcGlu), and Sialic acid (SA). However, there is no N-linked glycosylation in TPD IFN-α 2b. Instead, TPD IFN-α 2b is O-glycosylated at Thr-106. This type of glycosylation is similar to human IFN-α 2, wherein the Thr residue at position 106 is unique to IFN-α 2. Similar to natural IFN-α, TPD IFN-α 2b does not have mannose residues. A FACE analysis reveals 6 bands (FIG. 9) that represent various sugar residues, wherein bands 1, 2 and 3 are un-sialyated, mono-sialyated, and di-sialyated, respectively (FIG. 10). The sialic acid (SA) linkage is alpha 2-3 to Galactose (Gal) and alpha 2-6 to N-Acetyl-Galactosamine (NAcGal). Band 6 represents an un-sialyated tetrasaccharide. Bands 4 and 5 are alpha-Galactose (alpha-Gal) extended disaccharides that are not seen in human PBL IFN-α 2b or natural human IFN (natural hIFN). FIG. 10 shows the comparison of TPD IFN-α 2b (egg white hIFN) and human PBL IFN-α 2b (natural hIFN). Minor bands are present between bands 3 and 4 and between bands 4 and 5 in TPD IFN-α 2b (vide infra).

The present invention contemplates an isolated polypeptide sequence (SEQ ID NO: 2) of TPD IFN-α 2b (see also FIG. 11B) and a pharmaceutical composition thereof, wherein the protein is O-glycosylated at Thr-106 with one or more of the carbohydrate structures disclosed herein as follows:

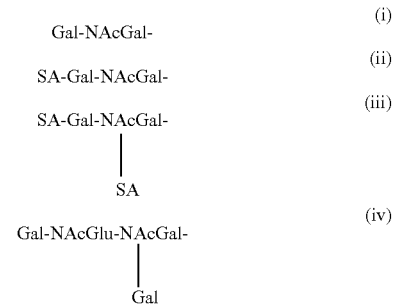

Gal-Gal-NAcGal- (v)

Gal-Gal-NAcGal- (vi)
|
SA wherein Gal=Galactose,
NAcGal=N-Acetyl-Galactosamine,
NAcGlu=N-Acetyl-Glucosamine, and
SA=Sialic Acid.

In a one embodiment of the present invention, the percentages are as follows:

Gal-NAcGal- is about 20%  (i)

SA-Gal-NAcGal- is about 29%  (ii)

SA-Gal-NAcGal- is about 9%  (iii)
|
SA

Gal-NAcGlu-NAcGal- is about 6%  (iv)
|
Gal

Gal-Gal-NAcGal- is about 7%  (v)

Gal-Gal-NAcGal- is about 12%  (vi)
|
SA

Minor bands are present between bands 3 and 4 and between bands 4 and 5 which account for about 17% in TPD IFN-α 2b.

In one embodiment, the invention is directed to human proteins having a poultry derived glycosylation pattern. In one embodiment, the poultry derived glycosylation pattern is obtained from avian oviduct cells, for example, tubular gland cells. For example, glycosylation patterns are disclosed herein which have been demonstrated to be present on human proteins produced in oviduct cells of a chicken in accordance with the present invention.

In one embodiment, the invention is directed to human G-CSF produced in avians (e.g., avian oviduct cells) such as chickens, turkey and quail having a poultry derived glycosylation pattern. The mature hG-CSF amino acid sequence is shown in FIG. 18 C. Nucleotide sequence used herein to produce G-CSF is shown in FIG. 18 A and in NCBI Accession NM 172219. Nucleotide sequences optimized for avian (e.g., chicken) codon usage are also contemplated for use to produce G-CSF and other proteins such as human proteins produced in accordance with the invention.

The invention includes the eggs and the avians (e.g., chicken, turkey and quail) that lay the eggs containing G-CSF molecules of the invention comprising one or more of the glycosylation structures shown below:

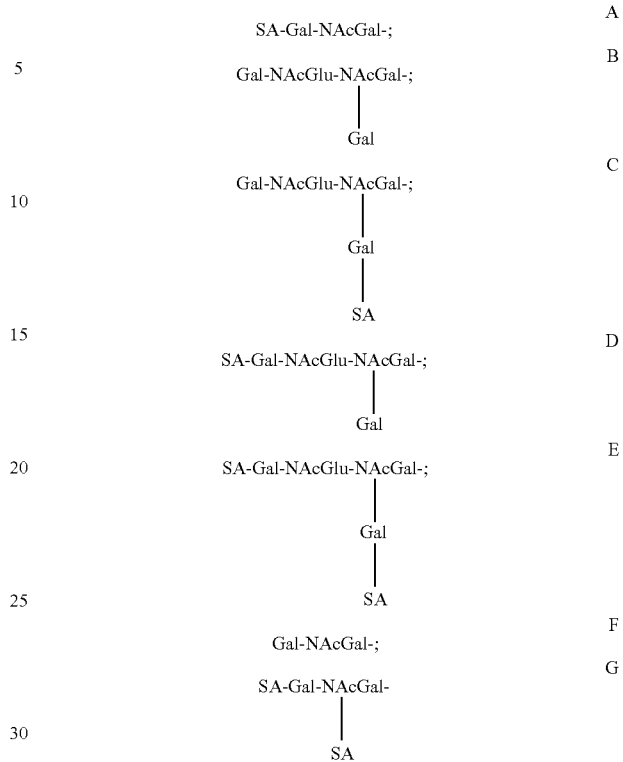

In one embodiment, the invention includes a mixture of G-CSF molecules wherein the mixture contains G-CSF molecules having a glycosylation structure selected from one or more of Structure A, Structure B, Structure C, Structure D, Structure E, Structure F and Structure G. The invention also includes a mixture of G-CSF molecules wherein the mixture contains G-CSF molecules having a glycosylation structure selected from one or more of Structure A, Structure B, Structure C, Structure D, Structure E, Structure F and Structure G wherein the mixture is isolated or purified, for example, purified from an egg or from egg white produced in accordance with the invention. Also included is a mixture of G-CSF molecules wherein the mixture contains G-CSF molecules having two, three, four, five or six of the structures: Structure A, Structure B, Structure C, Structure D, Structure E, Structure F and/or Structure G. Also included is a mixture of G-CSF molecules wherein the mixture contains G-CSF molecules having two, three, four, five or six of the structures: Structure A, Structure B, Structure C, Structure D, Structure E, Structure F and/or Structure G, that has been isolated or purified, for example, purified from an egg or from egg white produced in accordance with the invention.

The invention also includes an individual G-CSF molecule comprising a Structure A. The invention also includes an individual G-CSF molecule comprising a Structure B. The invention also includes an individual G-CSF molecule comprising a Structure C. The invention also includes an individual G-CSF molecule comprising a Structure D. The invention also includes an individual G-CSF molecule comprising a Structure E. The invention also includes an individual G-CSF molecule comprising a Structure F. The invention also includes an individual G-CSF molecule comprising a Structure G. In one embodiment, the individual G-CSF molecule is present in a mixture of G-CSF molecules that may be an isolated or purified mixture of G-CSF molecules, for example, the mixture being purified from an egg or from egg white produced in accordance with the invention. In one embodiment, the individual G-CSF molecule is isolated or purified, for example, purified as disclosed herein (e.g., by HPLC as disclosed in Example 20).

The embodiments of the invention as specified herein regarding G-CSF, for example, mixtures of G-CSF molecules and individual G-CSF molecules (in the preceding two paragraphs), are also applicable in general for each of the other proteins produced in accordance with the invention and their corresponding poultry derived glycosylation structures.

It is also contemplated that the glycosylation structures demonstrated to be present on one protein of the invention may be present on another protein of the invention. For example, glycosylation structures shown to be present on TPD G-CSF may also be present on TPD GM-CSF, TPD EPO, TPD IFN and/or other TPD proteins. In another example, it is contemplated that the glycosylation structures determined to be present on TPD IFN α2 may be present on TPD G-CSF, TPD GM-CSF, TPD EPO and/or other transgenic poultry derived (TPD) proteins. The invention also specifically contemplates human proteins in general having one or more of the TPD glycosylation structures disclosed herein.

While it is possible that, for use in therapy, therapeutic proteins produced in accordance with this invention may be administered in raw form, it is preferable to administer the therapeutic proteins as part of a pharmaceutical formulation.

The invention thus further provides pharmaceutical formulations comprising poultry derived glycosylated therapeutic proteins or a pharmaceutically acceptable derivative thereof together with one or more pharmaceutically acceptable carriers thereof and, optionally, other therapeutic and/or prophylactic ingredients and methods of administering such pharmaceutical formulations. The carrier(s) must be "acceptable" in the sense of being compatible with the other ingredients of the formulation and not deleterious to the recipient thereof. Methods of treating a patient (e.g., quantity of pharmaceutical protein administered, frequency of administration and duration of treatment period) using pharmaceutical compositions of the invention can be determined using standard methodologies known to physicians of skill in the art.

Pharmaceutical formulations include those suitable for oral, rectal, nasal, topical (including buccal and sub-lingual), vaginal or parenteral. The pharmaceutical formulations include those suitable for administration by injection including intramuscular, sub-cutaneous and intravenous administration. The pharmaceutical formulations also include those for administration by inhalation or insufflation. The formulations may, where appropriate, be conveniently presented in discrete dosage units and may be prepared by any of the methods well known in the art of pharmacy. The methods of producing the pharmaceutical formulations typically include the step of bringing the therapeutic proteins into association with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

Therapeutic proteins of the invention may also be formulated for parenteral administration (e.g., by injection, for example bolus injection or continuous infusion) and may be presented in unit dose form in ampoules, pre-filled syringes, small volume infusion or in multi-dose containers with an added preservative. The therapeutic proteins may be injected by, for example, subcutaneous injections, intramuscular injections, and intravenous infusions or injections.

The therapeutic proteins may take such forms as suspensions, solutions, or emulsions in oily or aqueous vehicles, and may contain formulatory agents such as suspending, stabilizing and/or dispersing agents. It is also contemplated that the therapeutic proteins may be in powder form, obtained by aseptic isolation of sterile solid or by lyophilization from solution, for constitution with a suitable vehicle, e.g., sterile, pyrogen-free water, before use.

For topical administration to the epidermis, the therapeutic proteins produced according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably represented as unit dose suppositories. Suitable carriers include cocoa butter and other materials commonly used in the art, and the suppositories may be conveniently formed by a mixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration the therapeutic proteins of the invention may be used as a liquid spray or dispersible powder or in the form of drops.

Drops may be formulated with an aqueous or non-aqueous base also comprising one or more dispersing agents, solubilizing agents or suspending agents. Liquid sprays are conveniently delivered from pressurized packs.

For administration by inhalation, therapeutic proteins according to the invention may be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

For administration by inhalation or insufflation, the therapeutic proteins according to the invention may take the form of a dry powder composition, for example a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient, may be employed.

The pharmaceutical compositions according to the invention may also contain other active ingredients such as antimicrobial agents, or preservatives.

In addition, it is contemplated that the therapeutic proteins of the invention may be used in combination with other therapeutic agents.

Compositions or compounds of the invention can be used to treat a variety of conditions. For example, there are many conditions for which treatment therapies are known to practitioners of skill in the art in which therapeutic proteins obtained from cell culture (e.g., CHO cells) are employed. The present invention contemplates that the therapeutic proteins produced in an avian system containing a poultry derived glycosylation pattern can be employed to treat such conditions. That is, the invention contemplates the treatment of conditions known to be treatable by conventionally produced therapeutic proteins by using therapeutic proteins produced in accordance with the invention. For example, erythropoietin produced in accordance with the invention can be used to treat human conditions such as anemia and kidney disease (e.g., chronic renal failure) and G-CSF produced in accordance with the invention can be used to treat cancer patients, as understood in the art.

Generally, the dosage administered will vary depending upon known factors such as age, health and weight of the recipient, type of concurrent treatment, frequency of treatment, and the like. Usually, a dosage of active ingredient can be between about 0.0001 and about 10 milligrams per kilogram of body weight. Precise dosage, frequency of administration and time span of treatment can be determined by a physician skilled in the art of administration of the respective therapeutic protein.

The following specific examples are intended to illustrate the invention and should not be construed as limiting the scope of the claims.

EXAMPLE 1

Vector Construction

The lacZ gene of pNLB, a replication-deficient avian leukosis virus (ALV)-based vector (Cosset et al., 1991), was replaced with an expression cassette consisting of a cytomegalovirus (CMV) promoter and the reporter gene, β-lactamase. The pNLB and pNLB-CMV-BL vector constructs are diagrammed in FIGS. 3A and 3B, respectively.

To efficiently replace the lacZ gene of pNLB with a transgene, an intermediate adaptor plasmid was first created, pNLB-Adapter. pNLB-Adapter was created by inserting the chewed back ApaI/ApaI fragment of pNLB (Cosset et al., J. Virol. 65:3388-94 (1991)) (in pNLB, the 5' ApaI resides 289 bp upstream of lacZ and the 3'ApaI resides 3' of the 3' LTR and Gag segments) into the chewed-back KpnI/SacI sites of pBluescriptKS(−). The filled-in MluI/XbaI fragment of pCMV-BL (Moore et al., Anal. Biochem. 247: 203-9 (1997)) was inserted into the chewed-back KpnI/NdeI sites of pNLB-Adapter, replacing lacZ with the CMV promoter and the BL gene (in pNLB, KpnI resides 67 bp upstream of lacZ and NdeI resides 100 bp upstream of the lacZ stop codon), thereby creating pNLB-Adapter-CMV-BL. To create pNLB-CMV-BL, the HindIII/BlpI insert of pNLB (containing lacZ) was replaced with the HindIII/BlpI insert of pNLB-Adapter-CMV-BL. This two step cloning was necessary because direct ligation of blunt-ended fragments into the HindIII/BlpI sites of pNLB yielded mostly rearranged subclones, for unknown reasons.

EXAMPLE 2

Creation of the pNLB-CMV-BL Founder Flock

Sentas and Isoldes were cultured in F10 (Gibco), 5% newborn calf serum (Gibco), 1% chicken serum (Gibco), 50 µg/ml phleomycin (Cayla Laboratories) and 50 µg/ml hygromycin (Sigma). Transduction particles were produced as described in Cosset et al., 1993, herein incorporated by reference, with the following exceptions. Two days after transfection of the retroviral vector pNLB-CMV-BL (from Example 1, above) into $9 \times 10^5$ Sentas, virus was harvested in fresh media for 6-16 hours and filtered. All of the media was used to transduce $3 \times 10^6$ Isoldes in 3 100 mm plates with polybrene added to a final concentration of 4 µg/ml. The following day the media was replaced with media containing 50 µg/ml phleomycin, 50 µg/ml hygromycin and 200 µg/ml G418 (Sigma). After 10-12 days, single G418 resistant colonies were isolated and transferred to 24-well plates. After 7-10 days, titers from each colony were determined by transduction of Sentas followed by G418 selection. Typically 2 out of 60 colonies gave titers at $1-3 \times 10^5$. Those colonies were expanded and virus concentrated to $2-7 \times 10^6$ as described in Allioli et al., Dev. Biol. 165:30-7 (1994), herein incorporated by reference. The integrity of the CMV-BL expression cassette was confirmed by assaying for β-lactamase in the media of cells transduced with NLB-CMV-BL transduction particles.

The transduction vector, pNLB-CMV-BL, was injected into the subgerminal cavity of 546 unincubated SPF White Leghorn embryos, of which 126 chicks hatched and were assayed for secretion of β-lactamase (lactamase) into blood. In order to measure the concentration of active lactamase in unknown samples, a kinetic colorimetric assay was employed in which PADAC, a purple substrate, is converted to a yellow compound specifically by lactamase. Lactamase activity was quantitated by monitoring the decrease in $OD_{570}$ nm during a standard reaction time and compared to a standard curve with varying levels of purified lactamase (referred to as the "lactamase assay"). The presence or absence of lactamase in a sample could also be determined by visually scoring for the conversion of purple to yellow in a test sample overnight or for several days (the "overnight lactamase assay"). The latter method was suitable for detection of very low levels of lactamase or for screening a large number of samples. At one to four weeks of age, chick serum samples were tested for the presence of lactamase. Twenty-seven chicks had very low levels of lactamase in their serum that was detectable only after the overnight lactamase assay and, as these birds matured, lactamase was no longer detectable. As shown in Table 1 below and FIG. 4A, 9 additional birds (3 males and 6 females) had serum levels of lactamase that ranged from 11.9 to 173.4 ng/ml at six to seven months post-hatch.

TABLE 1

Expression of β-Lactamase in NLB-CMV-BL-Transduced Chickens

| | | Average ng/ml of β-Lactamase | | |
|---|---|---|---|---|
| Sex | Band No. | Serum: 8 Month Birds | Egg White: 8 Month Hens[3] | Egg White: 14 Month Hens[3] |
| NA[1] | Controls[2] | 0.0 ± 7.4 | 0.0 ± 13.6 | 0.0 ± 8.0 |
| Female | 1522 | 36.7 ± 1.6 | 56.3 ± 17.8 | 47.9 ± 14.3 |
| Female | 1549 | 11.9 ± 1.3 | 187.0 ± 32.4 | 157.0 ± 32.2 |
| Female | 1581 | 31.5 ± 4.8 | 243.8 ± 35.7 | 321.7 ± 68.8 |
| Female | 1587 | 33.9 ± 1.4 | 222.6 ± 27.7 | 291.0 ± 27.0 |
| Female | 1790 | 31.0 ± 0.5 | 136.6 ± 20.2 | 136.3 ± 11.0 |
| Female | 1793 | 122.8 ± 3.6 | 250.0 ± 37.0 | 232.5 ± 28.6 |
| Male | 2395 | 16.0 ± 2.3 | NA | NA |
| Male | 2421 | 165.5 ± 5.0 | NA | NA |
| Male | 2428 | 173.4 ± 5.9 | NA | NA |

[1]NA: not applicable.
[2]Controls were obtained from untreated hens.
[3]Represents the average of 5 to 20 eggs.

EXAMPLE 3

β-Lactamase Expression in the Egg White of G0 Hens

Fifty-seven pullets transduced with pNLB-CMV-BL retroviral vector were raised to sexual maturity and egg white from each hen was tested for active β-lactamase (lactamase) at 8 months of age. Of the 57 birds, six had significant levels of lactamase that ranged from 56.3 to 250.0 ng/ml (Table 1, supra). No other hens in this group had detectable levels of lactamase in their egg white, even after incubation of PADAC with the sample for several days. Lactamase was not detectable in egg white from 24 hens that were mock injected and in 42 hens that were transduced with a NLB vector that did not carry the lactamase transgene. Stable lactamase expression was still detectable in the egg white of the six expressing hens six months following the initial assays (Table 1, supra).

Lactamase was detected in the egg white of all six hens by a western blot assay with an anti-β-lactamase antibody. The egg white lactamase was the same size as the bacterially produced, purified lactamase that was used as a standard. The amount detected in egg white by Western analysis was consistent with that determined by the enzymatic assay, indicating that a significant proportion of the egg white lactamase was biologically active. Hen-produced lactamase in egg white stored at 4° C. lost no activity and showed no change in molecular weight even after several months of storage. This observation allowed storage of lactamase-containing eggs for extended periods prior to analysis.

EXAMPLE 4

Figure 4:
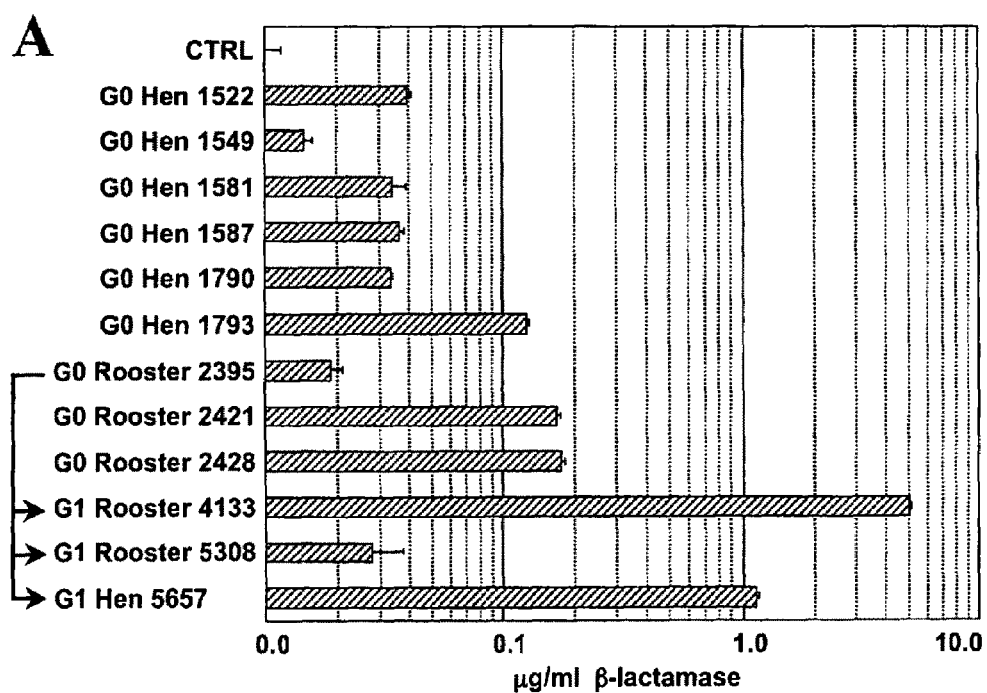
FIGS. 4A and 4B show the amount of β-lactamase (lactamase) in the blood serum of chimeric and transgenic chickens.
Figure 4:
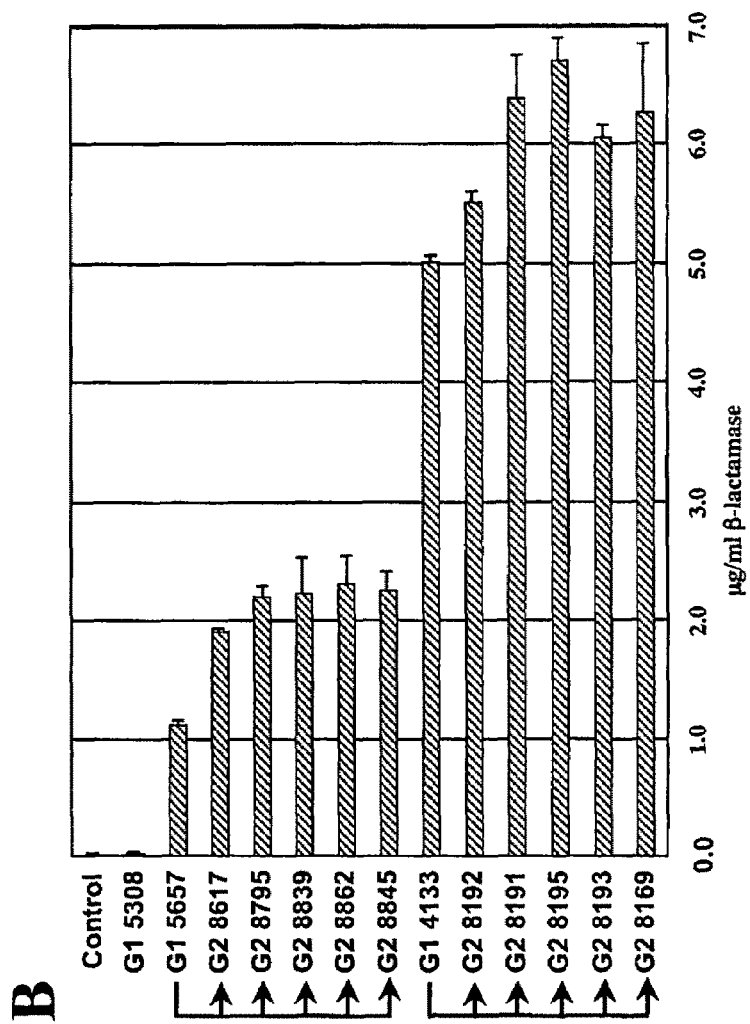

Germline Transmission and Serum Expression of the β-Lactamase Transgene in G1 and G2 Transgenic Chickens DNA was extracted from sperm collected from 56 G0 roosters and three of the 56 birds that harbored significant levels of the transgene in their sperm DNA as determined by quantitative PCR were selected for breeding. These roosters were the same three that had the highest levels of β-lactamase (lactamase) in their blood (roosters 2395, 2421 and 2428). Rooster 2395 gave rise to three G1 transgenic offspring (out of 422 progeny) whereas the other two yielded no transgenic offspring out of 630 total progeny. Southern analysis of blood DNA from each of the three G1 transgenic chickens confirmed that the transgenes were intact and that they were integrated at unique random loci. The serum of the G1 transgenic chicks, 5308, 5657 and 4133, at 6 to 11 weeks post-hatch contained 0.03, 2.0 and 6.0 μg/ml of lactamase, respectively. The levels of lactamase dropped to levels of 0.03, 1.1 and 5.0 μg/ml when the chickens were assayed again at 6 to 7 months of age (FIG. 4A).

Hen 5657 and rooster 4133 were bred to non-transgenic chickens to obtain offspring hemizygous for the transgene. The pedigrees of transgenic chickens bred from rooster 4133 or hen 5657 and the subsequent generations are shown in FIG. 5. Transgenic rooster 5308 was also bred but this bird's progeny exhibited lactamase concentrations that were either very low or not detectable in serum and egg white. Active lactamase concentrations in the serum of randomly selected G2 transgenic chicks were measured at 3 to 90 days post-hatch. Of the five G2 transgenics bred from hen 5657, all had active lactamase at concentrations of 1.9 to 2.3 μg/ml (compared to the parental expression of 1.1 μg/ml, FIG. 4B). All of the samples were collected during the same period of time, thus, the lactamase concentrations in the serum of the offspring were expected to be higher than that of the parent since the concentration in hen 5657 had dropped proportionately as she matured. Similarly, the five randomly selected transgenic chicks bred from rooster 4133 all had serum lactamase concentrations that were similar but higher than that of their parent (FIG. 4B).

EXAMPLE 5

β-Lactamase Expression in the Egg White of Transgenic Hens

Figure 6:
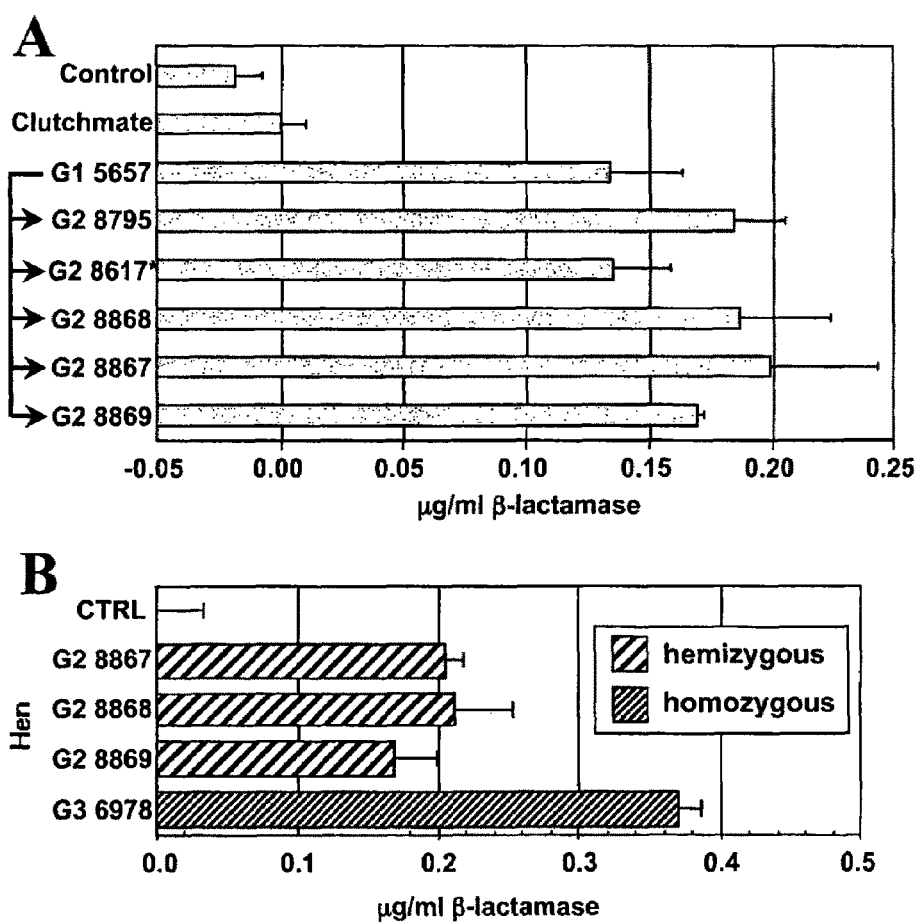
FIG. 6 shows β-lactamase (lactamase) in the egg white of hen 5657 and her offspring.

Eggs from G1 hen 5657 contained 130 ng of active β-lactamase (lactamase) per ml of egg white (FIG. 6A). Lactamase concentrations were higher in the first few eggs laid and then reached a plateau that was stable for at least nine months. Eggs from transgenic hens bred from hen 5657 and a non-transgenic rooster had lactamase concentrations that were similar to their parent (FIG. 6A). Hen 6978 was bred from G2 hen 8617 and sibling G2 rooster 8839 and was homozygous for the transgene as determined by quantitative PCR and Southern analysis. As expected, the concentration of lactamase in the eggs of bird 6978 was nearly two-fold higher than her hemizygous parent (FIG. 6B). No other G3 hens bred from hen 5657, were analyzed because hen 6978 was the only female in her clutch. It is important to note that the eggs from hens 8867, 8868 and 8869 were collected eleven months apart and had similar concentrations of lactamase (FIGS. 6A and 6B), again indicating that the expression levels in the egg white were consistent throughout the lay period.

Rooster 4133 was bred to non-transgenic hens to obtain hemizygous G2 hens. Of the 15 transgenic hens analyzed, all had lactamase in the egg white at concentrations ranging from 0.47 to 1.34 μg/ml. Four representative hens are shown in FIG. 7A. When assayed 6 months later, the average expression level had dropped from approximately 1.0 μg/ml to 0.8 μg/ml (FIG. 7A). Expression levels were high in the initial eggs and leveled out over several months. After that, the concentrations of lactamase in the eggs remained constant.

G2 hen 8150 and sibling G2 rooster 8191 were crossed to yield hemizygous and homozygous G3 hens. All transgenic G3 hens expressed lactamase in the white of their eggs at concentrations ranging from 0.52 to 1.65 μg/ml (FIG. 7B). The average expression for the G3 hens that were homozygous was 47% higher than those G2 hens and G3 hens that were hemizygous. The amount of lactamase in the eggs from G2 and G3 hens bred from rooster 4133 and his offspring varied significantly (FIGS. 7A and 7B), although the levels in the eggs from any given hen in that group were relatively constant. The average expression of lactamase was expected to double for the homozygous genotype. Western blot analysis confirmed that the transgene was faithfully producing intact lactamase in the eggs of G2 transgenics. The lactamase level detected on a Western blot also correlated closely with that determined by the enzyme activity assay, indicating that a significant portion of the egg white lactamase was bioactive. Thus, retroviral vectors were successfully employed to implement stable and reliable expression of a transgene in chickens.

Deposition of lactamase in the yolk was detectable but lower than that of egg white. Seven G2 or G3 hens of rooster 4133's lineage were analyzed and the concentration in the yolk ranged from 107 to 375 ng/ml or about 20% the concentration in the egg white. There was no correlation between the yolk and egg white lactamase levels of a given hen (Harvey et al., "Expression of exogenous protein in egg white of transgenic chickens" (April 2002) Nat. Biotechnol. 20:396-399).

EXAMPLE 6

Production of Founder Males

For pNLB-CMV-BL transduction, freshly laid fertilized White Leghorn eggs were used. Seven to ten microliters of concentrated particles were injected into the subgerminal cavity of windowed eggs and chicks hatched after sealing the window. 546 eggs were injected. Blood DNA was extracted and analyzed for the presence of the transgene using a probe-primer set designed to detect the neo resistance gene via the Taqman assay. As can be seen in Table 2 below, approximately 25% of all chicks had detectable levels of transgene in their blood DNA.

TABLE 2

| Transgene | NLB-CMV-BL |
|---|---|
| Summary of Transgenesis with the NLB-CMV-BL Vectors | |
| Number of injections | 546 |
| Number of birds hatched (%) | 126 (23.1%) |
| Number of chicks with transgene in their blood DNA (%) | 36 (28.6%) |
| Number of males | 56 |
| Number of males with transgene in their sperm DNA (%) | 3 (5.4%) |
| Summary of Transgenesis with the NLB-CMV-BL Vectors Continued | |
| Production of G1 flock | |
| Number of chicks bred from G0 males | 1026 |
| Number of G1 transgenics | 3 |
| Rate of germline transmission | 0.29% |
| Production of G2 flock | |
| Number of chicks bred from G1 transgenics | 120 |
| Number of G2 transgenics | 61 |
| Rate of germline transmission | 50.8% |
| Number of males that transmitted transgene to progeny (%) | 1 (1.8%) |

EXAMPLE 7

Germline Transmission of the Transgene

Taqman detection of the neo resistance gene in sperm DNA was used to identify candidate G0 males for breeding. Three G0 males were identified, wherein each had the NLB-CMV-BL transgene in their sperm DNA at levels that were above background. All G0 males positive for the transgene in their sperm were bred to non-transgenic hens to identify fully transgenic G1 offspring.

For NLB-CMV-BL 1026 chicks were bred, respectively, and three G1 chicks obtained for each transgene (Table 2, supra). All G1 progeny came from the male with the highest level of transgene in his sperm DNA, even though an equivalent number of chicks were bred from each male.

EXAMPLE 8

Southern Analysis of G1s and G2s

In order to confirm integration and integrity of the inserted vector sequences, Southern blot analysis was performed on DNA from G1 and G2 transgenics. Blood DNA was digested with HindIII and hybridized to a neo resistance probe to detect junction fragments created by the internal HindIII site found in the pNLB-CMV-BL vector (FIG. 3B) and genomic sites flanking the site of integration. Each of the 3 G1 birds carrying NLB-CMV-BL had a junction fragment of unique size, indicating that the transgene had integrated into three different genomic sites. G1s were bred to non-transgenic hens to obtain hemizygous G2s. As can be seen in Table 2 (supra), 50.8% of offspring from G1 roosters harboring NLB-CMV-BL were transgenic as expected for Mendelian segregation of a single integrated transgene. Southern analysis of HindIII-digested DNA from G2 offspring detected junction fragments similar in size to those originating from their transgenic parents, indicating that the transgene was transmitted intact.

EXAMPLE 9

Screening for G3 Progeny Homozygous for the Transgene

In order to obtain transgenic chickens homozygous for the transgene, G2 hemizygous birds having NLB-CMV-BL integrated at the same site (e.g., progeny of the same G1 male) were crossbred. Two groups were bred: the first was a hen and rooster arising from the G1 4133 male and the second from the G1 5657 hen. The Taqman assay was used to quantitatively detect the neo resistance transgene in G3 progeny using a standard curve. The standard curve was constructed using known amounts of genomic DNA from the G1 transgenic 4133 male hemizygous for the transgene as determined by Southern analysis. The standard curve ranged from $10^3$ to $1.6 \times 10^4$ total copies of the transgene or 0.2 to 3.1 transgene copies per diploid genome. Because reaction components were not limited during the exponential phase, amplification was very efficient and gave reproducible values for a given copy number. There was a reproducible, one-cycle difference between each standard curve differing two-fold in copy number.

In order to determine the number of transgene alleles in the G3 offspring, DNAs were amplified and compared to the standards. DNA from non-transgenics did not amplify. Birds homozygous for the transgenic allele gave rise to plots initiating the amplification one cycle earlier than those hemizygous for the allele. The sequence detection program was able to calculate the number of alleles in an unknown DNA sample based on the standard curve and the cycle threshold (Ct) at which a sample's amplification plot exhibited a significant rise. The data are shown in Table 3 below.

In order to confirm Taqman copy number analysis, DNA of selected birds was analyzed by Southern blotting using PstI-digested DNA and a probe complementary to the neo resistance gene to detect a 0.9 kb fragment. Detection of a small fragment was chosen since transfer of smaller DNAs from gel to membrane is more quantitative. The signal intensity of the 0.9 kb band corresponded well to the copy number of G3 transgenic birds as determined by the Taqman assay. The copy numbers of an additional eighteen G3 transgenic birds analyzed by Southern blotting were also consistent with that determined by Taqman. A total of 33 progeny were analyzed for the 4133 lineage, of which 9 (27.3%) were non-transgenic, 16 (48.5%) were hemizygous and 8 (24.2%) were homozygous. A total of 10 progeny were analyzed for the 5657 lineage, of which 5 (50.0%) were non-transgenic, 1 (10.0%) was hemizygous and 4 (40.0%) were homozygous. The observed ratio of non-transgenics, hemizygotes and homozygotes for the 4133 lineage G3 progeny was not statistically different from the expected 1:2:1 ratio as determined by the $\chi 2$ test (P is less than or equal to 0.05). Progeny of the 5657 lineage did not have the expected distribution but this could have been due to the low number of progeny tested (Harvey et al., "Consistent production of transgenic chickens using replication deficient retroviral vectors and high-throughput screening procedures" (February 2002) Poultry Science 81:202-212).

TABLE 3

Determination of Transgene Copy Number in G3 Offspring Bred from G2 Transgenics

| G1 Parent | Band No. (Std. No. or NTC[1]) | Ct[2] | Mean Total Copy Number | Standard Deviation | Copies per Diploid Genome[3] |
|---|---|---|---|---|---|
| NA[4] | 4133 | 27.3 | 3,975 | 145.7 | 1 |
| 4133 | 6792 | 40.0 | 0 | 0.0 | 0 |
| 5657 | 6977 | 25.9 | 10,510 | 587.0 | 2 |
| 5657 | 6978 | 25.8 | 10,401 | 505.1 | 2 |
| 4133 | 7020 | 26.7 | 6,064 | 443.1 | 1 |
| 4133 | 7021 | 26.8 | 5,239 | 133.8 | 1 |
| 4133 | 7022 | 26.1 | 9,096 | 352.3 | 2 |
| 4133 | 7023 | 26.8 | 5,424 | 55.7 | 1 |
| 4133 | 7024 | 26.9 | 4,820 | 110.1 | 1 |
| 5657 | 7110 | 26.4 | 8,092 | 1037.5 | 2 |
| 5657 | 7111 | 30.4 | 403 | 46.3 | 0 |
| 5657 | 7112 | 33.2 | 60 | 6.1 | 0 |
| 4133 | 7142 | 26.5 | 6,023 | 367.6 | 1 |
| 4133 | 7143 | 25.9 | 9,474 | 569.8 | 2 |
| 4133 | 7144 | 25.7 | 12,420 | 807.7 | 2 |
| 4133 | 7338 | 27.2 | 4,246 | 201.7 | 1 |
| 5657 | 7407 | 37.7 | 1 | 1.0 | 0 |
| NA | (std1) | 29.1 | 1,000 | 0.0 | 0.2 |
| NA | (std2) | 28.1 | 2,000 | 0.0 | 0.4 |
| NA | (std3) | 27.1 | 4,000 | 0.0 | 0.8 |
| NA | (std4) | 26.2 | 8,000 | 0.0 | 1.6 |
| NA | (std5) | 25.3 | 16,000 | 0.0 | 3.1 |
| NA | (NTC) | 39.8 | −1 | 0.0 | 0.0 |

[1]Std. No.: standard number; NTC: no template control.
[2]Ct: cycle threshold; cycle at which a sample's fluorescence exhibited a significant increase above background.
[3]Copies per diploid genome were determined by dividing the mean by 5100 and rounding to the nearest first decimal place.
[4]NA: not applicable.

EXAMPLE 10

Vector Construction for pNLB-MDOT-EPO Vector

Following the teachings of Example 1 (Vector Construction) of the specification, an pNLB-MDOT-EPO vector was created, substituting an EPO encoding sequence for the BL encoding sequence (FIG. 8B). Instead of using the CMV promoter, MDOT was used (FIG. 13). MDOT is a synthetic promoter which contains elements from both the ovomucoid (MD) and ovotransferrin (TO) promoter. (pNLB-MDOT-EPO vector, a.k.a. pAVIJCR-A145.27.2.2).

The DNA sequence for human EPO based on hen oviduct optimized codon usage was created using the BACKTRANSLATE program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins. The DNA sequence was synthesized and cloned into the 3' overhang T's of pCRII-TOPO (Invitrogen) by Integrated DNA Technologies, Coralville, Iowa, on a contractual basis. The EPO coding sequence was then removed from pEpoMM with Hind III and Fse I, purified from a 0.8% agarose-TAE Gel, and ligated to Hind III and Fse I digested, alkaline phosphatase-treated pCMV-IFNMM. The resulting plasmid was pAVIJCR-A137.43.2.2 which contained the EPO coding sequence controlled by the cytomegalovirus immediate early promoter/enhancer and SV40 polyA site. The plasmid pAVIJCR-A137.43.2.2 was digested with Nco I and Fse I and the appropriate fragment ligated to an Nco I and Fse I-digested fragment of pMDOTIFN to obtain pAVIJCR-A137.87.2.1 which contained EPO driven by the MDOT promoter. In order to clone the EPO coding sequence controlled by the MDOT promoter into the NLB retroviral plasmid, the plasmids pALVMDOTIFN and pAVIJCR-A137.87.2.1 were digested with Kpn I and Fse I. Appropriate DNA fragments were purified on a 0.8% agarose-TAE gel, then ligated and transformed into DH5 α cells. The resulting plasmid was pNLB-MDOT-EPO (a.k.a. pAVIJCR-A145.27.2.2).

EXAMPLE 11

Production of Transgenic Chickens and Fully Transgenic G1 Chickens Expressing EPO Production of NLB-MDOT-EPO transduction particles were performed as described for NLB-CMV-BL (see Example 2). Approximately 300 White Leghorn eggs were windowed according to the Speksnijder procedure (U.S. Pat. No. 5,897,998), then injected with about $7 \times 10^4$ transducing particles per egg. Eggs hatched 21 days after injection, and human EPO levels were measured by EPO ELISA from serum samples collected from chicks one week after hatch.

In order to screen for G0 roosters which contained the EPO transgene in their sperm, DNA was extracted from rooster sperm samples by Chelex-100 extraction (Walsh et al., 1991). DNA samples were then subjected to Taqman® analysis on a 7700 Sequence Detector (Perkin Elmer) using the "neo for-1" (5'-TGGATTGCACGCAGGTTCT-3'; SEQ ID NO: 5) and "neo rev-1" (5'-TGCCCAGTCATAGCCGAAT-3'; SEQ ID NO: 6) primers and FAM labeled NEO-PROBE1 (5'-CCTCTCCACCCAAGCGGCCG-3'; SEQ ID NO: 7) to detect the transgene. Eight G0 roosters with the highest levels of the transgene in their sperm samples were bred to nontransgenic SPAFAS (White Leghorn) hens by artificial insemination. Blood DNA samples were screened for the presence of the transgene by Taqman® analysis as described above.

Out of 1,054 offspring, 16 chicks were found to be transgenic (G1 avians). Chick serum was tested for the presence of human EPO by EPO ELISA, and EPO was present at about 70 nanogram/ml (ng/ml). Egg white in eggs from G1 hens was also tested for the presence of human EPO by EPO ELISA and found to contain human EPO at about 70 ng/ml. The EPO present in eggs (i.e., derived from the optimized coding sequence of human EPO) was found to be biologically active

EXAMPLE 12

Vector Construction for pNLB-CMV-IFN

Following the teachings of Example 1, a pNLB-CMV-IFN vector was created (FIG. 8A), substituting an IFN encoding sequence for the BL encoding sequence of Example 1.

An optimized coding sequence was created, wherein the most frequently used codons for each particular amino acid found in the egg white proteins ovalbumin, lysozyme, ovomucoid, and ovotransferrin were used in the design of the optimized human IFN-α 2b coding sequence that was inserted into vectors of the present invention. More specifically, the DNA sequence for optimized human IFN-α 2b is based on the hen oviduct optimized codon usage and was created using the BACKTRANSLATE program of the Wisconsin Package, Version 9.1 (Genetics Computer Group Inc., Madison, Wis.) with a codon usage table compiled from the chicken (*Gallus gallus*) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU was used as the codon for the majority of alanines in the optimized human IFN-α 2b coding sequence. The vectors containing the gene for optimized human IFN-α 2b were used to create transgenic avians that express transgenic poultry derived interferon-α 2b (TPD IFN-α 2b) in their tissues and eggs.

The template and primer oligonucleotides listed in Table 4 below were amplified by PCR with Pfu polymerase (Stratagene, La Jolla, Calif.) using 20 cycles of 94° C. for 1 min.; 50° C. for 30 sec.; and 72° C. for 1 min. and 10 sec. PCR products were purified from a 12% polyacrylamide-TBE gel by the "crush and soak" method (Maniatis et al. 1982), then combined as templates in an amplification reaction using only IFN-1 and IFN-8 as primers (see Table 4). The resulting PCR product was digested with Hind III and Xba I and gel purified from a 2% agarose-TAE gel, then ligated into Hind III and Xba I digested, alkaline phosphatase-treated pBluescript KS (Stratagene), resulting in the plasmid pBluKSP-IFNMag-Max. Both strands were sequenced by cycle sequencing on an ABI PRISM 377 DNA Sequencer (Perkin-Elmer, Foster City, Calif.) using universal T7 or T3 primers. Mutations in pBluKSP-IFN derived from the original oligonucleotide templates were corrected by site-directed mutagenesis with the Transformer Site-Directed Mutagenesis Kit (Clontech, Palo Alto, Calif.). The IFN coding sequence was then removed from the corrected pBluKSP-IFN with Hind III and Xba 1, purified from a 0.8% agarose-TAE Gel, and ligated to Hind III and Xba I digested, alkaline phosphatase-treated pCMV-BetaLa-3B-dH. The resulting plasmid was pCMV-IFN which contained an IFN coding sequence controlled by the cytomegalovirus immediate early promoter/enhancer and SV40 polyA site. In order to clone the IFN coding sequence controlled by the CMV promoter/enhancer into the NLB retroviral plasmid, pCMV-IFN was first digested with ClaI and XbaI, then both ends were filled in with Klenow fragment of DNA polymerase (New England BioLabs, Beverly, Mass.). pNLB-adapter was digested with NdeI and KpnI, and both ends were made blunt by T4 DNA polymerase (New England BioLabs). Appropriate DNA fragments were purified on a 0.8% agarose-TAE gel, then ligated and transformed into DH5 α cells. The resulting plasmid was pNLB-adapter-CMV-IFN. This plasmid was then digested with MluI and partially digested with BlpI and the appropriate fragment was gel purified. pNLB-CMV-EGFP was digested with MluI and BlpI, then alkaline-phosphatase treated and gel purified. The MluI/BlpI partial fragment of pNLB-adapter-CMV-IFN was ligated to the large fragment derived from the MluI/BlpI digest of pNLB-CMV-EGFP creating pNLB-CMV-IFN.

TABLE 4

| Template | Sequence of Template | Primer 1 | Sequence of Primer 1 | Primer 2 | Sequence of Primer 2 |
|---|---|---|---|---|---|
| IFN-A SEQ ID NO: 8 | 5'ATGGCTTTGACCTTTGCCTTACTG GTGGCTCTCCTGGTGCTGAGCTGCAA GAGCAGCTGCTCTGTGGGCTGCGATC TGCCTCA3' | IFN-1 SEQ ID NO: 9 | 5'CCCAAGCTTTCACCATGG CTTTGACCTTTGCCTTT3' | IFN-2 SEQ ID NO: 10 | 5'CTGTGGGTCTGAGG CAGAT3' |
| IFN-B SEQ ID NO: 11 | 5'GACCCACAGCCTGGGCAGCAGGA GGACCCTGATGCTGCTGGCTCAGAT GAGGAGAATCAGCCTGTTTAGCTGC CTGAAGGATAGGCACGATTTTGGCT TT3' | IFN-2b SEQ ID NO: 12 | 5'ATCTGCCTCAGACCCACA G3' | IFN-3b SEQ ID NO: 13 | 5'AACTCCTCTTGAGG AAAGCCAAAATC3' |
| IFN-C SEQ ID NO: 14 | 5'CTCAAGAGGAGTTTGGCAACCAG TTTCAGAAGGCTGAGACCATCCCTG TGCTGCACGAGATG3' | IFN-3c SEQ ID NO: 15 | 5'GATTTTGGCTTTCCTCAA GAGGAGTT3' | IFN-4 SEQ ID NO: 16 | 5'ATCTGCTGGATCAT CTCGTGC3' |
| IFN-D SEQ ID NO: 14 | 5'ATCCAGCAGATCTTTAACCTGTT TAGCACCAAGGATAGCAGCGCTGCT TGGGATGAGACCCTGCTGGATAAGT TTTACACCGAGCTGTACCAGCA3' | IFN-4b SEQ ID NO: 18 | 5'GCACGAGATGATCCAGC AGAT3' | IFN-5 SEQ ID NO: 19 | 5'ATCGTTCAGCTGCT GGTACA3' |
| IFN-E SEQ ID NO: 20 | 5'GCTGAACGATCTGGAGGCTTGCG TGATCCAGGGCGTGGGCGTGACCGA GACCCCTCTGATGAAGGAGGATAGC GCATCCT3' | IFN-5b SEQ ID NO: 21 | 5'TGTACCAGCAGCTGAAC GAT3' | IFN-6 SEQ ID NO: 22 | 5'CCTCACAGCCAGGA TGCTAT3' |
| IFN-F SEQ ID NO: 23 | 5'GGCTGTGAGGAAGTACTTTCAGA GGATCACCCTGTACCTGAAGGAGAA GAAGTACAGCCCTTGCGCTTGGGAA GTCGTGAGGG3' | IFN-6b SEQ ID NO: 24 | 5'ATAGCATCCTGGCTGTGA GG3' | IFN-7 SEQ ID NO: 25 | 5'ATGATCTCAGCCCT CACGAC3' |
| IFN-G SEQ ID NO: 26 | 5'CTGAGATCATGAGGAGCTTTAGC CTGAGCACCAACCTGCAAGAGAGCT TGAGGTCTAAGGAGTAA3' | IFN-7b SEQ ID NO: 27 | 5'GTCGTGAGGGCTGAGAT CAT3' | IFN-8 SEQ ID NO: 28 | 5'TGCTCTAGACTTTT TACTCCTTAGACCTCA AGCTCT3' |

EXAMPLE 13

Production of Transgenic Chickens and Fully Transgenic G1 Chickens Expressing IFN Transduction particles of pNLB-CMV-IFN were produced following the procedures of Example 2. Approximately 300 White Leghorn (strain Line 0) eggs were windowed according to the Speksnijder procedure (U.S. Pat. No. 5,897,998), then injected with about $7\times10^4$ transducing particles per egg. Eggs hatched 21 days after injection, and human IFN levels were measured by IFN ELISA from serum samples collected from chicks one week after hatch.

In order to screen for G0 roosters which contained the IFN transgene in their sperm, DNA was extracted from rooster sperm samples by Chelex-100 extraction (Walsh et al., 1991). DNA samples were then subjected to Taqman® analysis on a 7700 Sequence Detector (Perkin Elmer) using the "neo for-1" (5'-TGGATTGCACGCAGGTTCT-3'; SEQ ID NO: 5) and "neo rev-1" (5'-GTGCCCAGTCATAGCCGAAT-3'; SEQ ID NO: 6) primers and FAM labeled NEO-PROBE1 (5'-CCTCTCCACCCAAGCGGCCG-3'; SEQ ID NO: 7) to detect the transgene. Three G0 roosters with the highest levels of the transgene in their sperm samples were bred to nontransgenic SPAFAS (White Leghorn) hens by artificial insemination.

Blood DNA samples were screened for the presence of the transgene by Taqman® analysis as described above. Out of 1,597 offspring, one rooster was found to be transgenic (a.k.a. "Alphie"). Alphie's serum was tested for the presence of hIFN by hIFN ELISA, and hIFN was present at 200 ng/ml.

Alphie's sperm was used for artificial insemination of non-transgenic SPAFAS (White Leghorn) hens. 106 out of 202 (about 52%) offspring contained the transgene as detected by Taqman® analysis. These breeding results followed a Mendelian inheritance pattern and indicated that Alphie is transgenic.

EXAMPLE 14

Carbohydrate Analysis of Transgenic Poultry Derived Interferon-α 2b (TPD IFN-α 2b)

Experimental evidence revealed a new glycosylation pattern in interferon-α 2b derived from avians (i.e., TPD IFN-α 2b). TPD IFN-α 2b was found to contain two new glyco forms (bands 4 and 5 are α-Gal extended disaccharides; see FIG. 9) not normally seen in human peripheral blood leukocyte derived interferon-α 2b (PBL IFN-α 2b) or natural human interferon-α 2b (natural hIFN). TPD IFN-α 2b was also found to contain O-linked carbohydrate structures that are similar to human PBL IFN-α 2b and was more efficiently produced in chickens then the human form.

The coding sequence for human IFN-α 2b was optimized (Example 12, supra) resulting in a recombinant IFN-α 2b coding sequence. TPD IFN-α 2b was then produced in chickens (Example 13, supra). A carbohydrate analysis, including a monosaccharide analysis and FACE analysis, revealed the sugar make-up or novel glycosylation pattern of the protein. As such, TPD IFN-α 2b showed the following monosaccharide residues: N-Acetyl-Galactosamine (NAcGal), Galactose (Gal), N-Acetyl-Glucosamine (NAcGlu), and Sialic acid (SA). No N-linked glycosylation was found in TPD IFN-α 2b. Instead, TPD IFN-α 2b was found to be O-glycosylated at Thr-106. This type of glycosylation is similar to human IFN-α 2, wherein the Thr residue at position 106 is unique to IFN-α2. In addition, TPD IFN-α2b was found to have no mannose residues. A FACE analysis revealed 6 bands (FIG. 9) that represent various sugar residues, wherein bands 1, 2 and 3 are un-sialyated, mono-sialyated, and di-sialyated, respectively (FIG. 10). The sialic acid (SA) linkage is alpha 2-3 to Galactose (Gal) and alpha 2-6 to N-Acetyl-Galactosamine (NAcGal). Band 6 represents an un-sialyated tetrasaccharide. Bands 4 and 5 were found to be alpha-Galactose (alpha-Gal) extended disaccharides that are not seen in human PBL IFN-α 2b. FIG. 10 shows the comparison of TPD IFN-α2b (egg white hIFN) and human PBL IFN-α 2b (natural hIFN). Minor bands were present between bands 3 and 4 and between bands 4 and 5 in TPD IFN-α 2b (vide infra).

The protein was found to be O-glycosylated at Thr-106 with specific residues, such as:

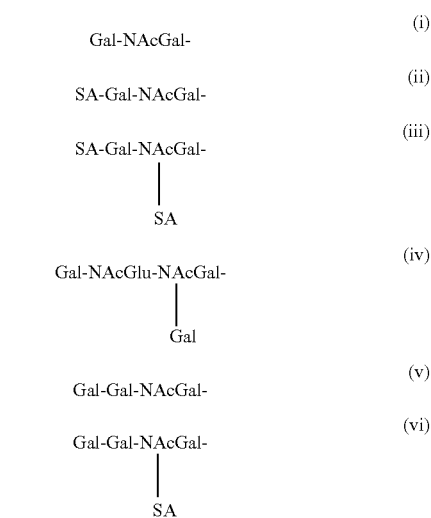

wherein Gal=Galactose,
NAcGal=N-Acetyl-Galactosamine,
NAcGlu=N-Acetyl-Glucosamine, and
SA=Sialic Acid.

The percentages were as follows:

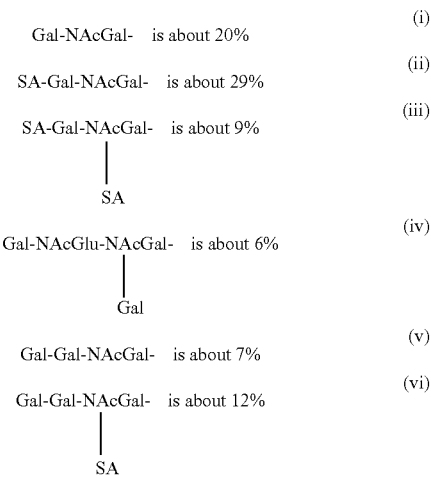

Minor bands were present between bands 3 and 4 and between bands 4 and 5 which account for about 17% in TPD IFN-α 2b.

EXAMPLE 15

Expression of MAbs from Plasmid Transfection and Retroviral Transduction Using the EMCV IRES in Avian Cells The light chain (LC) and heavy chain (HC) of a human monoclonal antibody were expressed from a single vector, pCMV-LC-emcvIRES-HC, by placement of an IRES from the encephalomyocarditis virus (EMCV) (see also Jang et al. (1988) "A segment of the 5′ nontranslated region of encephalomyocarditis virus RNA directs internal entry of ribosomes during in vitro translation" J. Virol. 62:2636-2643) between the LC and HC coding sequences. Transcription was driven by the CMV promoter.

In order to test expression of monoclonal antibodies from two separate vectors, the LC or HC linked to the CMV promoter were cotransfected into LMH/2a cells, an estrogen-responsive, chicken hepatocyte cell line (see also Binder et al. (1990) "Expression of endogenous and transfected apolipoprotein II and vitellogenin II genes in an estrogen responsive chicken liver cell line" Mol. Endocrinol. 4:201-208). Cotransfection of pCMV-LC and pCMV-HC resulted in 392 ng/ml of MAbs determined by a MAb ELISA whereas transfection of pCMV-LC-emcvIRES-HC resulted in 185 ng/ml of MAb.

The CMV-LC-emcv-HC cassette was inserted in a retroviral vector based on the Moloney murine leukemia virus (MLV), creating pL-CMV-LC-emcvIRES-HC-RN-BG. LMH cells (see also Kawaguchi et al. (1987) "Establishment and characterization of a chicken hepatocellular carcinoma cell line, LMH" Cancer Res. 47:4460-4464), the parent line of LMH/2a, were used as target cells because they are not neomycin resistant. LMH cells were transduced with the L-CMV-LC-emcvIRES-HC-RN-BG retroviral vector and selected with neomycin and passaged for several weeks. LMH cells were separately transduced and neomycin selected with the parent MLV vector, LXRN. Media from LXRN cells were negative for MAb, whereas media from the L-CMV-LC-emcvIRES-HC-RN-BG-transduced cells contained 22 ng/ml of MAb.

EXAMPLE 16

Production of Transgenic Chickens and Fully Transgenic G1 Chickens Expressing MAbs A pNLB-CMV-LC-emcv-HC vector is produced by substituting the CMV-LC-emcv-HC cassette of Example 15 for the CMV-BL cassette of pNLB-CMV-BL of Example 1.

Transduction particles of pNLB-CMV-LC-emcv-HC are produced following the procedures of Example 2. Approximately 300 White Leghorn (strain Line 0) eggs are windowed according to the Speksnijder procedure (U.S. Pat. No. 5,897, 998) and are then injected with about $7\times10^4$ transducing particles per egg. Eggs hatch 21 days after injection, and human MAb levels are measured by ELISA from serum samples collected from chicks one week after hatch.

G0 roster which contain the transgene in their sperm are identified by Taqman® analysis. Three G0 roosters with the highest levels of the transgene in their sperm samples are bred to nontransgenic SPAFAS (White Leghorn) hens by artificial insemination.

Over 1000 offspring are screened and more than 10 chicks are found to be transgenic (G1 avians). Chick serum is tested for the presence of the MAb by ELISA. The MAb is found to be present in an amount greater than 10 μg/ml of serum. Egg white in eggs from G1 hens is also tested for the presence of the MAb by ELISA and is found to be present in an amount greater than 10 μg/ml of egg white.

EXAMPLE 17

Construction of pNLB-CMV-hG-CSF

This vector construction effectively replaces the IFN coding region of the pNLB-CMV-IFN vector of Example 12 with the coding sequence of G-CSF. The hG-CSF ORF (human granulocyte colony stimulating factor open reading frame) was amplified from pORF9-hG-CSFb (cat. no. porf-hgcsfb, Invivogen, San Diego, Calif.) with the primers 5′GCSF (gggggaagctttcaccatggctggacctgcca; SEQ ID NO: 32) and 3′GCSF (actagactttcagggctgggcaaggtggcg; SEQ ID NO: 33) to create a 642 base pair (bp) PCR product. In order to provide the pNLB-CMV-hG-CSF construct with a sequence 3′ of the G-CSF coding sequence identical to that found in pNLB-CMV-IFN alpha-2b, an 86 bp fragment of pNLB-CMV-IFN alpha-2b, which is present adjacent to the 3′ end of the INF coding sequence, was amplified by PCR using the primers 5′GCSF-NLB (ccagccctgaaaagtctagtatggggattggtg; SEQ ID NO: 34) and 3′GCSF-NLB (gggggggctcagctggaattccgcc; SEQ ID NO: 35). The two PCR products (642 bp and 86 bp) were mixed and fused by PCR amplification with primers 5′GCSF and 3′GCSF-NLB. The PCR product was cloned into pCR®4Blunt-TOPO® plasmid vector (Invitrogen) according to the manufacturer's instructions and electroporated into DH5α-E cells, producing pFusion-hG-CSF-NLB. pFusion-hG-CSF-NLB was digested with Hind III and Blp I and the 690 bp G-CSF fragment was gel purified. The IFN alpha-2b coding sequence was removed from pNLB-CMV-IFN alpha-2b by digesting with Blp I. The vector was then religated and clones were selected which lacked the IFN coding insert, creating pNLB-CMV-delta hIFN alpha-2b. pNLB-CMV-delta IFN alpha-2b was digested with Blp I and partially digested with Hind III and the 8732 bp Blp I-Hind III vector fragment was gel purified. The 8732 bp fragment was ligated to the 690 bp Hind III/Blp I G-CSF fragment to create pNLB-CMV-G-CSF. The G-CSF ORF was verified by sequencing.

EXAMPLE 18

Production of Transgenic Chickens Expressing Human Granulocyte Colony Stimulating Factor (hG-CSF).

Production of NLB-CMV-hG-CSF transduction particles was performed as described for NLB-CMV-BL in Example 2. The embryos of 277 stage X eggs were injected with 7 μl of NLB-CMV-hG-CSF transduction particles (titers were $2.1\times 10^7$-$6.9\times10^7$). 86 chicks hatched and were raised to sexual maturity. 60 chicks tested positive for G-CSF which were evenly divided in sex; 30 male and 30 females. Egg white from 21 hens was assayed by ELISA for the presence of hG-CSF. Five hens were found to have significant levels of hG-CSF protein in the egg white at levels that ranged from 0.05 ug/ml to 0.5 μg/ml.

DNA was extracted from rooster sperm samples by Chelex-100 extraction (Walsh et al., 1991). DNA samples were then subjected to Taqman™ analysis on a 7700 Sequence Detector (Perkin Elmer) using the primers SJ-G-CSF for (cagagcttcctgctcaagtgctta) and SJ-G-CSF rev (ttgtaggtggcacacagcttct) and the probe, SJ-G-CSF probe (agcaagtgaggaagatccagggcg), to detect the transgene. The rooster with the highest levels of the transgene in his sperm samples was bred to nontransgenic SPAFAS (White Leghorn) hens by artificial insemination.

Blood DNA samples were screened for the presence of the transgene by Taqman™ analysis as described above. Out of 2264 offspring, 13 G1s were found to be transgenic and each were serum positive for the presence of G-CSF with one hen (XGF498) having approximately 136.5 ng/ml G-CSF in the serum and 5.6 µg/ml G-CSF in the egg white, each as measured by ELISA.

Two G1 roosters (QGF910 and DD9027) which were of the same line as XGF498 (therefore having the identical transgene inserted into identical position in the genome) were crossed with nontransgenic hens, to produce female offspring that lay eggs containing poultry derived G-CSF. Milligram quantities of the G-CSF were purified from egg white collected from eggs of QGF910 and DD9027 offspring. Patterns of representative glycosylation structures of the poultry derived G-CSF were determined from the G-CSF obtained as disclosed in Example 20.

EXAMPLE 19

Production of Transgenic Chickens Expressing Human Cytotoxic Lymphocyte Antigen Four-Fc Fusion Protein (CTLA4-Fc)

pNLB-1.8OM-CTLA4Fc and pNLB-3.9OM-CTLA4Fc were constructed as disclosed in U.S. patent application Ser. No. 11/047,184, filed Jan. 31, 2005, the disclosure of which is incorporated in its entirety herein by reference. Production of pNLB-1.8OM-CTLA4Fc and pNLB-3.9OM-CTLA4Fc transduction particles were performed as described for pNLB-CMV-BL in Example 2. 193 white leghorn eggs were injected with 7 µl of pNLB-1.8OM-CTLA4Fc transduction particles (titers were ~4×10$^6$) and 72 chicks hatched. 199 white leghorn eggs were injected with 7 l1 of pNLB-3.9OM-CTLA4Fc transduction particles (titers were ~4×10$^6$) and 20 chicks hatched.

Egg white from 30 hens produced with the pNLB-1.8OM-CTLA4Fc particles were assayed by ELISA for the presence of CTLA4-Fc. One hen was found to have significant levels of CTLA4-Fc protein in the egg white at an average level of 0.132 µg/ml (5 eggs assayed).

Egg white from seven hens produced with the pNLB-3.9OM-CTLA4Fc particles were assayed by ELISA for the presence of CTLA4-Fc. Two hens were found to have significant levels of CTLA4-Fc protein in the egg white at an average level of 0.164 µg/ml (5 eggs assayed) for one hen and an average level of 0.123 µg/ml (5 eggs assayed) for the second positive hen.

EXAMPLE 20

Carbohydrate Analysis of Transgenic Poultry Derived G-CSF

The TPD G-CSF oligosaccharide structures were determined by employing the following analysis. techniques as are well known to practitioners of skill in the art. MALDI-TOF-MS (Matrix assisted laser desorption ionization time-of-flight mass spectrometry) analysis and ESI MS/MS (electrospray ionization tandem mass spectrometry) were performed on the oligosaccharides after release from the peptide backbone. The O-linked oligosaccharides were chemically released from the protein and were permethylated using the NaOH method involving reaction with methyl iodide under anhydrous DMSO and extracted into chloroform prior to analysis. Direct mass spectrometry was performed on the intact glycosylated G-CSF. Analyses were also performed on the polysaccharide structures using HPLC analysis. Briefly, after release from the protein backbone the structures were separated using HPLC. Samples of the individual polysaccharide species were digested with certain enzymes and the digest products were analyzed by HPLC providing for structure determination as is understood in the art.

The structures as determined are shown below. Interestingly, Structure C and Structure D may be precursor forms of Structure E shown in the figure. It has been estimated, the invention not being limited thereto, that structure A is present on the poultry derived glycosylated G-CSF about 20% to about 40% of the time and that structure B is present on the poultry derived glycosylated G-CSF about 5% to about 25% of the time and that structure C is present on the poultry derived glycosylated G-CSF about 10% to about 20% of the time and that structure D is present on the poultry derived glycosylated G-CSF about 5% to about 15% of the time and that structure E is present on the poultry derived glycosylated G-CSF about 1% to about 5% of the time and that structure F is present on the poultry derived glycosylated G-CSF about 10% to about 25% of the time and that structure G is present on the poultry derived glycosylated G-CSF about 20% to about 30% of the time.

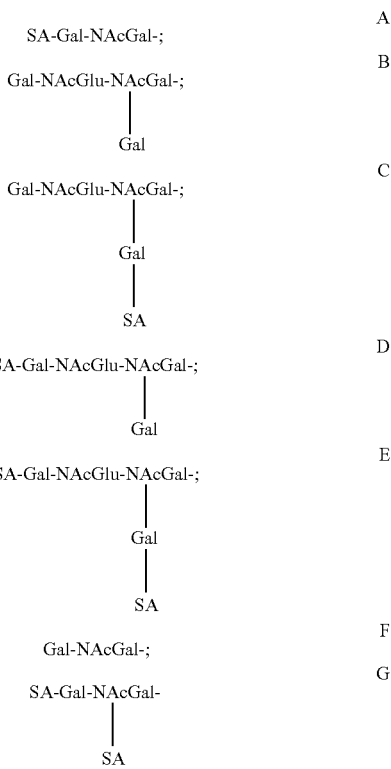

Monosaccharide analysis was performed by GC/MS (gas chromatography-mass spectrometry) on poultry derived G-CSF that had been spiked with Arabitol (internal standard), hydrolyzed, N-acetylated and TMS derivatized using methods readily available to those skilled in the art. The derivatized sample was compared to a standard mixture of sugars similarly derivatized. Sialic acid analysis of the poultry derived G-CSF was performed after spiking with ketodeoxynonulosonic acid, lyophilized then hydrolyzed, desalted and re-lyophilized. Analysis of the sample was performed on a Dionex BioLC system using appropriate standards. These analyses showed the presence of galactose, glucose, N-acetylgalactosamine, N-acetylglucosamine and sialic acid (N-acetylneuraminic acid) as seen in Table 5. The data in Table 5 supersedes preliminary data generated by HPAEC-PAD analysis which determined a greater percentage of N-acetylglucosamine to be present.

TABLE 5

| Monosaccharide | TPD G-CSF | |
|---|---|---|
| | Nmoles detected | Nmoles Detected/mg |
| Galactose | 4.5 | 34.5 |
| N-Acetylgalactosamine | 2.9 | 22.2 |
| N-Acetylglucosamine | 0.95 | 7.3 |
| Sialic Acid | 6.0 | 46.0 |

Linkage analysis was performed on a permethylated glycan sample of the poultry derived G-CSF that was hydrolyzed in TFA and reduced in sodium borodeuteride. The borate was removed by three additions of methanol:glacial acetic acid (9:1) followed by lyophilization and then acetylation by acetic anhydride. After purification by extraction with chloroform, the sample was examined by GC/MS. A mixture of standards was also run under the same conditions. The linkages were determined as follows:
i. The sialic acid linkage is 2-3 to galactose and 2-6 to N-acetylgalactosamine
ii. The galactose linkage is 2-3 to N-acetylgalactosamine and 2-4 to N-acetylglucosamine
iii. The N-acetylglucosamine linkage is 2-6 to N-acetylgalactosamine

EXAMPLE 21

In vitro Cell Proliferation Activity of Poultry Derived G-CSF (TPD G-CSF)

Figure 17:
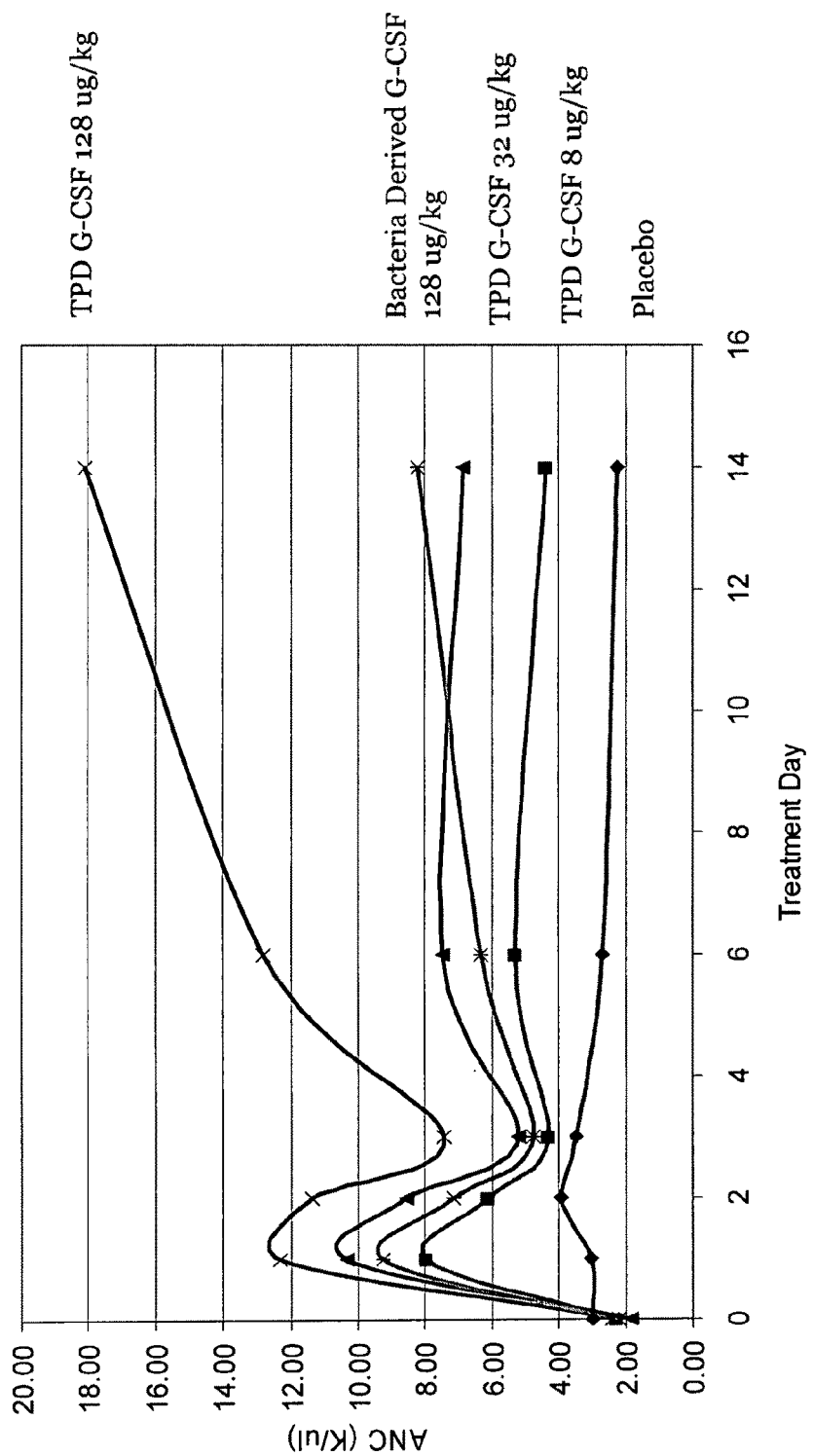
FIG. 17 depicts the increase in Absolute Neutrophil Count (ANC) of TPD G-CSF compared to bacterial derived human G-CSF over a 14 day period.

The in vitro biological activity of TPD G-CSF was demonstrated using the NFS-60 cell proliferation assay. Briefly, NFS-60 cells were maintained in growth media containing GM-CSF. Confluent cultures were harvested, washed and plated at a cell density of $10^5$ cells per well with growth media alone. TPD G-CSF and bacterial derived human G-CSF (i.e., Neupogen®) were serial diluted in growth media and added to separate wells in triplicate. Cell proliferation was determined by metabolic reduction of 3-(4,5-dimethylthiazol-2-yl)-2,5-diphenyltetrazolium bromide (MTT) and was quantified spectrophotometrically. The specific activity of the avian derived G-CSF was determined by comparing the $ED_{50}$ of Neupogen® with that of the purified avian derived G-CSF. The specific activity of TPD G-CSF over a 14 day period was determined to be well in excess of that of the bacterial derived G-CSF Neupogen® (non-glycosylated G-CSF). See FIG. 17.

All documents (e.g., U.S. patents, U.S. patent applications, publications) cited in the above specification are incorporated herein by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A composition comprising an isolated human G-CSF having a chicken-derived glycosylation pattern wherein the glycosylation pattern is other than that of G-CSF produced in a CHO cell.

2. An isolated human G-CSF having a chicken-derived glycosylation pattern wherein the glycosylation pattern is other than that of G-CSF produced in a CHO cell.

3. The composition of claim 1 wherein the G-CSF is present in a hard shell egg.

4. The composition of claim 1 wherein an G-CSF is glycosylated in an oviduct cell of an avian.

5. The composition of claim 4 wherein the oviduct cell is a tubular gland cell.

6. The composition of claim 1 wherein an G-CSF is glycosylated in an oviduct cell of a chicken.

7. The composition of claim 1 wherein the G-CSF is glycosylated at threonine 133.

8. The composition of claim 1 wherein the composition is a pharmaceutical composition.

9. The composition of claim 1 wherein the G-CSF has the amino acid sequence of SEQ ID NO: 41.

10. The composition of claim 1 wherein the glycosylation pattern is other than that of G-CSF produced in a human cell.

* * * * *

SEQUENCE LISTING

```
<160> NUMBER OF SEQ ID NOS: 41

<210> SEQ ID NO 1
<211> LENGTH: 498
<212> TYPE: DNA
<213> ORGANISM: Artificial Sequence
<220> FEATURE:
<223> OTHER INFORMATION: Transgenic Poultry Derived IFN alpha 2b CDS

<400> SEQUENCE: 1
tgcgatctgc ctcagaccca cagcctgggc agcaggagga ccctgatgct gctggctcag      60
atgaggagaa tcagcctgtt tagctgcctg aaggataggc acgattttgg ctttcctcaa     120
gaggagtttg gcaaccagtt tcagaaggct gagaccatcc ctgtgctgca cgagatgatc     180
cagcagatct ttaacctgtt tagcaccaag gatagcagcg ctgcttggga tgagaccctg     240
ctggataagt tttacaccga gctgtaccag cagctgaacg atctggaggc ttgcgtgatc     300
cagggcgtgg gcgtgaccga gacccctctg atgaaggagg atagcatcct ggctgtgagg     360
aagtactttc agaggatcac cctgtacctg aaggagaaga gtacagccc ctgcgcttgg     420 gaagtcgtga gggctgagat catgaggagc tttagcctga gcaccaacct gcaagagagc     480
ttgaggtcta aggagtaa                                                    498

<210> SEQ ID NO 2
<211> LENGTH: 165
<212> TYPE: PRT
<213> ORGANISM: Artificial Sequence
```

-continued

```
<220> FEATURE:
<223> OTHER INFORMATION: Transgenic Poultry Derived IFN alpha 2b

<400> SEQUENCE: 2

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 3
<211> LENGTH: 579
<212> TYPE: DNA
<213> ORGANISM: Artificial Sequence
<220> FEATURE:
<223> OTHER INFORMATION: Transgenic Poultry Derived EPO CDS

<400> SEQUENCE: 3
atgggcgtgc acgagtgccc tgcttggctg tggctgctct tgagcctgct cagcctgcct      60
ctgggcctgc ctgtgctggg cgctcctcca aggctgatct gcgatagcag ggtgctggag     120
aggtacctgc tggaggctaa ggaggctgag aacatcacca ccggctgcgc tgagcactgc     180
agcctgaacg agaacatcac cgtgcctgat accaaggtga acttttacgc ttggaagagg     240
atggaggtgg gccagcaggc tgtggaggtg tggcagggcc tggctctgct gagcgaggct     300
gtgctgaggg gccaggctct gctggtgaac agctctcagc cttgggagcc tctgcagctg     360
cacgtggata aggctgtgag cggcctgaga agcctgacca ccctgctgag ggctctgggc     420
gctcagaagg aggctatcag ccctccagat gctgcaagcg ctgcccctct gaggaccatc     480
accgctgata cctttaggaa gctgtttagg gtgtacagca actttctgag gggcaagctg     540
aagctgtaca ccggcgaggc ttgcaggacc ggcgatagg                           579

<210> SEQ ID NO 4
<211> LENGTH: 193
<212> TYPE: PRT
<213> ORGANISM: Artificial Sequence
<220> FEATURE:
<223> OTHER INFORMATION: Transgenic Poultry Derived EPO

<400> SEQUENCE: 4

Met Gly Val His Glu Cys Pro Ala Trp Leu Trp Leu Leu Leu Ser Leu
```

```
            1               5              10              15

Leu Ser Leu Pro Leu Gly Leu Pro Val Leu Gly Ala Pro Pro Arg Leu
                20              25              30

Ile Cys Asp Ser Arg Val Leu Glu Arg Tyr Leu Leu Glu Ala Lys Glu
                35              40              45

Ala Glu Asn Ile Thr Thr Gly Cys Ala Glu His Cys Ser Leu Asn Glu
            50              55              60

Asn Ile Thr Val Pro Asp Thr Lys Val Asn Phe Tyr Ala Trp Lys Arg
65              70              75              80

Met Glu Val Gly Gln Gln Ala Val Glu Val Trp Gln Gly Leu Ala Leu
                85              90              95

Leu Ser Glu Ala Val Leu Arg Gly Gln Ala Leu Leu Val Asn Ser Ser
                100             105             110

Gln Pro Trp Glu Pro Leu Gln Leu His Val Asp Lys Ala Val Ser Gly
                115             120             125

Leu Arg Ser Leu Thr Thr Leu Leu Arg Ala Leu Arg Ala Gln Lys Glu
                130             135             140

Ala Ile Ser Pro Pro Asp Ala Ala Ser Ala Ala Pro Leu Arg Thr Ile
145             150             155             160

Thr Ala Asp Thr Phe Arg Lys Leu Phe Arg Val Tyr Ser Asn Phe Leu
                165             170             175

Arg Gly Lys Leu Lys Leu Tyr Thr Gly Glu Ala Cys Arg Thr Gly Asp
                180             185             190

Arg

<210> SEQ ID NO 5
<211> LENGTH: 19
<212> TYPE: DNA
<213> ORGANISM: Artificial Sequence
<220> FEATURE:
<223> OTHER INFORMATION: neo for-1 primer

<400> SEQUENCE: 5
tggattgcac gcaggttct                                            19

<210> SEQ ID NO 6
<211> LENGTH: 20
<212> TYPE: DNA
<213> ORGANISM: Artificial Sequence
<220> FEATURE:
<223> OTHER INFORMATION: neo rev-1 primer

<400> SEQUENCE: 6
gtgcccagtc atagccgaat                                           20

<210> SEQ ID NO 7
<211> LENGTH: 20
<212> TYPE: DNA
<213> ORGANISM: Artificial Sequence
<220> FEATURE:
<223> OTHER INFORMATION: NEO-PROBE1

<400> SEQUENCE: 7
cctctccacc caagcggccg                                           20

<210> SEQ ID NO 8
<211> LENGTH: 83
<212> TYPE: DNA
<213> ORGANISM: Artificial Sequence
<220> FEATURE:
```

<223> OTHER INFORMATION: IFN-A primer

<400> SEQUENCE: 8
atggctttga cctttgcctt actggtggct ctcctggtgc tgagctgcaa gagcagctgc    60
tctgtgggct gcgatctgcc tca                                            83

<210> SEQ ID NO 9
<211> LENGTH: 34
<212> TYPE: DNA
<213> ORGANISM: Artificial Sequence
<220> FEATURE:
<223> OTHER INFORMATION: IFN-1 primer

<400> SEQUENCE: 9
cccaagcttt caccatggct ttgacctttg cctt                                34

<210> SEQ ID NO 10
<211> LENGTH: 19
<212> TYPE: DNA
<213> ORGANISM: Artificial Sequence
<220> FEATURE:
<223> OTHER INFORMATION: IFN-2 primer

<400> SEQUENCE: 10
ctgtgggtct gaggcagat                                                 19

<210> SEQ ID NO 11
<211> LENGTH: 100
<212> TYPE: DNA
<213> ORGANISM: Artificial Sequence
<220> FEATURE:
<223> OTHER INFORMATION: IFN-B primer

<400> SEQUENCE: 11
gacccacagc ctgggcagca ggaggaccct gatgctgctg gctcagatga ggagaatcag    60
cctgtttagc tgcctgaagg ataggcacga ttttggcttt                         100

<210> SEQ ID NO 12
<211> LENGTH: 19
<212> TYPE: DNA
<213> ORGANISM: Artificial Sequence
<220> FEATURE:
<223> OTHER INFORMATION: IFN-2b primer

<400> SEQUENCE: 12
atctgcctca gacccacag                                                 19

<210> SEQ ID NO 13
<211> LENGTH: 26
<212> TYPE: DNA
<213> ORGANISM: Artificial Sequence
<220> FEATURE:
<223> OTHER INFORMATION: IFN-3b primer

<400> SEQUENCE: 13
aactcctctt gaggaaagcc aaaatc                                         26

<210> SEQ ID NO 14
<211> LENGTH: 62
<212> TYPE: DNA
<213> ORGANISM: Artificial Sequence
<220> FEATURE:
<223> OTHER INFORMATION: IFN-C primer

<400> SEQUENCE: 14
ctcaagagga gtttggcaac cagtttcaga aggctgagac catccctgtg ctgcacgaga    60
tg                                                                   62

<210> SEQ ID NO 15
<211> LENGTH: 26
<212> TYPE: DNA
<213> ORGANISM: Artificial Sequence
<220> FEATURE:
<223> OTHER INFORMATION: IFN-3c primer

<400> SEQUENCE: 15
gattttggct ttcctcaaga ggagtt                                         26

<210> SEQ ID NO 16
<211> LENGTH: 21
<212> TYPE: DNA
<213> ORGANISM: Artificial Sequence
<220> FEATURE:
<223> OTHER INFORMATION: IFN-4 primer

<400> SEQUENCE: 16
atctgctgga tcatctcgtg c                                              21

<210> SEQ ID NO 17
<211> LENGTH: 95
<212> TYPE: DNA
<213> ORGANISM: Artificial Sequence
<220> FEATURE:
<223> OTHER INFORMATION: IFN-D primer

<400> SEQUENCE: 17
atccagcaga tctttaacct gtttagcacc aaggatagca gcgctgcttg ggatgagacc    60
ctgctggata gttttacac cgagctgtac cagca                                95

<210> SEQ ID NO 18
<211> LENGTH: 21
<212> TYPE: DNA
<213> ORGANISM: Artificial Sequence
<220> FEATURE:
<223> OTHER INFORMATION: IFN-4b primer

<400> SEQUENCE: 18
gcacgagatg atccagcaga t                                              21

<210> SEQ ID NO 19
<211> LENGTH: 20
<212> TYPE: DNA
<213> ORGANISM: Artificial Sequence
<220> FEATURE:
<223> OTHER INFORMATION: IFN-5 primer

<400> SEQUENCE: 19
atcgttcagc tgctggtaca                                                20

<210> SEQ ID NO 20
<211> LENGTH: 78
<212> TYPE: DNA
<213> ORGANISM: Artificial Sequence
<220> FEATURE:
<223> OTHER INFORMATION: IFN-E primer

<400> SEQUENCE: 20
gctgaacgat ctggaggctt gcgtgatcca gggcgtgggc gtgaccgaga ccctctctgat   60 gaaggaggat agcatcct 78

<210> SEQ ID NO 21
<211> LENGTH: 20
<212> TYPE: DNA
<213> ORGANISM: Artificial Sequence
<220> FEATURE:
<223> OTHER INFORMATION: IFN-5b primer

<400> SEQUENCE: 21
tgtaccagca gctgaacgat 20

<210> SEQ ID NO 22
<211> LENGTH: 20
<212> TYPE: DNA
<213> ORGANISM: Artificial Sequence
<220> FEATURE:
<223> OTHER INFORMATION: IFN-6 primer

<400> SEQUENCE: 22
cctcacagcc aggatgctat 20

<210> SEQ ID NO 23
<211> LENGTH: 83
<212> TYPE: DNA
<213> ORGANISM: Artificial Sequence
<220> FEATURE:
<223> OTHER INFORMATION: IFN-F primer

<400> SEQUENCE: 23
ggctgtgagg aagtactttc agaggatcac cctgtacctg aaggagaaga agtacagccc 60
ttgcgcttgg gaagtcgtga ggg 83

<210> SEQ ID NO 24
<211> LENGTH: 20
<212> TYPE: DNA
<213> ORGANISM: Artificial Sequence
<220> FEATURE:
<223> OTHER INFORMATION: IFN-6b primer

<400> SEQUENCE: 24
atagcatcct ggctgtgagg 20

<210> SEQ ID NO 25
<211> LENGTH: 20
<212> TYPE: DNA
<213> ORGANISM: Artificial Sequence
<220> FEATURE:
<223> OTHER INFORMATION: IFN-7 primer

<400> SEQUENCE: 25
atgatctcag ccctcacgac 20

<210> SEQ ID NO 26
<211> LENGTH: 65
<212> TYPE: DNA
<213> ORGANISM: Artificial Sequence
<220> FEATURE:
<223> OTHER INFORMATION: IFN-G primer

<400> SEQUENCE: 26
ctgagatcat gaggagcttt agcctgagca ccaacctgca agagagcttg aggtctaagg 60
agtaa 65

<210> SEQ ID NO 27
<211> LENGTH: 20
<212> TYPE: DNA
<213> ORGANISM: Artificial Sequence
<220> FEATURE:
<223> OTHER INFORMATION: IFN-7b primer

<400> SEQUENCE: 27
gtcgtgaggg ctgagatcat                                              20

<210> SEQ ID NO 28
<211> LENGTH: 36
<212> TYPE: DNA
<213> ORGANISM: Artificial Sequence
<220> FEATURE:
<223> OTHER INFORMATION: IFN-8 primer

<400> SEQUENCE: 28
tgctctagac ttttactcc ttagacctca agctct                             36

<210> SEQ ID NO 29
<211> LENGTH: 69
<212> TYPE: DNA
<213> ORGANISM: Artificial Sequence
<220> FEATURE:
<223> OTHER INFORMATION: Lysozyme signal sequence

<400> SEQUENCE: 29
ccaccatggg gtctttgcta atcttggtgc tttgcttcct gccgctagct gccttagggc    60
cctctagag                                                          69

<210> SEQ ID NO 30
<211> LENGTH: 671
<212> TYPE: DNA
<213> ORGANISM: Artificial Sequence
<220> FEATURE:
<223> OTHER INFORMATION: MDOT promoter linked to IFN-MM CDS

<400> SEQUENCE: 30
atcgataggt accgggcccc ccctcgaggt gaatatccaa gaatgcagaa ctgcatggaa    60
agcagagctg caggcacgat ggtgctgagc cttagctgct tcctgctggg agatgtggat   120
gcagagacga atgaaggacc tgtcccttac tcccctcagc attctgtgct atttaggggtt  180 ctaccagagt ccttaagagg tttttttttt ttttggtcca aaagtctgtt tgtttggttt   240
tgaccactga gagcatgtga cacttgtctc aagctattaa ccaagtgtcc agccaaaatc   300
gatgtcacaa cttgggaatt ttccatttga agccccttgc aaaaacaaag agcaccttgc   360
ctgctccagc tcctggctgt gaagggtttt ggtgccaaag agtgaaaggc ttcctaaaaa   420
tgggctgagc cggggaaggg gggcaacttg ggggctattg agaaacaagg aaggacaaac   480
agcgttaggt cattgcttct gcaaacacag ccagggctgc tcctctataa aggggaaga    540 aagaggctcc gcagccatca cagacccaga ggggacggtc tgtgaatcaa gctttcacca   600
tggctttgac ctttgcctta ctggtggctc tcctggtgct gagctgcaag agcagctgct   660
cgtgggttgc g                                                       671

<210> SEQ ID NO 31
<211> LENGTH: 24
<212> TYPE: PRT
<213> ORGANISM: Artificial Sequence
<220> FEATURE:
<223> OTHER INFORMATION: MDOT promoter linked to IFN-MM CDS

```
<400> SEQUENCE: 31

Met Ala Leu Thr Phe Ala Leu Leu Val Ala Leu Leu Val Leu Ser Cys
1               5                   10                  15

Lys Ser Ser Cys Ser Trp Val Ala
            20

<210> SEQ ID NO 32
<211> LENGTH: 33
<212> TYPE: DNA
<213> ORGANISM: Artificial Sequence
<220> FEATURE:
<223> OTHER INFORMATION: 5?GCSF Primer

<400> SEQUENCE: 32 gggggggaagc tttcaccatg gctggacctg cca                              33

<210> SEQ ID NO 33
<211> LENGTH: 31
<212> TYPE: DNA
<213> ORGANISM: Artificial Sequence
<220> FEATURE:
<223> OTHER INFORMATION: 3?GCSF Primer

<400> SEQUENCE: 33
actagacttt tcagggctgg gcaaggtggc g                                 31

<210> SEQ ID NO 34
<211> LENGTH: 33
<212> TYPE: DNA
<213> ORGANISM: Artificial Sequence
<220> FEATURE:
<223> OTHER INFORMATION: 5?GCSF-NLB Primer

<400> SEQUENCE: 34
ccagccctga aaagtctagt atggggattg gtg                               33

<210> SEQ ID NO 35
<211> LENGTH: 25
<212> TYPE: DNA
<213> ORGANISM: Artificial Sequence
<220> FEATURE:
<223> OTHER INFORMATION: 3?GCSF-NLB Primer

<400> SEQUENCE: 35 ggggggggctc agctggaatt ccgcc                                       25

<210> SEQ ID NO 36
<211> LENGTH: 24
<212> TYPE: DNA
<213> ORGANISM: Artificial Sequence
<220> FEATURE:
<223> OTHER INFORMATION: SJ-G-CSF Primer

<400> SEQUENCE: 36
cagagcttcc tgctcaagtg ctta                                         24

<210> SEQ ID NO 37
<211> LENGTH: 22
<212> TYPE: DNA
<213> ORGANISM: Artificial Sequence
<220> FEATURE:
<223> OTHER INFORMATION: SJ-G-CSF rev Primer

<400> SEQUENCE: 37
ttgtaggtgg cacacagctt ct                                           22
```

```
<210> SEQ ID NO 38
<211> LENGTH: 24
<212> TYPE: DNA
<213> ORGANISM: Artificial Sequence
<220> FEATURE:
<223> OTHER INFORMATION: SJ-G-CSF probe

<400> SEQUENCE: 38
agcaagtgag gaagatccag ggcg                                            24

<210> SEQ ID NO 39
<211> LENGTH: 612
<212> TYPE: DNA
<213> ORGANISM: Artificial Sequence
<220> FEATURE:
<223> OTHER INFORMATION: G-CSF CDS

<400> SEQUENCE: 39
atggctggac ctgccaccca gagccccatg aagctgatgg ccctgcagct gctgctgtgg     60
cacagtgcac tctggacagt gcaggaagcc acccccctgg gccctgccag ctccctgccc    120
cagagcttcc tgctcaagtg cttagagcaa gtgaggaaga tccagggcga tggcgcagcg    180
ctccaggaga agctgtgtgc cacctacaag ctgtgccacc cgaggagct ggtgctgctc     240 ggacactctc tgggcatccc ctgggctccc ctgagcagct gccccagcca ggccctgcag    300
ctggcaggct gcttgagcca actccatagc ggcctttcc tctaccaggg gctcctgcag     360
gccctggaag ggatctcccc cgagttgggt cccaccttgg acacactgca gctggacgtc    420
gccgactttg ccaccaccat ctggcagcag atggaagaac tgggaatggc ccctgccctg    480
cagcccaccc agggtgccat gccggccttc gcctctgctt ccagcgccg ggcaggaggg     540 gtcctagttg cctcccatct gcagagcttc ctggaggtgt cgtaccgcgt tctacgccac    600
cttgcccagc cc                                                        612

<210> SEQ ID NO 40
<211> LENGTH: 204
<212> TYPE: PRT
<213> ORGANISM: Artificial Sequence
<220> FEATURE:
<223> OTHER INFORMATION: G-CSF Precursor

<400> SEQUENCE: 40

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125
```

-continued

```
Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
            195                 200

<210> SEQ ID NO 41
<211> LENGTH: 174
<212> TYPE: PRT
<213> ORGANISM: Artificial Sequence
<220> FEATURE:
<223> OTHER INFORMATION: G-CSF Mature Peptide

<400> SEQUENCE: 41

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```